US011224369B2

(12) United States Patent
Harris et al.

(10) Patent No.: US 11,224,369 B2
(45) Date of Patent: *Jan. 18, 2022

(54) SYSTEMS AND METHODS FOR AUTONOMOUS INTRAVENOUS NEEDLE INSERTION

(71) Applicant: Veebot Systems, Inc., Miami, FL (US)

(72) Inventors: Richard J. Harris, Coconut Grove, FL (US); Joseph B. Mygatt, Ridgefield, CT (US); Stuart I. Harris, Coconut Grove, FL (US)

(73) Assignee: Veebot Systems, Inc., Miami, FL (US)

( * ) Notice: Subject to any disclaimer, the term of this patent is extended or adjusted under 35 U.S.C. 154(b) by 349 days.

This patent is subject to a terminal disclaimer.

(21) Appl. No.: 16/363,881

(22) Filed: Mar. 25, 2019

(65) Prior Publication Data
US 2019/0357828 A1 Nov. 28, 2019

Related U.S. Application Data

(60) Continuation of application No. 15/881,341, filed on Jan. 26, 2018, now Pat. No. 10,238,327, which is a
(Continued)

(51) Int. Cl.
A61B 5/00 (2006.01)
A61B 5/153 (2006.01)
(Continued)

(52) U.S. Cl.
CPC .............. A61B 5/1535 (2013.01); A61B 5/14 (2013.01); A61B 5/153 (2013.01);
(Continued)

(58) Field of Classification Search
CPC combination set(s) only.
See application file for complete search history.

(56) References Cited

U.S. PATENT DOCUMENTS 4,619,249 A 10/1986 Landry
5,823,993 A 10/1998 Lemelson
(Continued)

FOREIGN PATENT DOCUMENTS

EP 0919193 A1 6/1999
WO 2000056213 A1 9/2000
WO 2010056538 A1 5/2010

OTHER PUBLICATIONS

PCT International Search Report based on PCT/US11/66978 dated Apr. 24, 2012.
(Continued)

Primary Examiner — Joel F Brutus
(74) Attorney, Agent, or Firm — Greenberg Traurig, LLP; David J. Dykeman; Roman Fayerberg

(57) ABSTRACT

Systems and methods for autonomous intravenous needle insertion are disclosed herein. In an embodiment, a system for autonomous intravenous insertion include a robot arm, one or more sensors pivotally attached to the robot arm for gathering information about potential insertion sites in a subject arm, a medical device pivotally attached to the robot arm, and a controller in communication with the sensors and the robot arm, wherein the controller receives the information from the sensors about potential insertion sites, and the controller selects a target insertion site and directs the robot arm to insert the medical device into the target insertion site.

21 Claims, 28 Drawing Sheets

Related U.S. Application Data continuation of application No. 15/154,656, filed on May 13, 2016, now Pat. No. 9,913,605, which is a division of application No. 13/335,700, filed on Dec. 22, 2011, now Pat. No. 9,364,171.

(60) Provisional application No. 61/426,022, filed on Dec. 22, 2010.

(51) Int. Cl.

| | |
|---|---|
| *A61B 5/145* | (2006.01) |
| *A61B 34/30* | (2016.01) |
| *A61B 5/15* | (2006.01) |
| *A61B 34/10* | (2016.01) |
| *A61B 34/00* | (2016.01) |
| *A61B 8/08* | (2006.01) |
| *A61M 5/20* | (2006.01) |
| *A61M 5/52* | (2006.01) |
| *A61B 17/00* | (2006.01) |
| *A61B 90/00* | (2016.01) |
| *A61B 90/11* | (2016.01) |

(52) U.S. Cl.
CPC .... *A61B 5/15003* (2013.01); *A61B 5/150068* (2013.01); *A61B 5/15074* (2013.01); *A61B 5/150389* (2013.01); *A61B 5/150503* (2013.01); *A61B 5/150732* (2013.01); *A61B 5/150748* (2013.01); *A61B 5/150946* (2013.01); *A61B 5/150954* (2013.01); *A61B 8/0891* (2013.01); *A61B 34/10* (2016.02); *A61B 34/25* (2016.02); *A61B 34/30* (2016.02); *A61M 5/20* (2013.01); *A61M 5/52* (2013.01); *A61B 90/11* (2016.02); *A61B 90/361* (2016.02); *A61B 2017/00057* (2013.01); *A61B 2017/00106* (2013.01); *A61B 2034/107* (2016.02)

(56) References Cited

U.S. PATENT DOCUMENTS

| | | | |
|---|---|---|---|
| 6,074,364 A | | 8/2000 | Paul |
| 6,398,726 B1 | | 6/2002 | Ramans et al. |
| 6,406,424 B1 | | 6/2002 | Williamson, IV et al. |
| 6,436,107 B1 | | 8/2002 | Wang et al. |
| 6,524,297 B1 | | 2/2003 | Newman |
| 6,837,883 B2 | | 1/2005 | Moll et al. |
| 7,885,434 B2 | | 2/2011 | Kitane et al. |
| 7,922,688 B2 | | 4/2011 | Bodduluri et al. |
| 7,962,192 B2 | | 6/2011 | Bodduluri et al. |
| 8,036,448 B2 | | 10/2011 | Gildenberg |
| 8,170,706 B2 | | 5/2012 | Coste-Maniere et al. |
| 9,364,171 B2 | | 6/2016 | Harris et al. |
| 2002/0082612 A1 | | 6/2002 | Moll et al. |
| 2002/0165434 A1 | | 11/2002 | Williamson, IV et al. |
| 2003/0060716 A1 | | 3/2003 | Heidrich |
| 2003/0109780 A1 | * | 6/2003 | Coste-Maniere ...... B25J 9/1671 600/407 |
| 2004/0186345 A1 | | 9/2004 | Yang et al. |
| 2006/0241414 A1 | | 10/2006 | Nowlin et al. |
| 2007/0106307 A1 | | 5/2007 | Bodduluri et al. |
| 2007/0230753 A1 | | 10/2007 | Kitane et al. |
| 2007/0293734 A1 | | 12/2007 | Coste-Maniere et al. |
| 2008/0097187 A1 | | 4/2008 | Gielen et al. |
| 2008/0146932 A1 | | 6/2008 | Chalana et al. |
| 2008/0167674 A1 | | 7/2008 | Bodduluri et al. |
| 2008/0247637 A1 | | 10/2008 | Gildenberg |
| 2008/0275396 A1 | * | 11/2008 | Neerken ............... A61B 8/0833 604/116 |
| 2010/0137880 A1 | | 6/2010 | Nahum et al. |
| 2010/0210934 A1 | | 8/2010 | Belson |
| 2010/0274202 A1 | * | 10/2010 | Hyde ............... A61B 5/150106 604/272 |
| 2011/0301500 A1 | | 12/2011 | Maguire et al. |

OTHER PUBLICATIONS

Non-Final Office Action in U.S. Appl. No. 13/335,700 dated Oct. 11, 2013.
Final Office Action in U.S. Appl. No. 13/335,700 dated May 7, 2014.
Non-Final Office Action in U.S. Appl. No. 13/335,700 dated Nov. 6, 2014.
Final Office Action in U.S. Appl. No. 13/335,700 dated Sep. 1, 2015.
Supplementary European Search Report in EP Application No. EP 11 85 0571 dated May 4, 2017.
Non-Final Office Action in U.S. Appl. No. 15/154,656 dated Jul. 1, 2016.
Non-Final Office Action in U.S. Appl. No. 15/154,656 dated Feb. 2, 2017.
Final Office Action in U.S. Appl. No. 15/154,656 dated Aug. 11, 2017.
European Examination Report in EP Application No. EP 11 850 571.8 dated May 28, 2018.

\* cited by examiner

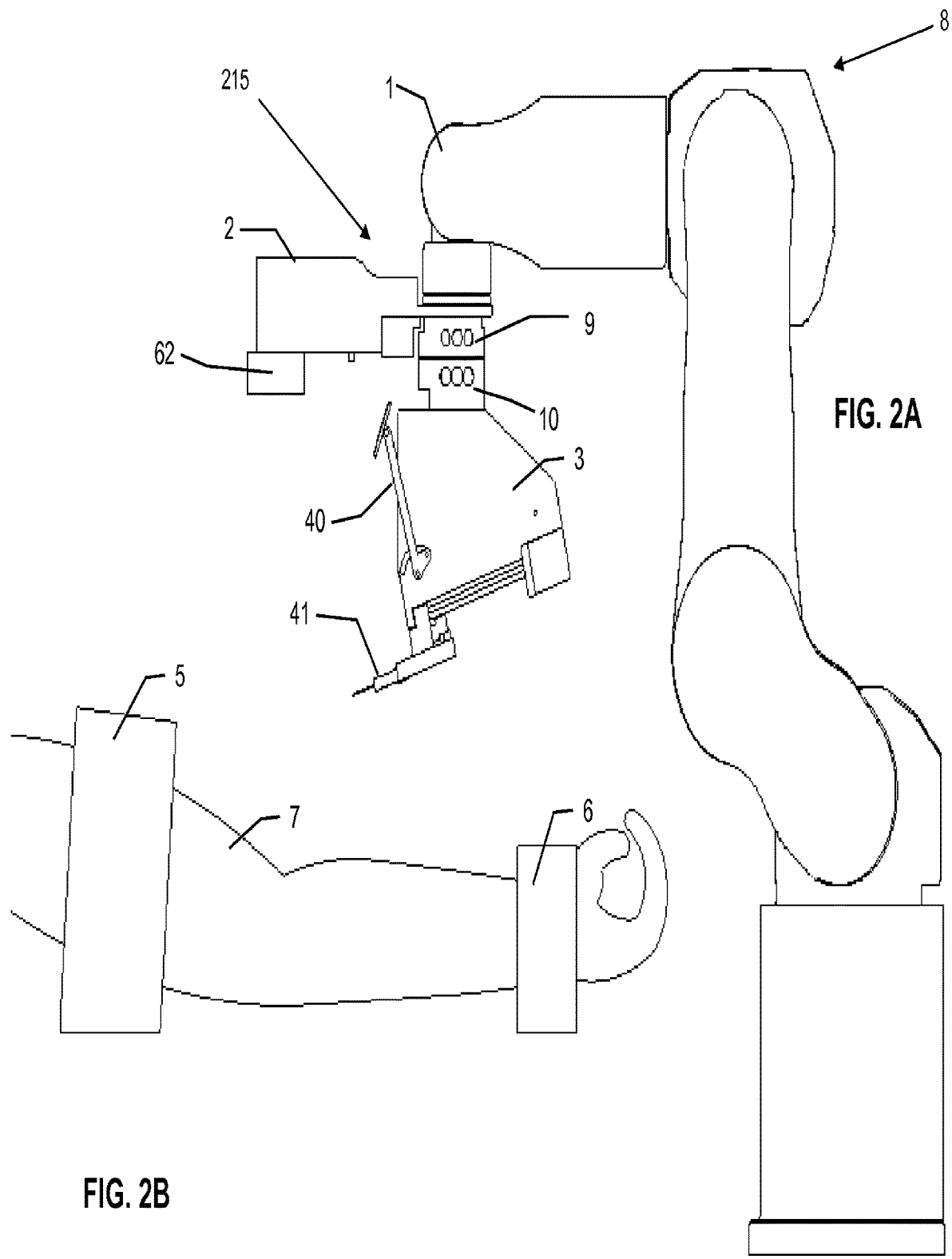

SYSTEMS AND METHODS FOR AUTONOMOUS INTRAVENOUS NEEDLE INSERTION

RELATED APPLICATIONS

This application is a continuation patent application of U.S. application Ser. No. 15/881,341, filed Jan. 26, 2018, which is a continuation patent application of U.S. application Ser. No. 15/154,656 filed on May 13, 2016, now U.S. Pat. No. 9,913,605, which is a divisional patent application of U.S. application Ser. No. 13/335,700 filed on Dec. 22, 2011, now, U.S. Pat. No. 9,364,171, which claims the benefit of and priority to U.S. Provisional Patent Application No. 61/426,022 filed on Dec. 22, 2010, the entirety of each of which is hereby incorporated herein by reference for the teachings therein.

FIELD

The embodiments disclosed herein relate to intravenous insertion systems, and more particularly to autonomous intravenous insertion systems and methods for using the system for autonomously inserting a needle or cannula into a vessel of a patient to be treated.

BACKGROUND

Intravenous needle and cannula insertion are mainstay procedures within modern medicine. They are essential components of both drug delivery and blood sampling for diagnostic purposes. Despite the fact that intravenous needle insertion, especially in forearm veins, is one of the most commonly practiced medical procedures, it is notorious for being an unmastered technique. Many patients are poked several times before the needle is successfully inserted and there is often great variability in adeptness among medical personal with regard to their needle insertion skills. Accordingly, there is a need to automate needle insertion to lessen the dependence on skilled technicians, decrease procedure time, and to reduce errors during intravenous needle and cannula insertion procedures.

SUMMARY

Systems and methods for autonomous intravenous needle insertion are disclosed herein. According to aspects illustrated herein, there is provided a system for autonomous intravenous insertion that includes a robot arm, one or more sensors pivotally attached to the robot arm for gathering information about potential insertion sites in a subject arm, a medical device pivotally attached to the robot arm, and a controller in communication with the sensors and the robot arm, wherein the controller receives the information from the sensors about potential insertion sites, and the controller selects a target insertion site and directs the robot arm to insert the medical device into the target insertion site.

According to aspects illustrated herein, there is provided a system for autonomous intravenous insertion that includes a robot arm, a plurality of sensors attached to the robot arm for gathering information about potential insertion sites in a subject arm, a medical device holding tool detachably engaged to the robot arm, the tool comprising a plurality of grippers for holding a medical device to be inserted into the subject arm, a first actuating mechanism for actuating the plurality grippers, stabilizing feet; and a second actuating mechanism for placing the stabilizing feet in the proximity to an insertion site, and a controller in communication with the plurality sensors, the medical device holding tool, and the robot arm, wherein the controller receives the information from the sensors about potential insertion sites, and selects a target insertion site and directs the medical device holding tool and the robot arm to insert the medical device into the target insertion site.

According to aspects illustrated herein, there is provided a method for autonomous intravenous insertion that includes securing a subject arm, identifying a target insertion site based on information received from at least one sensor, actuating a robot arm to deliver a medical device to the target insertion site, while monitoring the target insertion site, and inserting the medical device into the subject arm at the insertion site.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 2A and FIG. 2B are a schematic illustration of an embodiment of an autonomous intravenous insertion system of the present disclosure.

FIG. 4A, FIG. 4B and FIG. 4C illustrate various medical device holding tools for use with an autonomous intravenous insertion system of the present disclosure.

Figure 1:
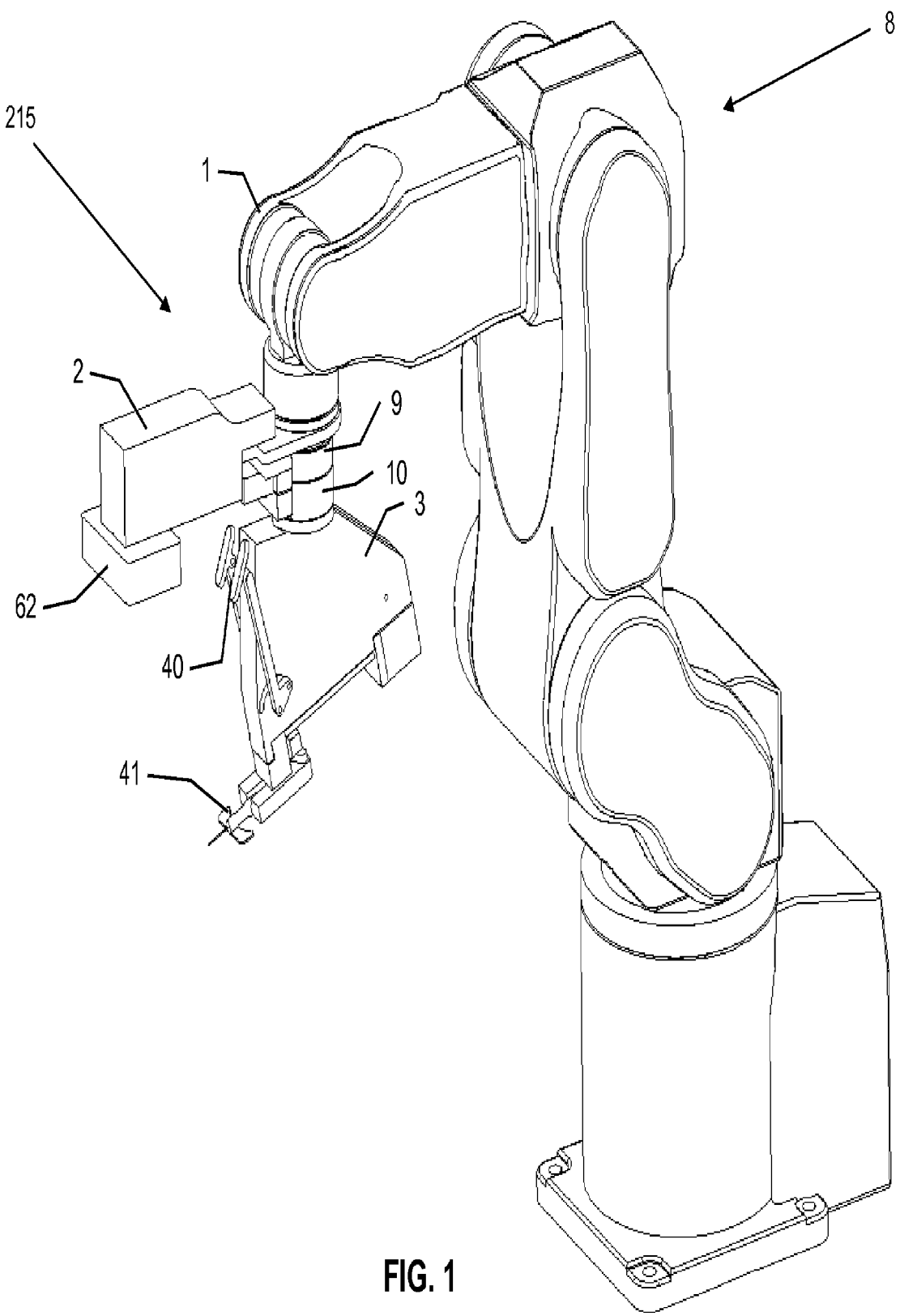
FIG. 1 is a perspective view of an embodiment of an autonomous intravenous insertion system of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Systems and methods for autonomous intravenous needle insertion are disclosed herein. In an embodiment, the systems disclosed herein act as autonomous intravenous needle insertion systems for inserting a medical device into a vessel of a patient during a medical procedure. In an embodiment, the systems disclosed herein act as autonomous intravenous needle insertion systems for inserting a medical device into a vessel of a patient during an insertion procedure. In an embodiment, the systems disclosed herein act as autonomous intravenous needle insertion systems for inserting a needle into a vein of a patient to be treated. In an embodiment, the systems disclosed herein act as autonomous intravenous needle insertion systems for inserting a cannula into a vein of a patient to be treated. In an embodiment, the systems disclosed herein act as an autonomous blood drawing system.

Subcutaneous vein-finding has been a subject of interest that has taken off in the past decade. The most prominent techniques used to identify veins thus far are infrared imaging and ultrasound signal processing. Infrared imaging is used to highlight the difference in contrast between a vessel and the surrounding skin when the region of interest is illuminated by infrared radiation. Ultrasonic systems are used to verify that a vein is indeed present under the surface of the skin where the ultrasound probe is deployed. Ultrasound may also be used to determine flow in a vessel using Doppler Shift analysis or it may be used to image veins underneath the skin.

The systems described herein can uniquely combine the infrared images with ultrasound images to highlight veins within these images based on shape, size, and orientation, among other characteristics. In an embodiment, the systems described herein are capable of selecting the most suitable vein for needle insertion based on various parameters including, but not limited to, location within the arm, size, orientation, and certainty of the selection being a vein. In an embodiment, the systems described herein track and localize the needle insertion site selected in real time so as to not lose the position of the needle insertion cite. In an embodiment, the systems described herein operate reliably and have built-in safety features so that the systems only operate under the circumstances appropriate for the medical procedure to be performed.

The autonomous intravenous needle insertion systems of the present disclosure are designed to take the place of a nurse or technician in the task of blood drawing and intravenous (IV) insertion. Other than for everyday phlebotomy or IV insertion on active patients, the autonomous intravenous needle insertion systems of the present disclosure can be used to administer drugs to subjects through syringes. In an embodiment, the autonomous intravenous needle insertion systems described herein can aid with needle insertion procedures required during surgery. Potential uses of the autonomous intravenous needle insertion systems of the present disclosure include, but are not limited to, automation of everyday phlebotomy procedures, aid with surgical procedures, carry out catheter insertion into a blood vessel, as part of a mobile robot with functionalities of a medical technician for care of soldiers or astronauts or other hard to reach workers needing immediate medical attention, for administering drugs to or gathering medical diagnostics from highly contagious or diseased patients, or in settings where it is not safe for medical personnel to travel, for instance as part of a rescue mission in the midst of biological warfare, and in a laboratory setting for automation of experiments involving injection.

Autonomous intravenous needle insertion systems may be advantageous for a number of reasons, including, but not limited to, minimizing the number of unsuccessful insertion attempts of a medical device into a vessel of a patient, and to lessen the dependence on skilled technicians and nurses in busy hospital environments as well as in the field, where such skills may be otherwise unavailable. In addition to these advantages in a hospital or office setting, the autonomous intravenous needle insertion systems of the present disclosure also may be utilized in less conventional settings, including, but not limited to, research and laboratory settings necessitating many needle insertion procedures to be carried out simultaneously or after short intervals of time on one or more persons, or insertion in an unsafe environment, settings involving highly contagious or diseased patients, or other such settings where needle insertion is needed but it is unsafe for medical technicians or personnel (for instance a rescue mission in the midst of biological warfare), and settings where it is not practical for medical technicians to go, such as a battlefield, an airplane, or outer space.

Generally speaking, the medical procedure for drug delivery or blood sampling includes the following steps: 1) gathering the appropriate apparatus for the procedure; 2) locating an insertion site by visual inspection and/or palpation; 3) carrying out the procedure; 4) discarding insertion apparatus and disposable paraphernalia that is not needed following the procedure. The autonomous intravenous needle insertion systems of the present disclosure are capable of accomplishing these tasks autonomously, while mimicking human activity on many levels. The autonomous intravenous needle insertion systems of the present disclosure are also capable of being operated by a medical technician, nurse, or doctor, in the event they wish to do so.

The medical procedure for drug delivery or blood sampling involves more than just inserting a needle into a patient's vessel. In the case of drawing blood with VACU-TAINER® equipment, the procedure involves inserting the needle, engaging the vacuum tubes, disengaging the tubes after they are filled, and replacing a filled tube with another empty tube when multiple specimens are needed. To that end, the autonomous intravenous needle insertion systems of the present disclosure include a device to handle tube engagement, disengagement, and new tube reengagement at the tail end of the VACUTAINER® needle device. In the case of cannula insertion, the needle must be extracted from the in-dwelling catheter surrounding it, leaving the cannula in place to administer drugs or to draw blood. To that end, the autonomous intravenous needle insertion systems of the present disclosure include a needle extraction mechanism.

In addition, there are other ancillary procedures involved in needle or cannula insertion. For example, when a technician draws blood, the technician uses a tourniquet to build up pressure in the vessel, and when the technician has finished drawing blood, the tourniquet is released. The technician also applies pressure to the site after removing the needle in order to prevent bleeding. In the case of IV cannula insertion, the insertion site and catheter are dressed following insertion in order to prevent contamination and dislodgement of the catheters. The autonomous intravenous needle insertion systems of the present disclosure are capable of handling such ancillary procedures related to the medical procedure at hand. At the start of the procedure, an automatic tourniquet device serves the dual purpose of ordinary tourniquet function and as an arm stabilizer.

FIG. 1 and FIG. 2A illustrate an embodiment of an autonomous intravenous insertion system 8 of the present disclosure, having an insertion module 215 attached to a robot arm 1. In an embodiment, the insertion module 215 includes a main sensor assembly 2, shown only with a near-infrared light source 62, a butterfly needle 41 and a medical device holding tools. Exemplary medical device holding tools include a needle tool 3 for drawing blood and a catheter tool 4 (not shown) for inserting catheters into the subject. Various tools and sensors of the insertion module 215 may be attached to the robot arm 1 by means known and used in the art. In an embodiment, a tool changer system having a male tool changer 9 and a female tool changer 10 is used for connecting medical device holding tools, such as the needle tool 3 or catheter tool 4, to the robot arm 1.

In an embodiment, the robot arm 1 is programmable to actuate medical device holding tools to insert and extract needles or catheters via medical device holding tools attached to the end of the robot arm 1. In an embodiment, medical device holding tools of the present disclosure include the needle tool 3 for handling blood drawing equipment and catheter tool 4 for catheter manipulation. The robot arm 1 also travels to docking positions that vary according to the procedure to be performed. Each contemplated medical device, such as a butterfly needle 41, has it own automatic loading mechanisms to append the device onto the tool designed to manipulate it. In an embodiment, the needle tool 3 appends a butterfly needle 41 to its end effector autonomously with help of an automatic butterfly needle dispenser 11. Once the butterfly needle 41 is appended to the needle tool 3, the three-dimensional spatial coordinates along with the orientation of the selected vein are determined, and the robot arm 1 moves the butterfly needle 41 to that position for insertion. After the procedure is performed, the robot arm 1 travels to an unloading position in order to discharge the used medical device.

In an embodiment, the robot arm 1 is computer controlled and is designed to autonomously guide a medical device to a patient's vessel for the automatic insertion of the medical device into the patient's vessel. In an embodiment, the robot arm 1 may include a high-precision mechanical positioning system and a control unit. In an embodiment, the control unit is a dedicated computer and motor driver that takes commands from the master computer 90 and controls the robot's position and motion. An emergency stop switch 13 may be present in case of system malfunction, allowing immediate cessation of the motion of the robot arm 1. The motion of the robot arm 1 may also be immediately stopped through the controlling software, if desired. If the robot arm 1 is stopped in either of these ways, it may retreat to its original home position. In an embodiment, the robot arm 1 may be provided with capability to hold its present position, while allowing someone to manipulate its joints with ample force may also be included. In an embodiment, as an additional safety feature, the robot arm 1 does not move as a result of gravitational forces. In an embodiment, the robot arm 1 is a mobile robot capable of avoiding obstacles and path following so that the system 8 can autonomously move around a hospital room or floor.

In an embodiment, a pneumatic system 94 is connected to the robot arm 1 to provide controlled air pressure to end-effectors at the end of the robot arm 1 through tubes that reach from the base of the robot arm 1 to the manipulator end. In an embodiment, the tool changers 9 and 10, the needle tool 3, the catheter tool 4, and a disposal unit 96 all use pneumatic actuation. In an embodiment, the pneumatic system 94 includes a small compressor and storage tank, and a series of computer-controlled valves used to operate various pneumatic actuators used in the end effectors.

In an embodiment, pneumatic actuators are used to grip medical devices, such as butterfly needles 41, catheters 22, and other medical devices. In an embodiment, butterfly needles 41 or catheters 22 are attached to the needle tool 3 or the catheter tool 4, respectively, for facilitation of the insertion procedure. In an embodiment, other devices may be used to assist with the medical procedure to be performed in conjunction with the insertion procedure, including vacuum tubes for blood drawing, a medication administration device, or other diagnostic or therapeutic devices, including, but not limited to, blood drawing equipment, syringes, medication pumps, intravenous solution bags, or combinations thereof. In an embodiment, the medical device to be manipulated is a VACUTAINER® butterfly needle 41. In an embodiment, the medical device to be manipulated is a catheter 22. In an embodiment, the butterfly needle 41 or catheter 22 may be attached to the complementary device for facilitating a medical procedure to be performed in conjunction with the insertion procedure.

FIG. 2B illustrates a patient's arm 7 cuffed inside an automatic tourniquet cuff 5 and wrist stabilizing cuff 6, which can be used to increase the visibility of veins and stabilize the patient's arm 7 during the procedure. Both the automatic tourniquet cuff 5 and wrist stabilizing cuff 6 are pressurized with air after the patient's arm 7 is placed through the cuffs 5 and 6. In an embodiment, the automatic tourniquet cuff 5 serves as an ordinary tourniquet, that is, it increases vessel size and visibility which ultimately aids with the vein identification procedure. In an embodiment, together with the automatic tourniquet cuff 5, the wrist stabilizing cuff 6 serves as a rest and a demobilizer for the patient's forearm to simplify the tracking of the target vessel. In an embodiment, a barcode reader 216 is added near the wrist stabilizing cuff 6 that would read a patient's bracelet barcode in order to collect patient data for the procedure. If not wearing a wristband, patients might enter their information into the touch screen user interface. In an embodiment, the automatic tourniquet cuff 5 and wrist stabilizing cuff 6 are positioned on a flat surface.

Figure 3A:
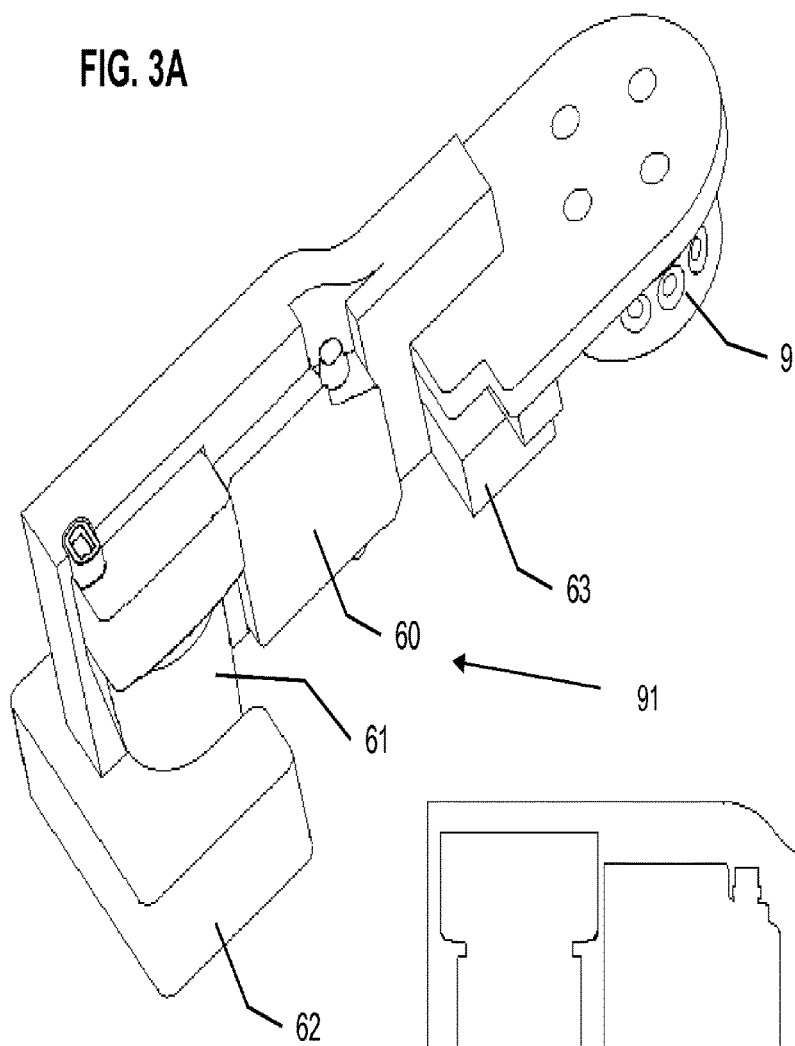
FIG. 3A and FIG. 3B illustrate an embodiment of a sensor assembly for use with an autonomous intravenous insertion system of the present disclosure.
Figure 3B:
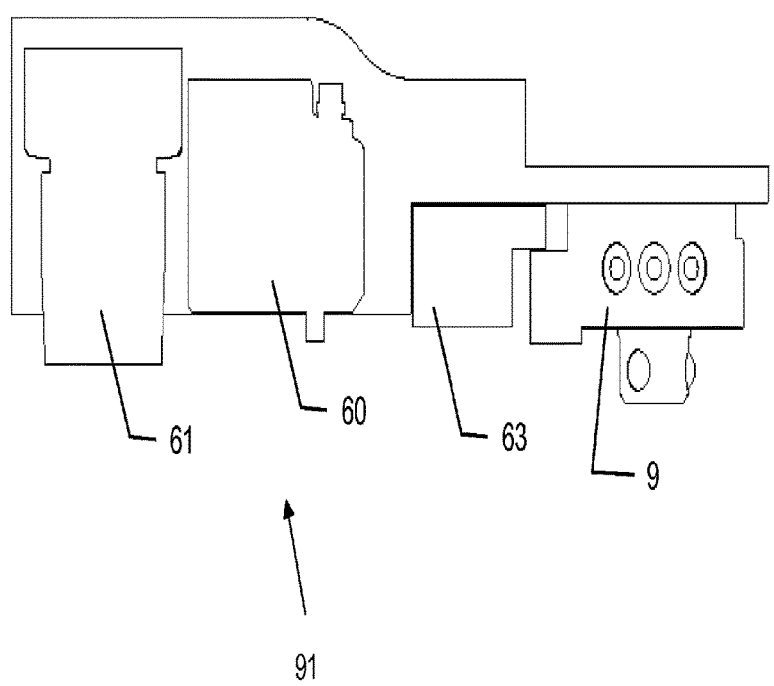

FIG. 3A and FIG. 3B show an embodiment of the main sensor assembly 2 used to find appropriate insertion sites on the patient's arm 7. In an embodiment, the main sensor assembly 2 is permanently attached to the robot arm 1 and is not designed to be changed out routinely. In an embodiment, the main sensor assembly 2 includes one or more sensory units or primary sensors 91, such as a laser rangefinder 60, a near-infrared (NIR) camera 61 and a near-infrared (NIR) light source 62. The main sensor assembly 2 may also include an ultrasound device 64 (not shown in FIG. 3A or FIG. 3B). The main sensor assembly 2 may also include miniature solenoid valves 63 for control of pneumatic devices and the male tool changer 9, which is used for connecting medical device holding tools to the robot.

In an embodiment, one or more of the primary sensors 91 may be rigidly mounted on the robot arm 1 in a fixed relation to the butterfly needle 41. In other words, if the butterfly needle 41 pivots, the one or more primary sensors 91 pivot with the butterfly needle 41. In an embodiment, one or more of the primary sensors 91 may be positioned at a stationary vantage point. In an embodiment, the one or more primary sensors 91 provide positioning information to the control unit of the system 8, allowing the autonomous intravenous insertion system 8 to recognize potential insertion sites and their locations and orientations in the coordinate system of the robot arm 1.

One of the primary sensors 91 in the main sensor assembly 2 comprises an imaging unit, such as a CMOS, CCD, or other similar camera coupled with a bandpass filter used to isolate a near-infrared (NIR) frequency range. This imaging device is referred to throughout this document as an NIR camera 61. In an embodiment, the NIR frequency range is a narrow frequency range. In an embodiment, the wavelength range used by the system to distinguish the patient's vessel from the environment surrounding the vessel comprises a range from about 720 nanometers to about 780 nanometers. It should be noted that other NIR wavelength ranges may be used without departing from the spirit and scope of the presently disclosed embodiments. It should also be noted that other medical imaging techniques can be employed by the system to highlight a patient's vessel in contrast to the environment surrounding the patient's vessel.

In an embodiment, the one or more primary sensors 91 comprise an NIR camera 61 for determining the three-dimensional coordinates of the vessel of the patient receiving the medical procedure. In an embodiment, the NIR camera 61 can be used to determine an optimal orientation for insertion of a medical device into the vessel of the patient. In an embodiment, the NIR camera 61 may provide relative location in two dimensions, as well as the orientation of the targeted vessel relative to the current position of the butterfly needle 41 at the distal end of the robot arm 1, so that the butterfly needle 41 may be aligned with the targeted vessel to ensure a safe insertion procedure.

In an embodiment, the autonomous intravenous insertion system 8 may use multiple NIR cameras 61 capable of seeing different frequency ranges in order to better eliminate false vein images from appearing to be valid ones. In an embodiment, multiple NIR cameras 61 can provide a grayscale color image and a NIR image, which can be stitched together, and pixel values of target sites in the NIR image can be compared to corresponding pixels in the grayscale color image. Because NIR-only cameras pick up vein contrast better than white light cameras, it is expected that the comparison of the two images containing different frequency representations of the insertion region may lead to an image with data containing information about the location of potential veins. More specifically, true veins may have substantially darker pixel values in the NIR image than they will in the grayscale white light image. Analysis of these comparisons can lead to less false positives and therefore more accurate target site selection.

In an embodiment, the one or more primary sensors 91 comprise a laser rangefinder 60 to determine the distance of the butterfly needle 41 to the patient's vessel. In an embodiment, the laser rangefinder 60 can be used to determine the topography of the selected insertion site. The laser rangefinder 60 can be mounted on the robot arm 1 in a fixed relation to the insertion needle. In an embodiment, the laser rangefinder 60 is designed to operate in conjunction with the NIR camera 61 to track the three-dimensional coordinates and orientation of a patient's vessel in real-time to identify an optimal insertion path for inserting a medical device into the vessel. In an embodiment, the laser rangefinder 60 is designed to operate in conjunction with the NIR camera 61 to enable the robot arm 1 of the system 8 to guide a medical device attached to the robot arm 1 along the optimal insertion path to autonomously insert the medical device into the vessel. In an embodiment, the laser rangefinder 60 and the NIR camera 61 work together to determine the three-dimensional coordinates and orientation of the patient's vessel so that the primary actuators 93 can guide the medical device to be inserted into the patient's vessel to the three-dimensional coordinates of the vessel for insertion of the medical device into the vessel.

In an embodiment, the laser rangefinder 60 comprises a high-precision laser rangefinder. The laser rangefinder 60 uses a laser beam to determine the distance to the vessel. The laser rangefinder 60 determines the distance to the vessel by sending a laser pulse in a beam towards the vessel and measures the time it takes for the pulse to be reflected off of the vessel and for the pulse to return to the rangefinder. In an embodiment, the laser rangefinder 60 can be used to determine other distances useful for determining the three-dimensional coordinates of the vessel or the orientation of the vessel, including, but not limited to the distance to the patient's arm 7, for example. The distance to the target the laser rangefinder 60 is pointing at (the z coordinate in the robot frame of reference) enables the user to determine the x and y coordinates in the robot frame of that same target as identified in the two-dimensional video frame from the camera NIR 61. Thus, the user can be provided with a three-dimensional point in space whereby the user can direct the movement of the robot arm 1 to a desired site. In an embodiment, the laser rangefinder 60 is also used to obtain the relative topography of the insertion site, so the robot arm 1 positions itself in a way that the insertion path is not obstructed in any way by the patient's arm 7.

In an embodiment, the primary sensors 91 further include an ultrasound device 64 (having one or more ultrasound transducers) for acquiring an ultrasound image of the vessel of the patient receiving the medical procedure. In an embodiment, the ultrasound device 64 can be manually operated by the user of the autonomous intravenous insertion system 8 of the present disclosure to acquire the ultrasound image of the patient's vessel to verify the existence of the patient's vessel before insertion of the medical device into the patient's vessel. In an embodiment, the ultrasound device 64 can be integral with and operated autonomously by the system 8 to acquire the ultrasound image of the patient's vessel to verify the vessel's existence before the medical device is inserted into the patient's vessel by the actuator.

In an embodiment, the ultrasound device 64 may serve as the primary imaging unit in a case where the system 8 has determined that the patient has obscure veins. In this case, the ultrasound device 64 may be deployed to image veins and determine a location of a suitable insertion site so that the autonomous intravenous insertion system 8 can command the actuator to insert a butterfly needle 41 in that site. In an embodiment, the ultrasound device 64 can be manipulated by a separate ultrasound manipulation unit that is appended to the robot arm 1. In an embodiment, the ultrasound device 64 can be built into the needle tool 3 or catheter tool 4.

In an embodiment, the autonomous intravenous insertion system 8 may, among other functions, 1) autonomously handle and use an ultrasound device 64 to verify that a target is indeed a vein as well as to track a vein's position underneath the skin, 2) use haptic feedback for safely handling the ultrasound device 64 on the subject's skin, 3) use haptic feedback to "feel" the presence of a vessel underneath the skin, 4) use haptic feedback to distinguish between a successful and an unsuccessful needle penetration, incorporate a blood pressure and temperature measurement system to give the robot more "nurse-like" functionality, 5) include a NIR camera 61 aimed at the patient to monitor their reaction to the medical procedure, in case the patient has an unexpected reaction, may enable the user to have direct control of robot arm 1 movement without manually moving it such as by tele-operation of the robot arm 1, or any combination thereof.

In an embodiment, the autonomous intravenous insertion system 8 may be provided with the capability to enable the ultrasound device 64 combined with haptic feedback to be autonomously or remotely manipulated. Useful features are tracking targeted tissue underneath the skin's surface in real time, following a catheter 22 path along the body, or following some other medical tool being used underneath the patient's skin. This technology may be considered helpful in many cases, such as in aiding a doctor or other medical personnel for (1) catheter guidance, (2) visual enhancement of surgical tool use underneath the skin, (3) tracking tissues to better aim radiation equipment during radiation therapy.

The one or more primary sensors 91 may be used in the present configuration to detect the presence of subcutaneous veins underneath the skin. The underlying purpose of these primary sensors 91 is to obtain the whereabouts and orientation of a targeted vessel as quickly as possible. To that end, various embodiments of the autonomous intravenous insertion system 8 of the present disclosure may include more than three units as described above and/or other sensory units such as various near-infrared or red laser diodes, or some other handheld vein-imaging system known in the art in addition or instead of the ones described above to reliably detect the presence and orientation of targeted vessels underneath the skin.

In an embodiment, the present disclosure includes a means of controlling ambient light. Lighting detection, in an embodiment, may be carried out by a combination of (1) image brightness analysis, (2) IR phototransistors, and (3) photodetectors. The lighting system includes a number of infrared LEDs and/or a shielder for blocking room lights from interfering with the NIR camera 61. The software can control camera settings in combination with the brightness of the NIR LEDs to prevent the presence of light or dark spots. Diffuse lighting is imperative for eliminating shadows generating an accurate image of veins in the patient's arm 7. This system will be controlled by the master computer 90 based on the video input from the NIR camera 61, so as not to confuse or complicate the operation of the system.

Figure 4B:
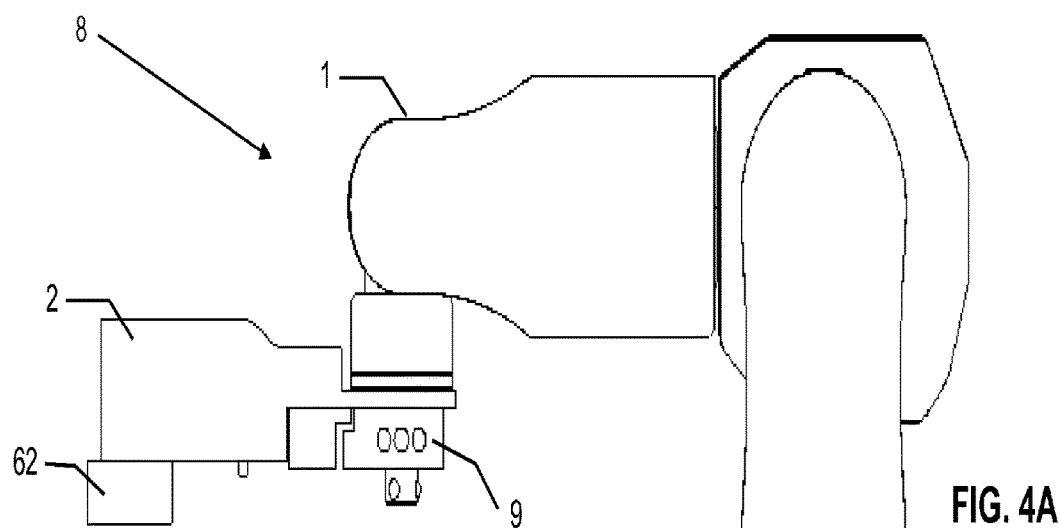
Figure 4C:
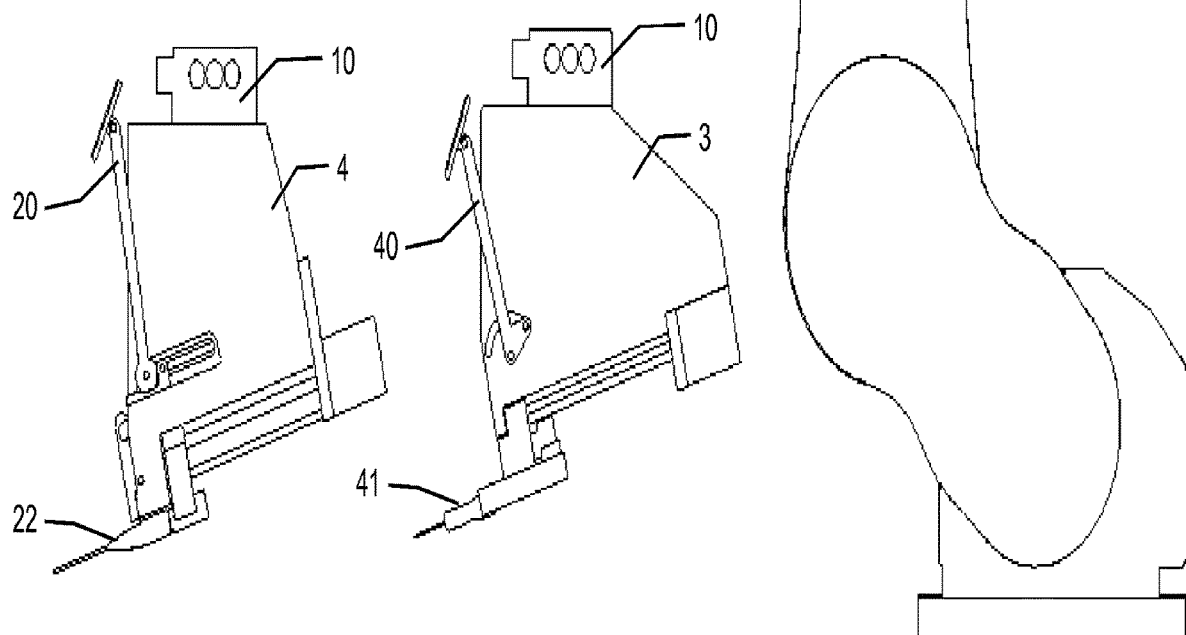

FIG. 4A depicts the robot arm 1 and FIG. 4B and FIG. 4C depict two medical device holding tools 212, needle tool 3 and catheter tool 4. These tools can be attached to the robot arm 1 using the tool changer systems 9 and 10. Needle tool 3 is shown for manipulating butterfly needles 41, while the catheter tool 4 is used for inserting catheters 22. Also depicted are stabilizer feet 20 and 40, both of which are used for stabilizing the subject arm 7 during procedures.

In an embodiment, automatic tool changer systems 9 and 10 are fixed to the robot arm 1, enabling the system 8 to autonomously affix tools to manipulate end-effectors for a desired medical procedure. These tools pick up and manipulate the medical devices 22 and 41 mentioned above during insertion procedures. For example, the robot arm 1 might connect to a tool designed to pick up a certain type of butterfly needle 41, as shown in FIGS. 10-14, or a certain type of catheter 22, as shown FIGS. 5-9. In an embodiment, the system 8 includes a needle gripper assembly 200 for holding the butterfly needle 41 in place. In an embodiment, the system 8 includes a catheter gripper 21 for holding the catheter 22 in place.

Figure 5:
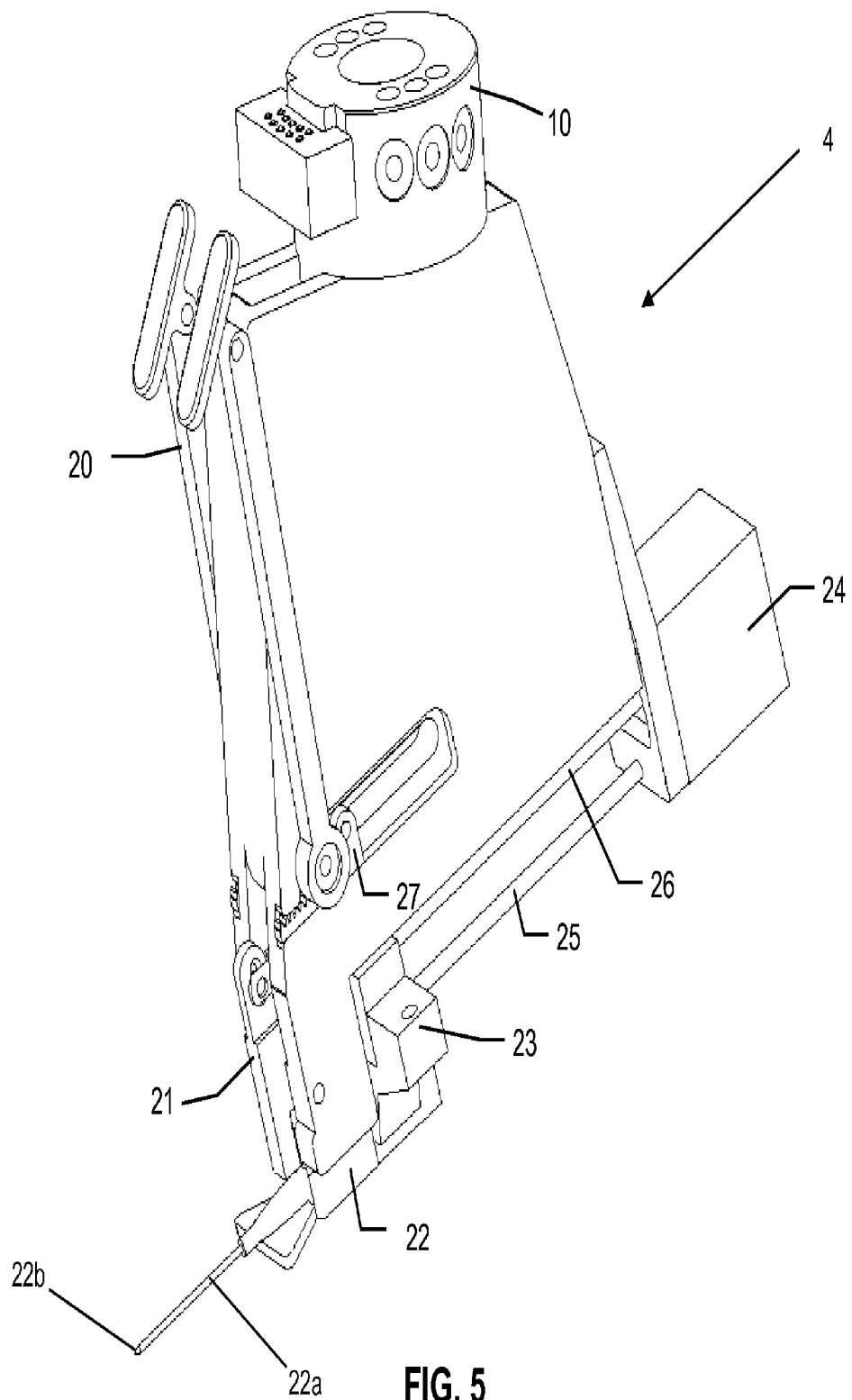
FIG. 5 illustrates an embodiment of a catheter tool of the present disclosure for holding a catheter.

FIG. 5 is a perspective view of an embodiment of the catheter tool 4. Atop the unit is the female part of the tool changer 10 which allows the primary actuator to append this unit. In the depicted embodiment, the catheter tool 4 holds a 2-piece catheter 22 using a custom gripper having a catheter gripper 21 and a gripper finger 23. In an embodiment, the catheter 22 is stationary with respect to the catheter tool 4. In an embodiment, the catheter 22 is a standard medical device including a butterfly catheter 22a and a retractable central needle 22b. The retractable central needle 22b stiffens the butterfly catheter 22a during insertion, and is retracted after insertion is complete. The butterfly catheter 22a is held by a catheter gripper 21 while the retractable central needle 22b is held separately by a gripper finger 23 attached to a gripper body 29. The gripper finger 23 and the gripper body 29 can be referred to collectively as the central needle gripper 23, 29. In an embodiment, the gripper body 29 can be moved along a guide rail 25 by a stepper motor 24 and a lead screw 26, which also causes the gripper finger 23 to move. In an embodiment, the catheter tool 4 includes stabilizer feet 20, which are shown in FIG. 4 in their resting, upright position. The stabilizer feet 20 are used for stabilizing the patient's arm 7 during procedures.

Figure 6:
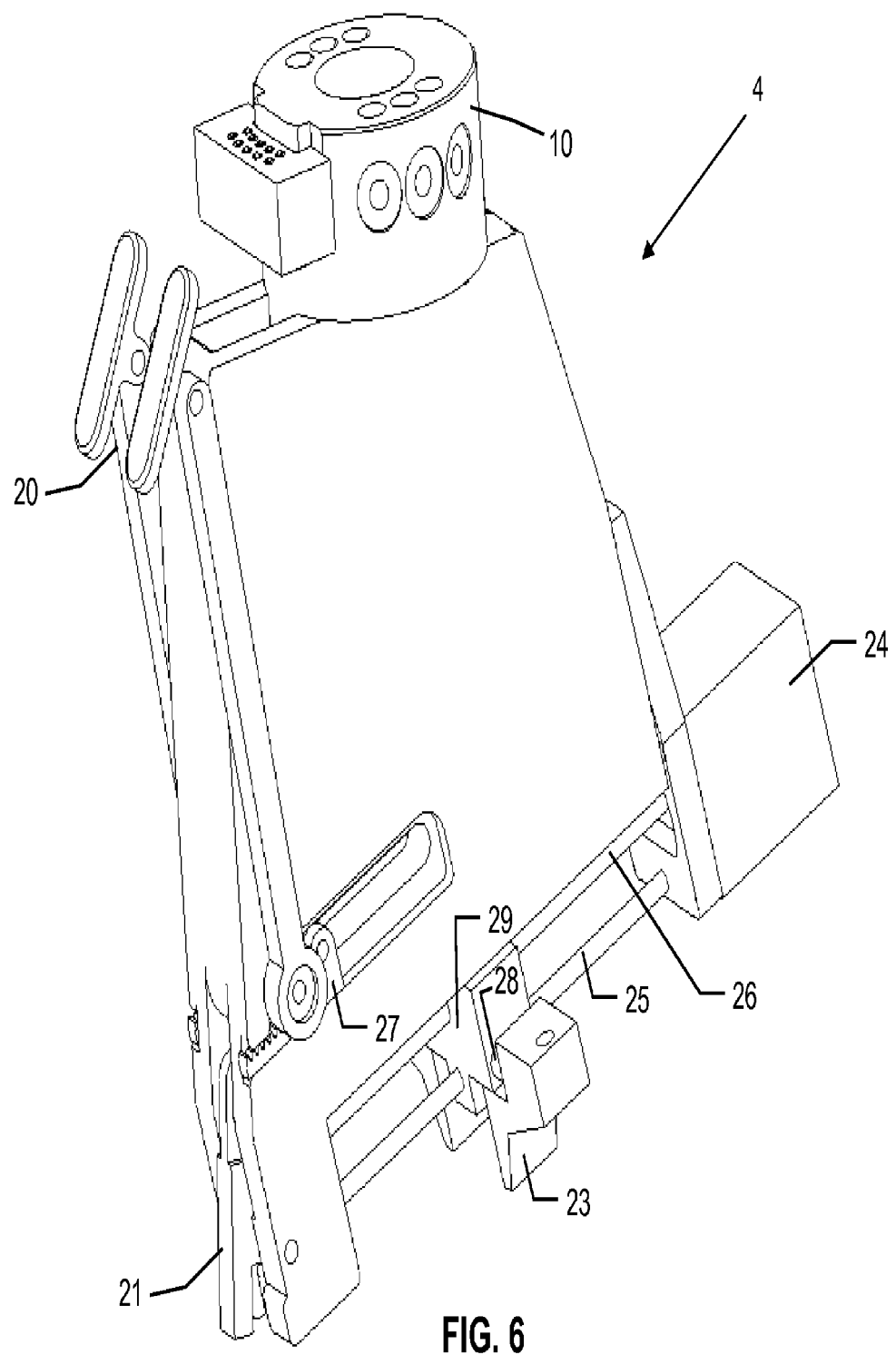
FIG. 6 illustrates an embodiment of a catheter tool in its initial state, without a catheter.

In FIG. 6, the embodiment of the catheter tool 4 in FIG. 5 is depicted with all grippers open and the central needle gripper 23, 29 retracted partway. The stabilizer feet 20 are shown in their resting, upright position.

Figure 7:
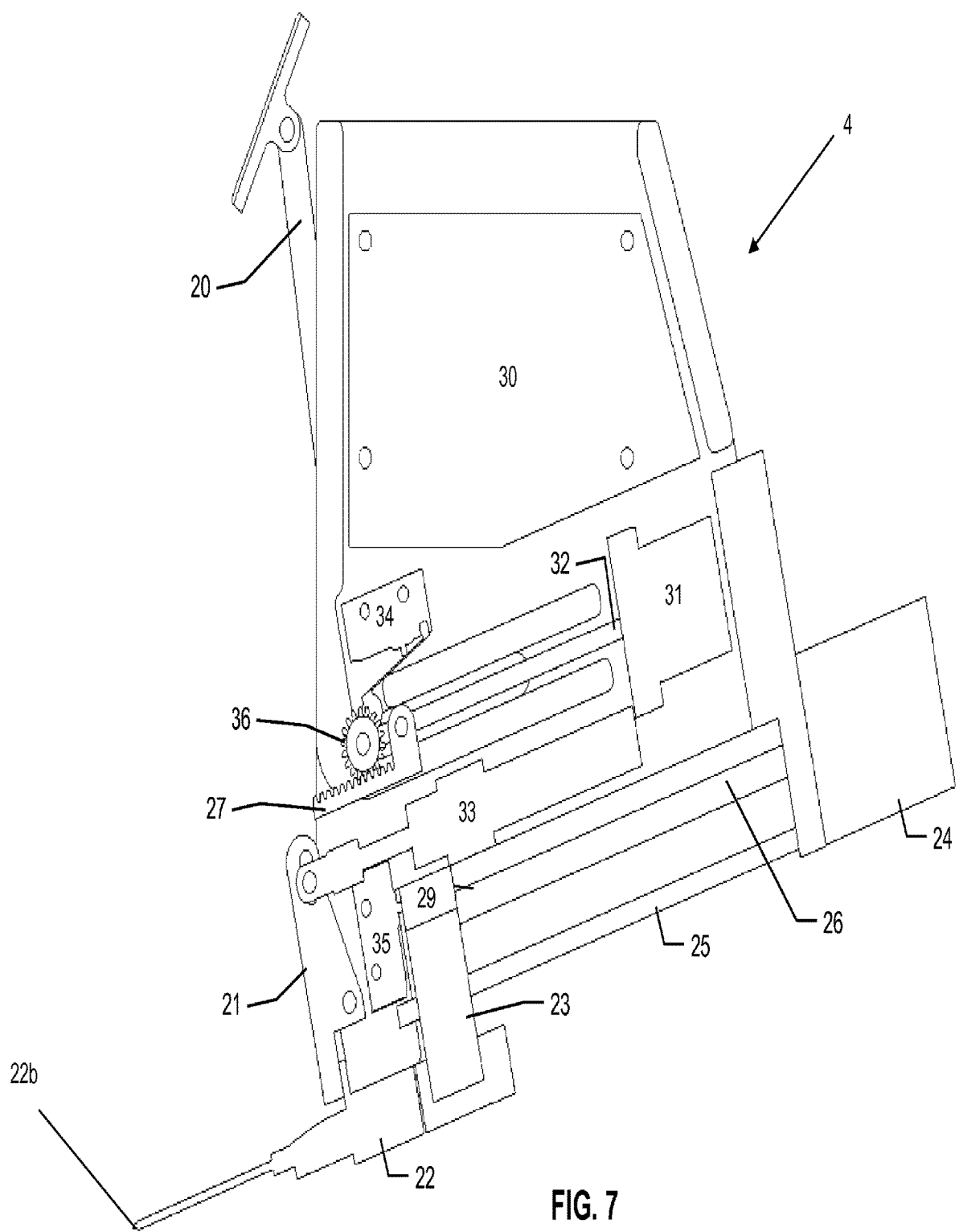
FIG. 7, FIG. 8, FIG. 9, and FIG. 10 are cutaway views of an embodiment of a catheter tool at various stages of a catheter insertion procedure.

FIG. 7 shows a cutaway view of the embodiment of the catheter tool 4 of FIG. 5 in its initial state. The catheter tool 4 is designed to grip a catheter 22 and to pull the retractable central needle 22b out of the butterfly catheter 22a once it is inserted. The catheter tool 4 is equipped with stabilizer feet 20 to anchor the target insertion vessel while the insertion procedure is underway. The stabilizer feet 20 are shown in the raised position, which can be achieved by turning the stepper motor 31 to turn a lead screw 32. In an embodiment, the lead screw 32 moves a gear rack 27 and the axle of a stabilizer foot spur gear 36 forward until the spur gear 36 reaches the end of the lead screw 32, where it stops. The gear rack 27 continues moving closer to the spur gear 36, causing the spur gear 36 to rotate. Stabilizer feet 20 are connected to the hub of the spur gear 36, so the stabilizer feet also rotate up as spur gear 36 rotates due to the movement of the gear rack 27. In FIG. 7, the spur gear 36 is all the way forward and rotated. In an embodiment, the axle of the spur gear 36 is threaded but is not engaged on the threads of the lead screw 32. A roller type limit switch 34 may be activated when the spur gear 36 needs to move backwards. FIG. 7 also shows a control circuit 30, which commands the various functions of the catheter tool 4, and a plunger type limit switch 35, which is responsible for preventing out-of-range motion of the rear grippers 23 and 29. It should be noted that other types of limit switches can be used instead of the roller type limit switch and plunger type limit switch. In an embodiment, a pneumatic cylinder 33 controls the front catheter gripper 21, and the miniature pneumatic cylinders 28 control a central needle gripper 23, 29. As shown in FIG. 7, the catheter 22 is gripped in grippers with the retractable central needle 22b still inside and ready for insertion.

Figure 8:
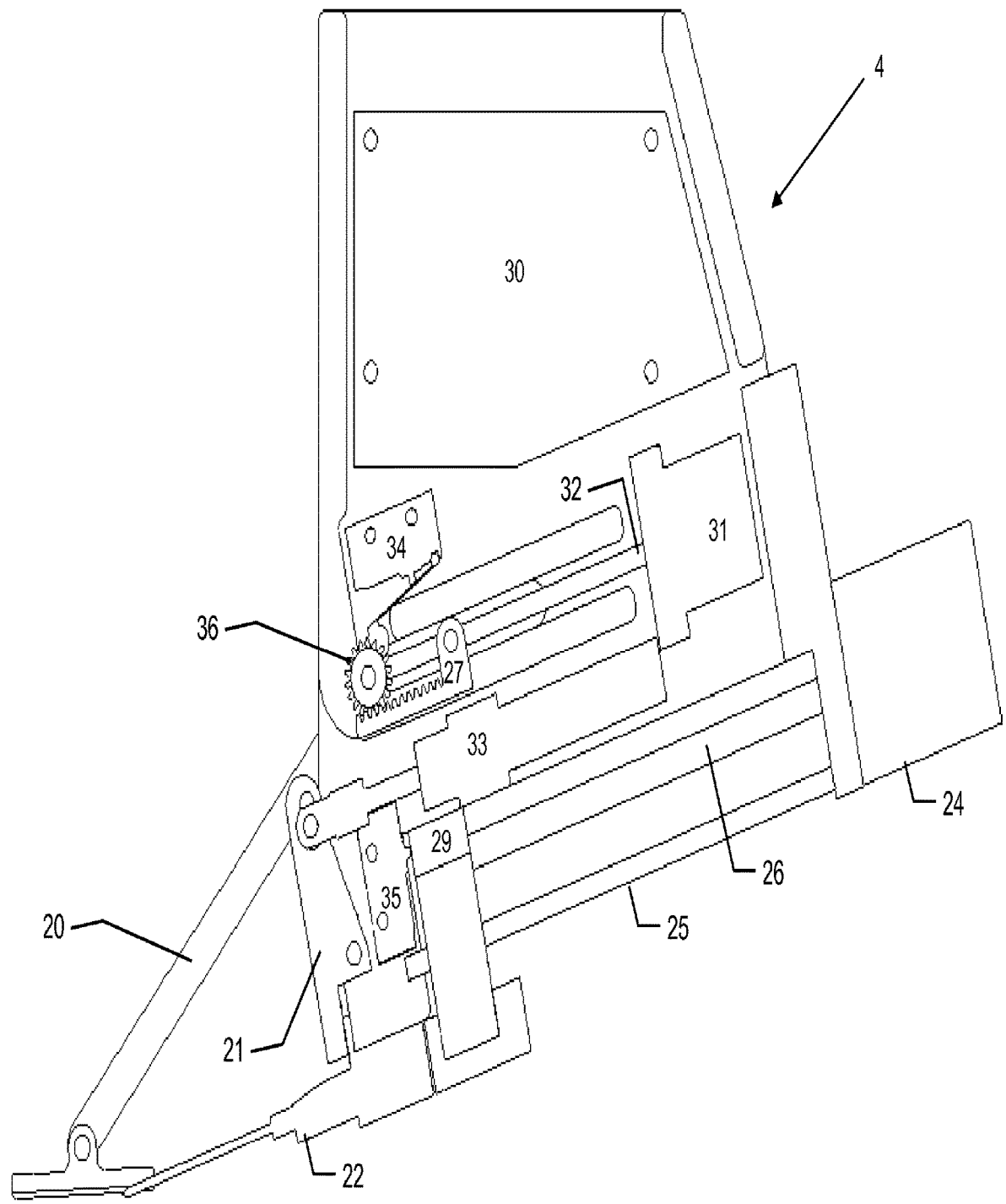

FIG. 8 shows a cutaway view of the next step in the insertion procedure utilizing the embodiment of the catheter tool 4 of FIG. 5, where the stabilizer feet 20 drop down and apply pressure around the insertion site. The lead screw 32 is shown turned by the stepper motor 31 such that the threaded gear rack 27 is moved backward. The motion of the gear rack 27 backward relative to the spur gear 36 causes the stabilizer feet 20 to swing down and press on the patient's arm 7 in proximity to an insertion site. In an embodiment, the spring in the roller type limit switch 34 prevents the spur gear 36 from engaging the threads of the lead screw 32 until the stabilizer feet 20 begin pressing on the patient's arm 7. Once the spur gear 36 can no longer rotate, the backward motion of the gear rack causes the spur gear 36 to move backward as well, where it engages the threads of the lead screw 32 and presses the roller type limit switch 34. When the spur gear 36 is engaged on the threads of the lead screw 32, turning the lead screw 32 causes the stabilizer feet 20 to move along the axis of the lead screw 32.

Figure 9:
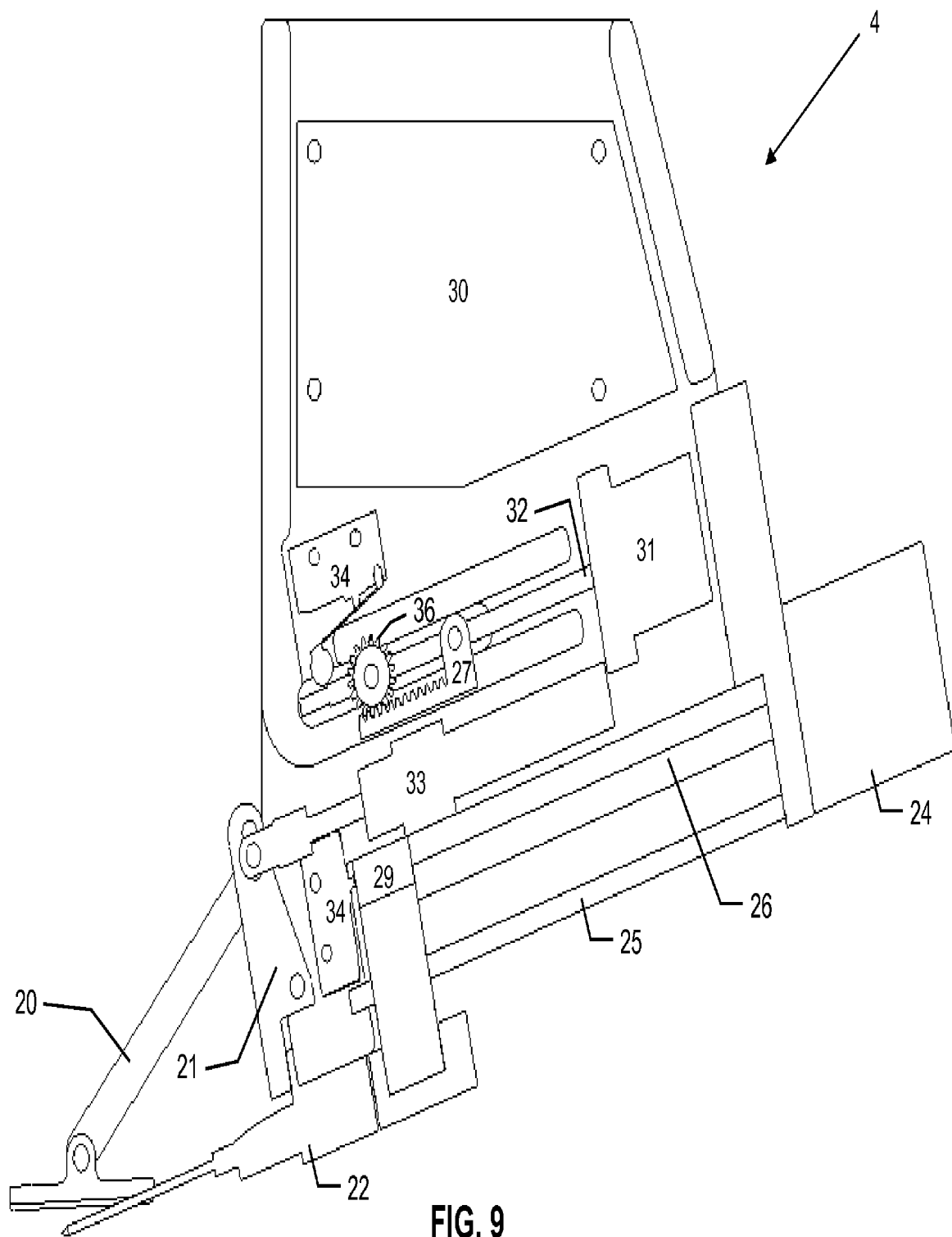

FIG. 9 shows a cutaway view of the embodiment of the catheter tool 4 of FIG. 5 after the catheter 22 has been inserted in a vein. The stabilizer feet 20 are shown in the lowered position and moved backwards to match the forward motion of the robot arm 1 that inserts the catheter 22 into the patient's arm 7. In an embodiment, the speed of the gear rack 27 and spur gear 36 along the lead screw 32 matches the insertion speed of the robot arm 1 (in the opposite direction), so that the stabilizer feet 20 remain stationary relative to the patient's arm 7, while the butterfly catheter 22a is inserted.

Figure 10:
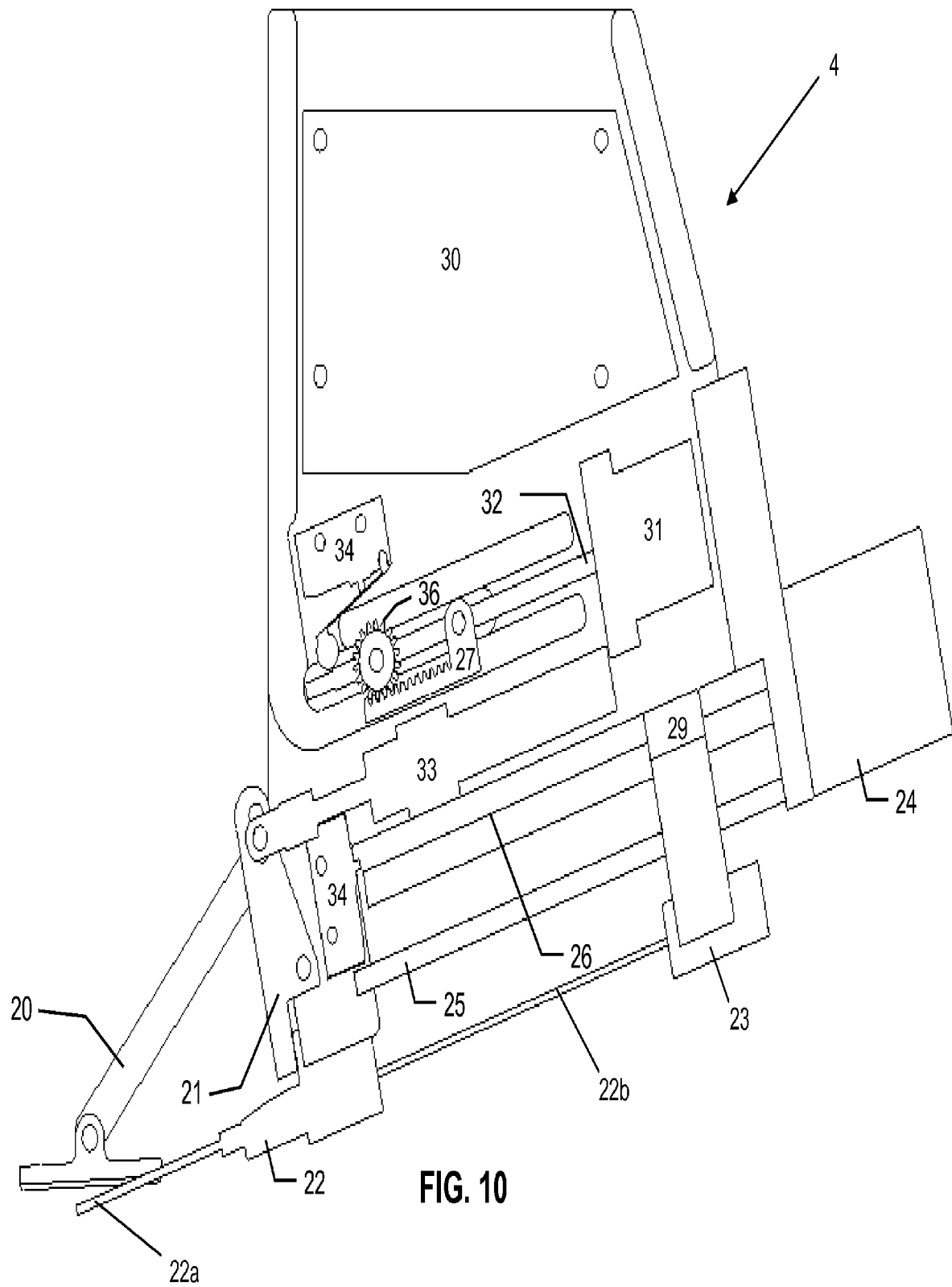

FIG. 10 shows a cutaway view of the embodiment of the catheter tool 4 of FIG. 5 in the next step of the insertion procedure, where the retractable central needle 22b is retracted from the butterfly catheter 22a. In an embodiment, the stepper motor 24 turns a lead screw 26, causing the threaded gripper body 29 to slide along the guide rail 25. As the gripper body 29 is being retracted, the gripper body pulls the gripper fingers 23 backwards, which in turn pulls the retractable central needle 22b with it. At this point, the butterfly catheter 22a can be released by the catheter gripper 21, and left in the patient's arm 7 for further procedures.

Figure 11:
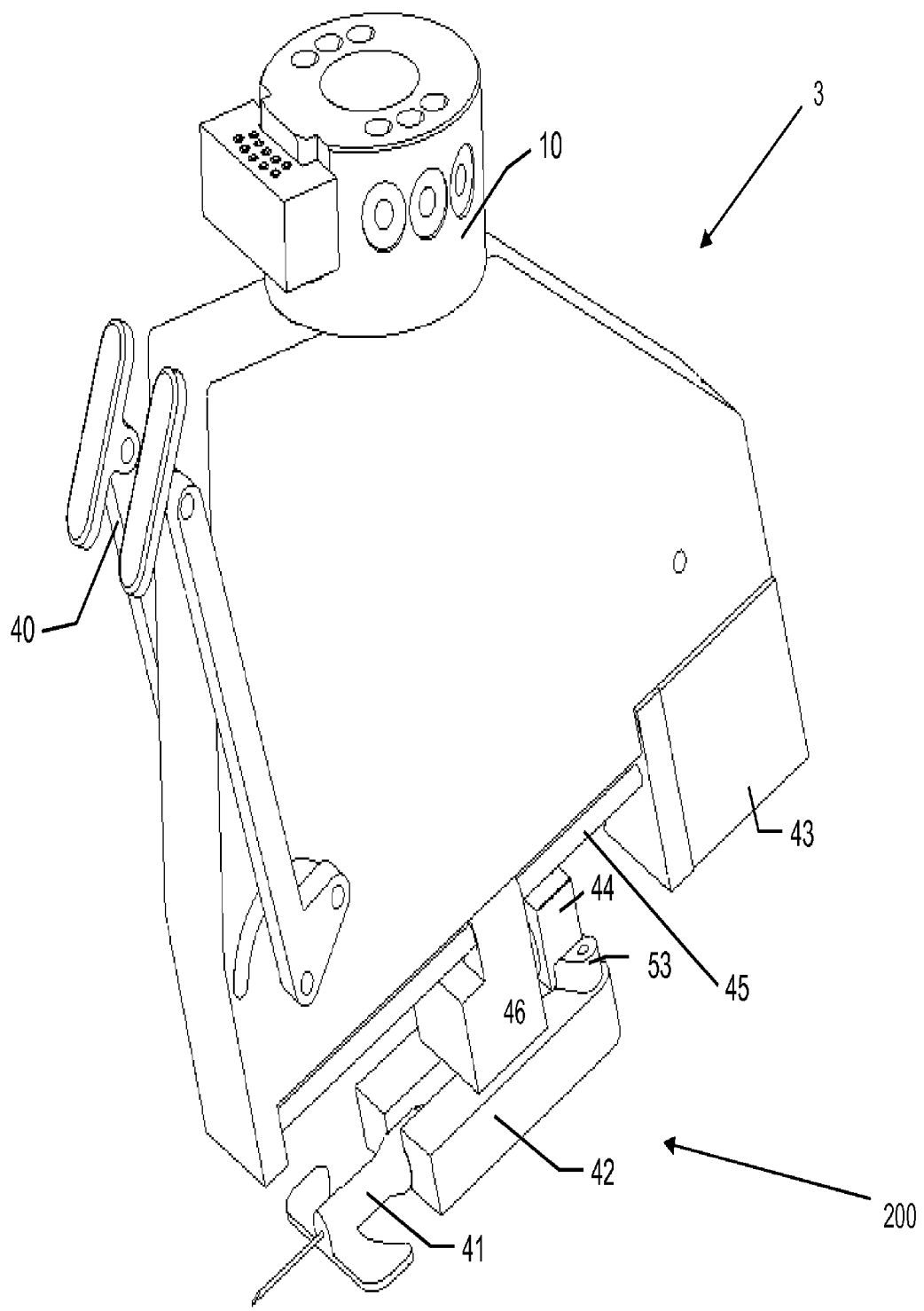
FIG. 11 illustrates an embodiment of a needle tool of the present disclosure for holding a needle.

FIG. 11 shows a perspective view of an embodiment of the needle tool 3. The female tool changer 10 may be attached to the top of the needle tool 3 to autonomously connect the needle tools to the robot arm 1. The needle tool 3 is designed to insert butterfly needles 41 into the patient's arm 7. The butterfly needle 41 may be gripped by a needle gripper assembly 200 comprising gripper fingers 42, a butterfly needle gripper body 46, a pneumatic piston 44, and butterfly needle gripper linkages 53. The needle gripper assembly 200 is similar to the catheter gripper 21 used in relation to the catheter tool 4 as described above. A stepper motor 43 moves the butterfly needle gripper body 46 along guide rails 45 to insert the butterfly needle 41. The needle tool 3 also includes stabilizer feet 40, which are shown in FIG. 11 in their retracted position.

Figure 12:
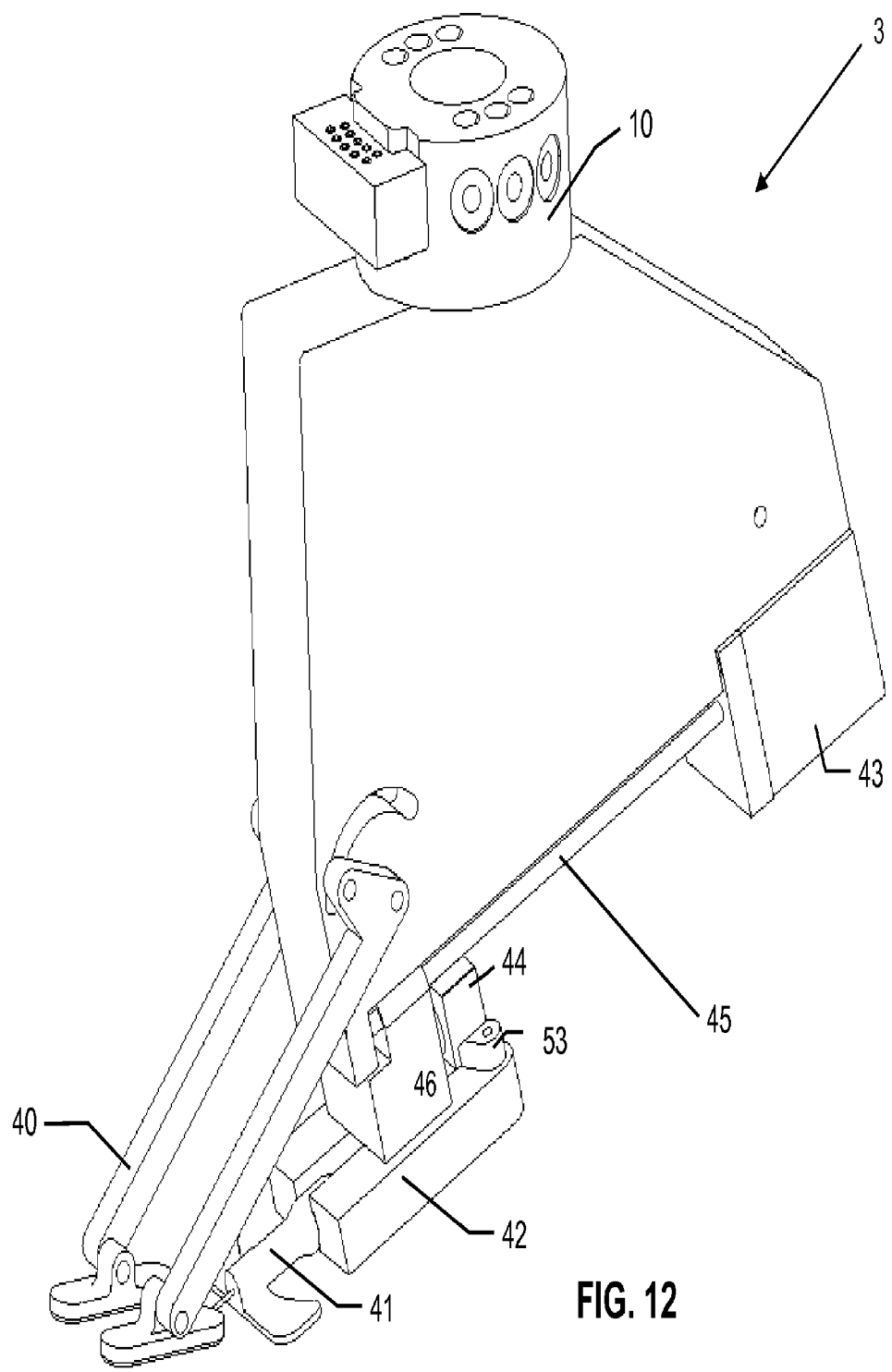
FIG. 12 illustrates an embodiment of a needle tool with its stabilizing feet in a deployed positions.

FIG. 12 shows a perspective view of the embodiment of the needle tool 3 of FIG. 11 after the butterfly needle 41 has been inserted. To insert the butterfly needle 41, the stepper motor 43 pushes the needle gripper assembly 200 forward, thus inserting the butterfly needle 41 into a target vein. FIG. 12 shows stabilizer feet 40 engaged, applying light pressure around the insertion site to stabilize the area around the insertion site.

Figure 13:
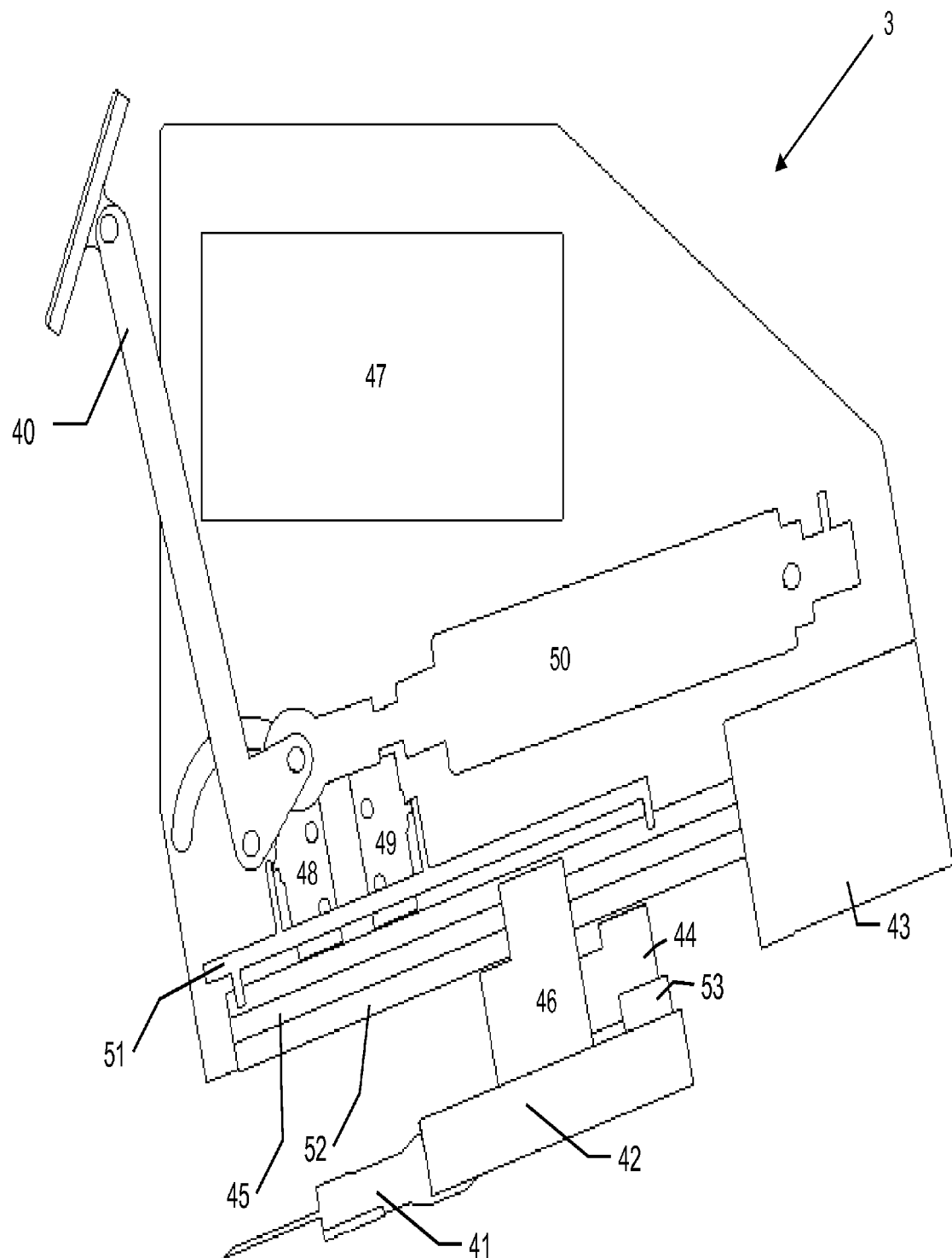
FIG. 13 and FIG. 14 are cutaway are cutaway views of an embodiment of a needle tool at various stages of a needle insertion procedure.

FIG. 13 shows a cutaway view of the embodiment of the needle tool 3 of FIG. 10 prior to insertion. In an embodiment, a blood draw tool control circuit 47 is used to command the various functions of the needle tool 3. Stabilizer feet 40 are shown in the raised or upright (resting) position, which is determined by a reverse acting pneumatic cylinder 50, which is also shown in the retracted position. The needle gripper assembly 200 is shown gripping the butterfly needle 41 in a retracted position along the guide rails 45. In an embodiment, a plunger type reverse limit switches 48 and a plunger type forward limit switch 49 are used along with a simple limit switch linkage 51 to prevent the stepper motor 43 from moving the needle gripper assembly 200 too far distally. Both limit switches 48 and 49 are shown in an inactive position in FIG. 13. It should be noted that other types of limit switches can be used instead of the plunger type forward and plunger type reverse limit switches.

Figure 14:
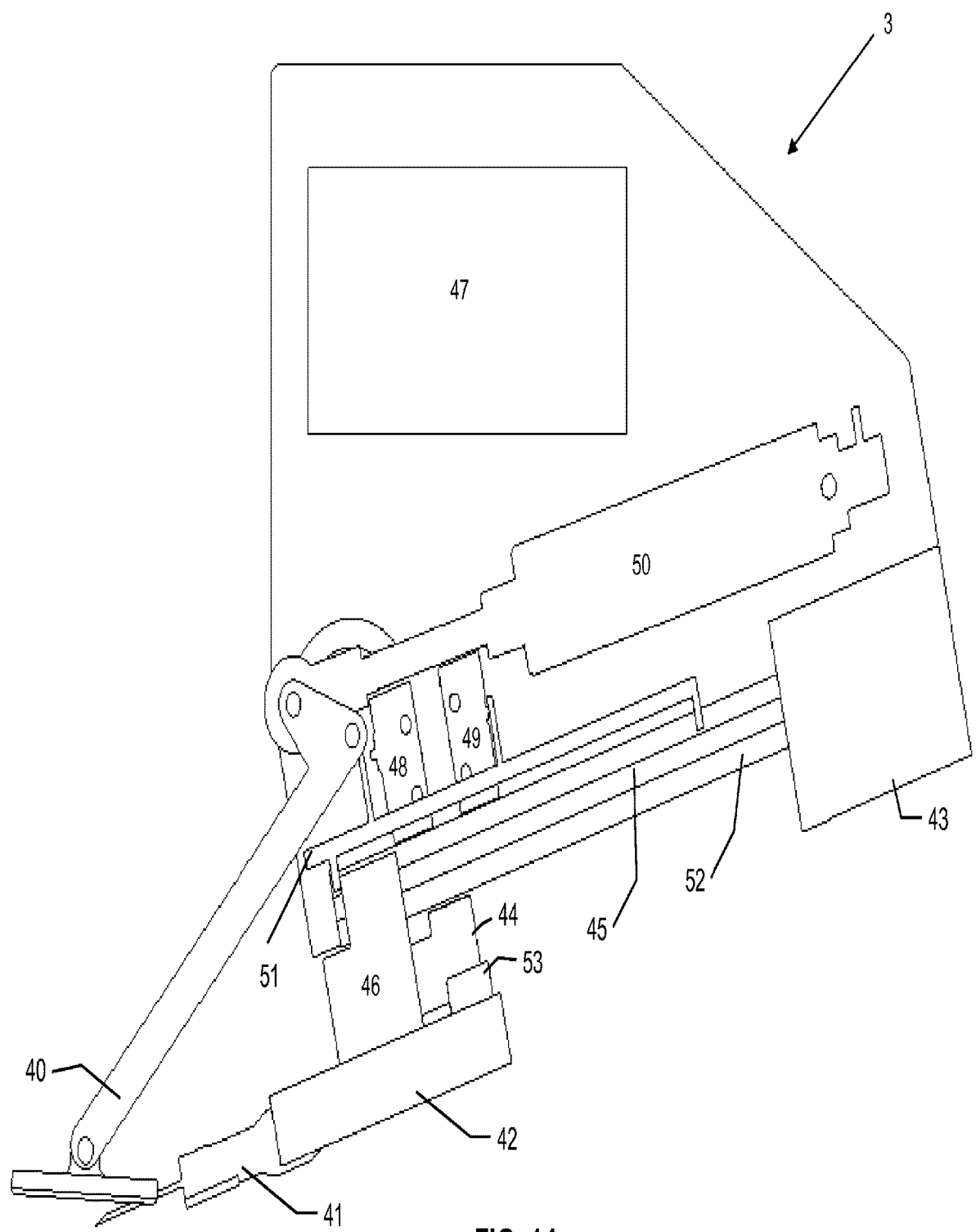

FIG. 14 shows a cutaway view of the embodiment of the needle tool 3 of FIG. 11 in the inserted state. Pneumatic cylinder 50 is shown engaged, pressing the stabilizer feet 40 onto the surface of the patient's arm 7. The butterfly needle 41 has been inserted into the patient's arm 7 by turning the lead screw 52 with the stepper motor 43, driving the needle gripper assembly 200 forward along guide rails 45. The plunger type forward limit switch 49 is shown depressed in FIG. 14, preventing any further insertion of the butterfly needle 41 into the patient's arm 7.

Figure 15A:
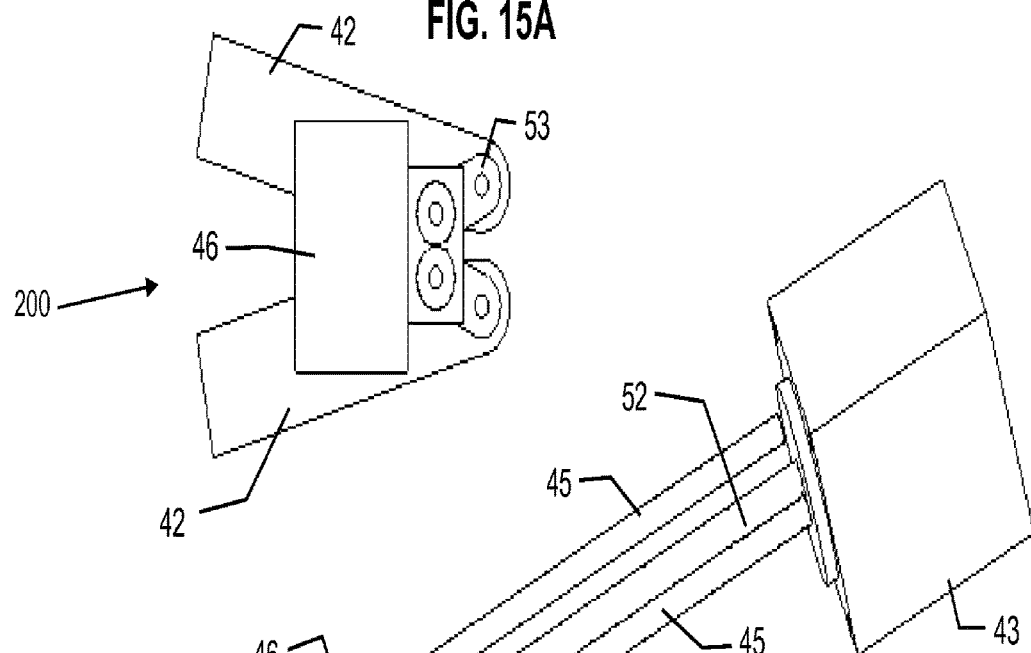
FIG. 15A, FIG. 15B and FIG. 15C show an embodiment of a gripper assembly and linear actuator of a needle tool.
Figure 15B:
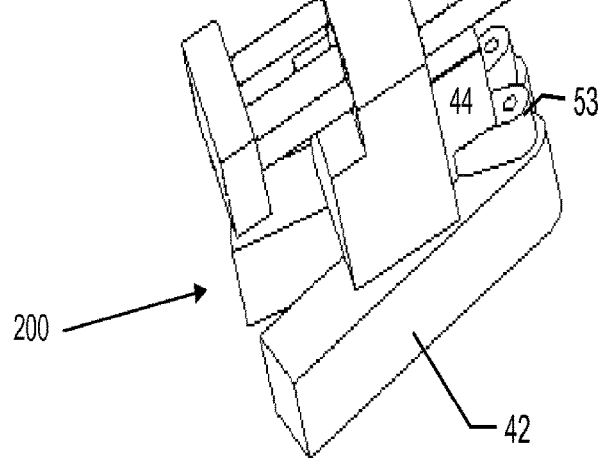
Figure 15C:
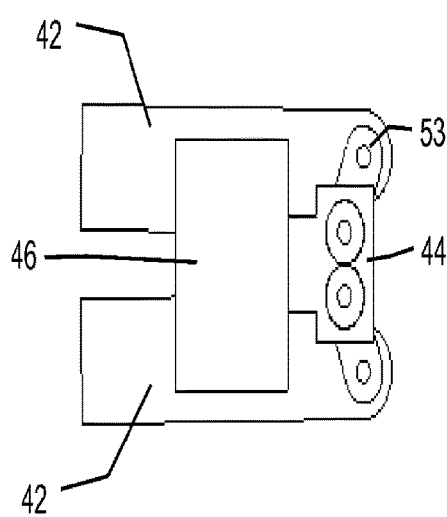

FIG. 15A, FIG. 15B and FIG. 15C show an embodiment of the needle gripper assembly 200 and linear actuator for the needle tool 3 of FIG. 11. In an embodiment, the needle gripper assembly 200 includes two butterfly needle gripper fingers 42, two butterfly needle gripper linkages 53, a pneumatic piston 44, and the butterfly needle gripper body 46. To grip the butterfly needle 41, air pressure may be applied behind the pneumatic piston 44 inside the gripper body 46, causing the butterfly needle gripper linkages 53 to spread the backs of the butterfly needle gripper fingers 42, closing them on the butterfly needle 41. The needle gripper assembly 200 is moveable by the stepper motor 43 along the axis of the butterfly needle 41. The stepper motor 43 turns the lead screw 52, which is threaded into the gripper body 46. As the lead screw 52 turns, the gripper body 46 slides along the guide rails 45, moving the gripper fingers 42 and the butterfly needle 41 with it for insertion into the patient's arm 7.

Figure 16:
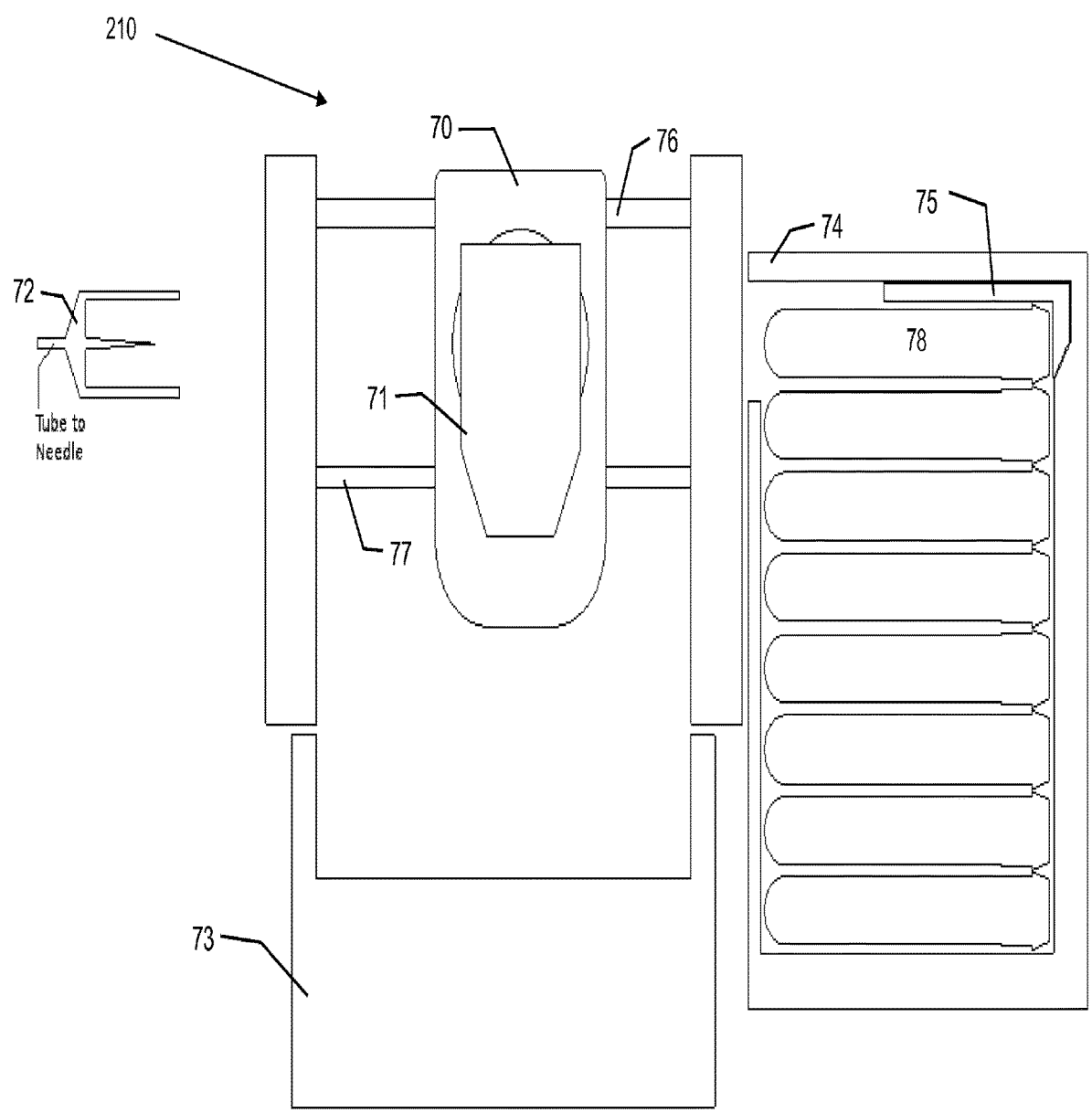
FIG. 16 shows an embodiment of a blood drawing tubes manipulator of the present disclosure.

In reference to FIG. 16, in an embodiment, the autonomous intravenous insertion system 8 has an automatic dispenser unit 74 that engages, disengages, and exchanges blood drawing tubes 78 with the inserted butterfly needle 41. In an embodiment, the blood drawing tubes 78 are VACUTAINER® tubes. FIG. 16 shows an embodiment of a manipulator 210 for blood drawing tubes 78. In an embodiment, the manipulator 210 is used for connecting the butterfly needles 41 to blood drawing tubes 78 to collect the blood samples from the patient. In an embodiment, the manipulator 210 includes a carriage 70 sliding along a guide rail 76, propelled by the rotation of a lead screw 77. In an embodiment, a collet chuck 71 for gripping blood drawing tubes 78 is rotatably attached to the carriage 70. In an embodiment, a storage unit 73 for filled blood drawing tubes 78 is located below the carriage 70. A dispenser unit 74 may be located next to the carriage 70. In an embodiment, the dispenser unit 74 uses a dispenser arm 75 to push new blood drawing tubes 78 into the collet chuck 71. In an embodiment, new blood drawing tubes 78 are rotated around to the piercing needle 72, and pressed onto the piercing needle 72, allowing blood to flow from the butterfly needle 41 through a tube to the piercing needle 72, and into the blood drawing tube 78.

Figure 17:
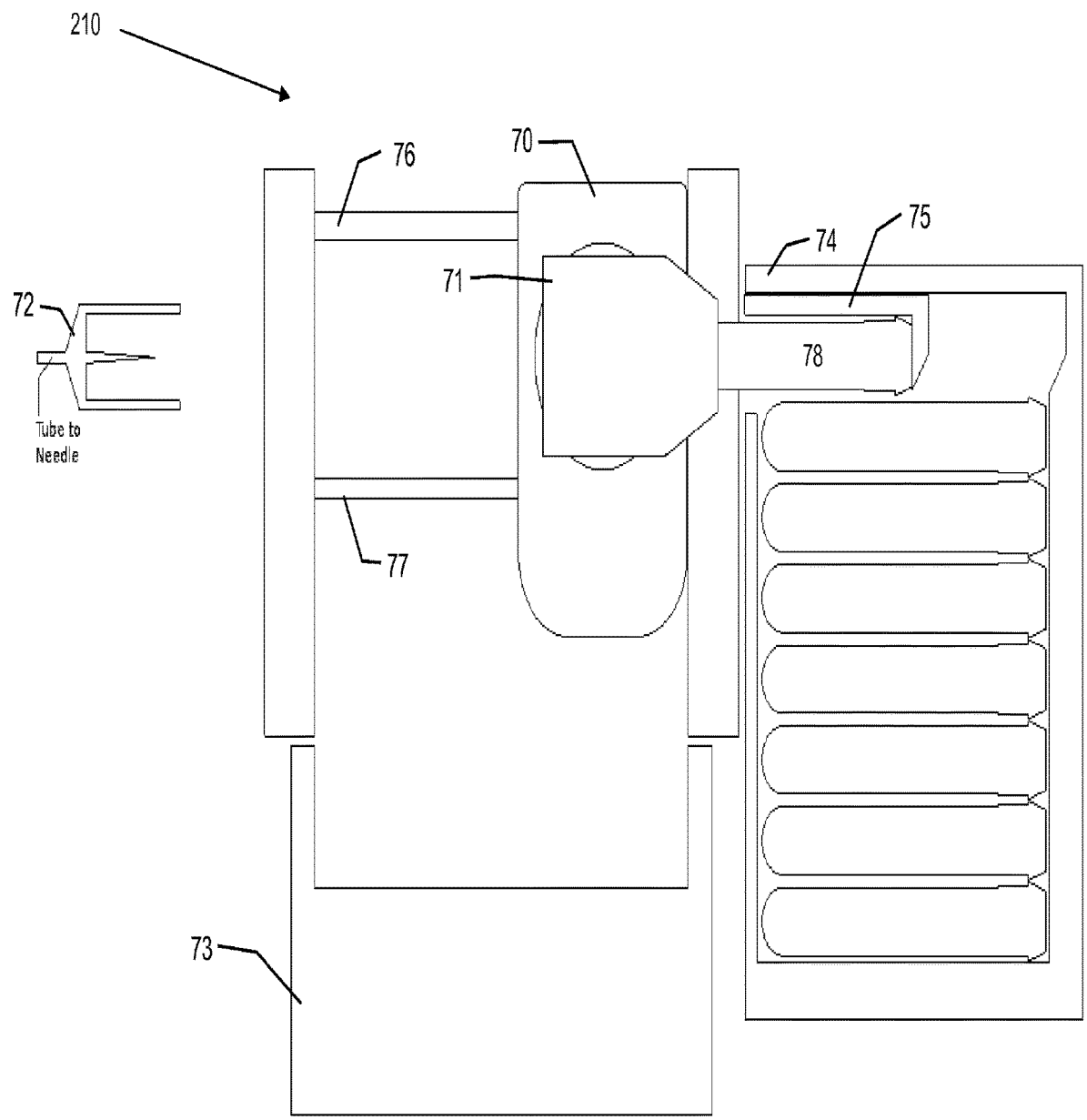
FIG. 17, FIG. 18 and FIG. 19 show an embodiment of a blood drawing tubes manipulator in operation.

By way of a non-limiting example, FIG. 17 shows the manipulator 210 operating to grab a blood drawing tube 78. As shown in FIG. 17, the carriage 70 is positioned next to the dispenser unit 74 to accept a new blood drawing tube 78, and the collet chuck 71 is rotated to line up with a blood drawing tube 78 in a dispensing position inside the dispenser unit 74. Next, the dispenser arm 75 of the dispenser unit 74 pushes the blood drawing tube 78 into the collet chuck 71, which securely accepts the blood drawing tube 78.

Figure 18:
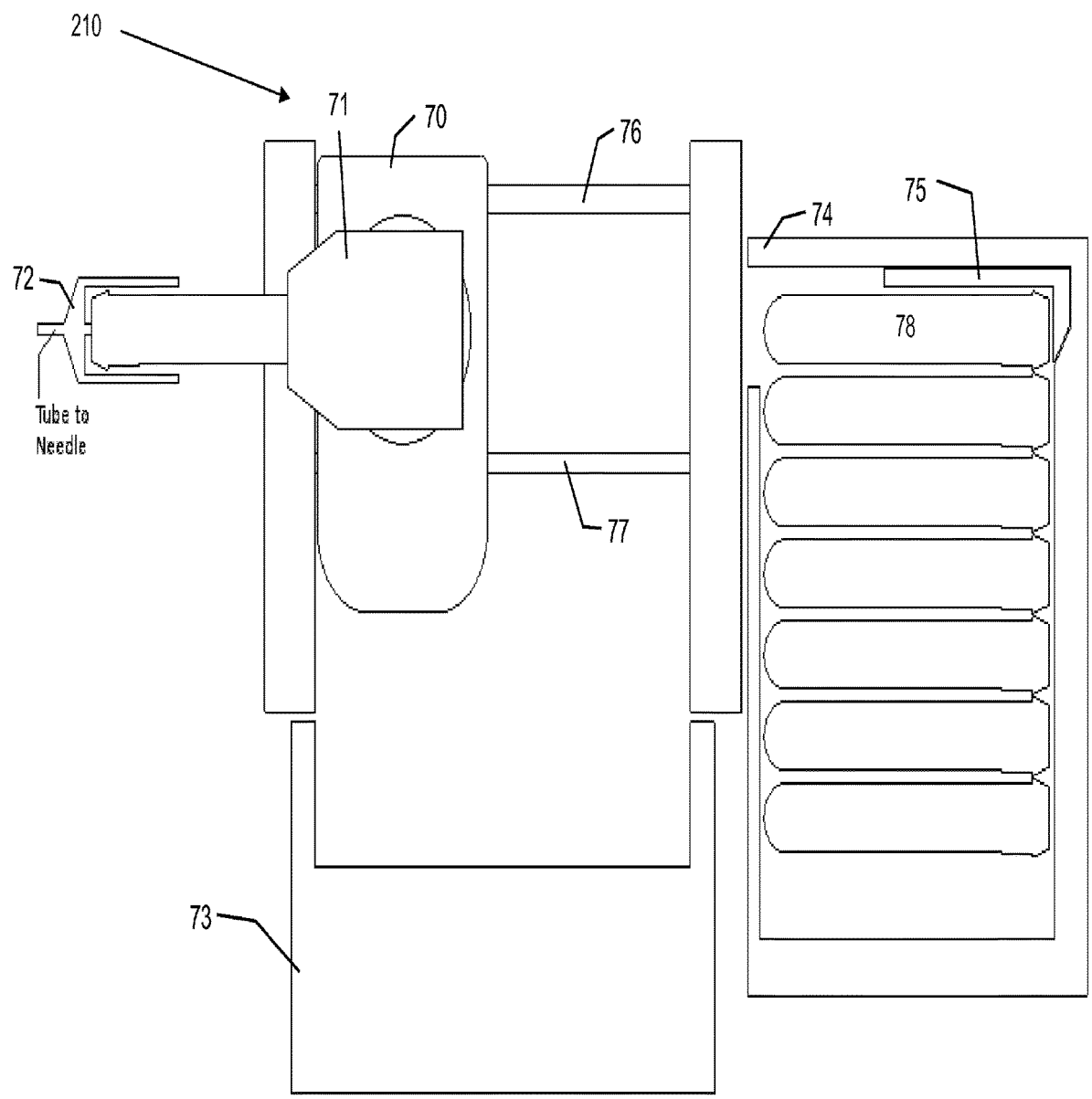

By way of a non-limiting example, FIG. 18 shows the manipulator 210 operating to engage the blood drawing tube 78 with the piercing needle 72. As shown in FIG. 18, the collet chuck 71 is rotated to line up with the piercing needle 72, and the carriage 70 is driven by the rotation of the lead screw 77 to push the blood drawing tube 78 onto the piercing needle 72. Contemporaneously, within the dispenser unit 74, the dispenser arm 75 is retracted to allow a new blood drawing tube 78 to move into the dispensing position.

Figure 19:
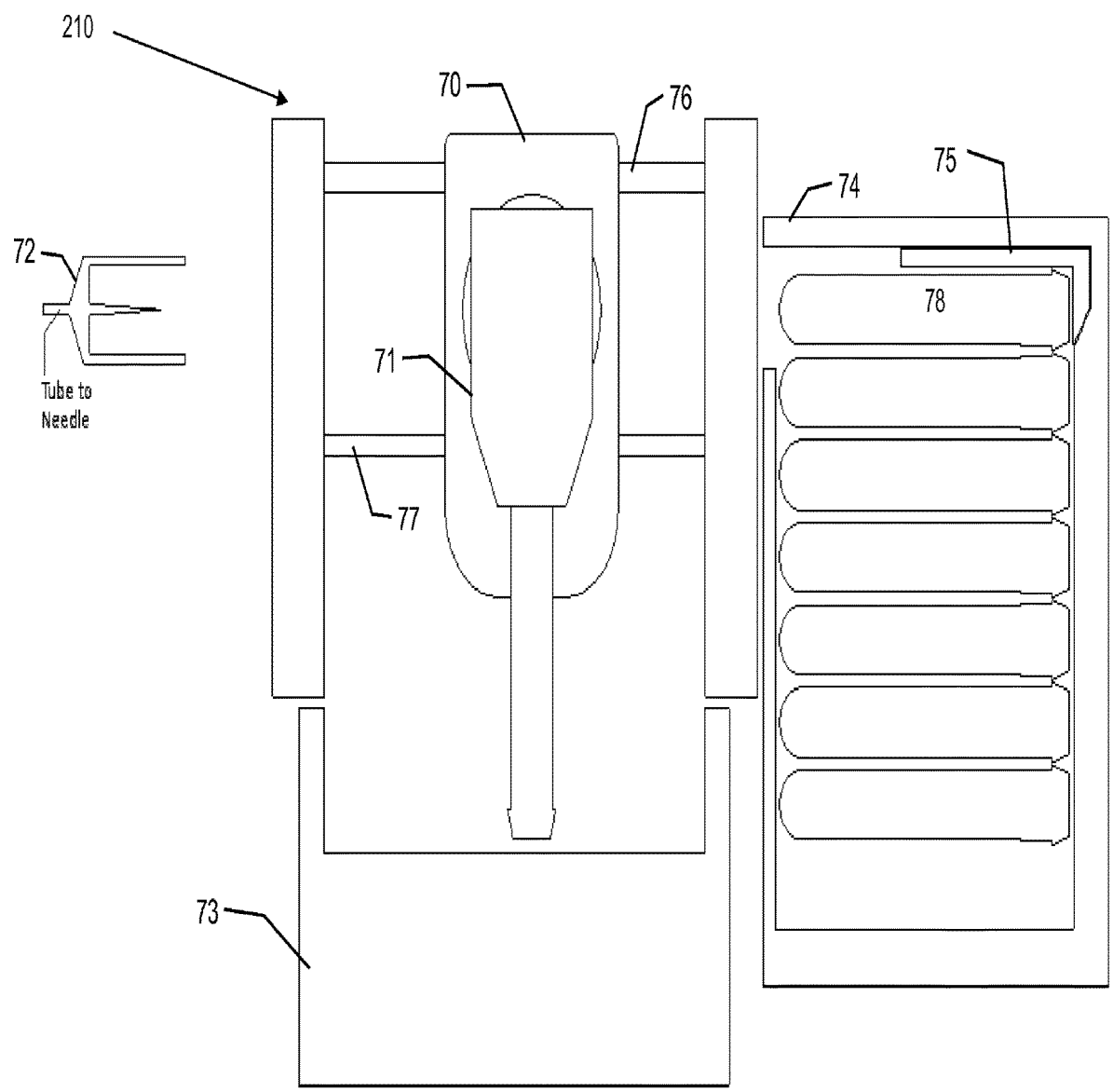

By way of a non-limiting example, FIG. 19 shows the manipulator 210 operating to place a filled blood drawing tube 78 into the tube storage unit 73. As shown in FIG. 19, the carriage 70 pulls the filled blood drawing tube 78 off of the piercing needle 72, and the collet chuck 71 rotates down to point into the tube storage unit 73. At this point the collet chuck 71 can drop the filled blood drawing tube 78 into the storage unit 73 where the filled blood drawing tube 78 is kept until it can be analyzed. Once the filled blood drawing tube 78 is released, the process described in reference to FIG. 17, FIG. 18 and FIG. 19 can be repeated to pick up additional blood drawing tubes 78 from the dispenser unit 74, push the blood drawing tubes 78 onto the piercing needle 72 and then transfer filled blood drawing tubes 78 into the storage unit 78 to obtain a desired number of samples.

In an embodiment, the autonomous intravenous insertion system 8 is provided with dispenser units 74 for needles 41, catheters 22, and blood drawing tubes 78. In an embodiment, the system 8 is capable of autonomous selection of correct medical devices to match the prescribed procedure in a timely manner, and to reliably and repeatably pick up the devices. The dispensers may also prevent contamination of the devices by keeping them separate from the hospital environment until ready for use. The dispensers are meant to be stationed near the robot arm 1, so that the robot arm 1 can pick up the appropriate tool upon command without having to be moved. Each piece of equipment may also be provided with its own storage unit that can be easily reloaded. When equipment is low, the user may be notified that it is necessary to renew the supply stock.

In an embodiment, the autonomous intravenous insertion system 8 of the present disclosure may utilize commercially available needles 41 and catheters 22 including, but not limited to, VACUTAINER® brand needles and vacuum blood specimen tubes and an indwelling intravenous cannula that can serve as a medication delivery device or a blood drawing device. Needles and cannulas and other devices that can be inserted into a vessel are referred here as end-effectors since they are the terminal attachment to the robot arm and the only part of the system which is invasive.

In an embodiment, the autonomous intravenous insertion system 8 of the present disclosure is configured to handle end-effectors and other single use components, such as blood drawing tubes, of various designs. In an embodiment, the autonomous intravenous insertion system 8 of the present disclosure is configured to autonomously load and dispose end-effectors and other single use components. In an embodiment, the autonomous intravenous insertion system 8 of the present disclosure is provided with syringe manipulators, arterial catheter insertion manipulators, ultrasound probes, or devices for other injection methods, including intradermal, subcutaneous, intramuscular or intraosseous injection.

A storage unit 73 for filled blood collection tubes 78 may also be included in the autonomous intravenous insertion system 8 of the present disclosure to enable controlling the temperature of test sample until they can be analyzed. In an embodiment, such a storage unit 73 may also keep the test samples safe from contamination and misplacement until they are to be collected and tested.

In an embodiment, the autonomous intravenous insertion system 8 of the present disclosure includes a disposal unit 96 for containing used butterfly needles 41 and catheters 22 after use. The used items in the disposal unit 96 can be emptied daily along with other medical waste, so used items need not be handled by nurses or patients, eliminating the risk of accidental punctures with contaminated needles 41 and catheters 22.

In an embodiment, the autonomous intravenous insertion system 8 of the present disclosure includes a tool docking and storage station 95 for the tools used by the system 8. In an embodiment, the tool docking and storage station 95 is an area out of reach to patients where the robot arm 1 can affix the correct tools for the job, and store unneeded tools until they are required. In an embodiment, the different devices and tools may be stored in a set of cubby-like units, where the system is pre-programmed to know what device is stored in each unit, as well as how to pick up, affix, and manipulate it. Alternatively, another possible configuration may be for each tool and complementary device to have its own dock and storage station.

In an embodiment, the medical procedure comprises an insertion procedure. In an embodiment, insertion procedure comprises an intravenous insertion procedure. In an embodiment, the intravenous insertion procedure comprises intravenous insertion of a butterfly needle 41 into the vessel of a patient's arm 7. In an embodiment, the intravenous insertion procedure comprises intravenous insertion of a cannula into the vessel of the patient's arm 7. In an embodiment, the vessel comprises a vein. In an embodiment, the vessel comprises a subcutaneous vein. In an embodiment, the vessel comprises a superficial vein. In an embodiment, the vessel comprises a deep vein.

Figure 20:
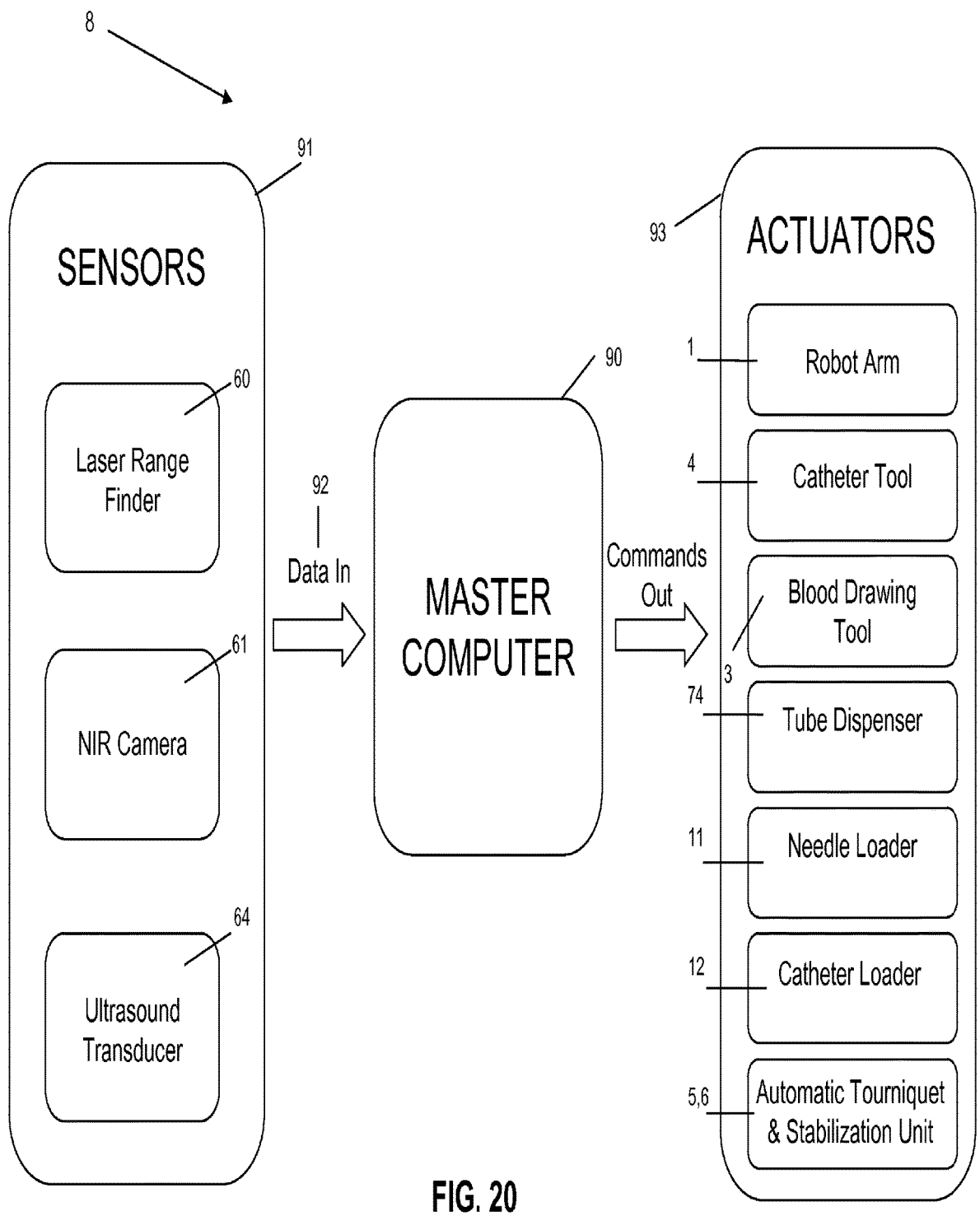
FIG. 20 is a block diagram illustrating components of an embodiment of an autonomous intravenous insertion system of the present disclosure.

FIG. 20 illustrates a schematic diagram of an embodiment of the autonomous intravenous insertion system 8 of the present disclosure. The system 8 includes primary sensors 91, including, but not limited to, a laser rangefinder 60, an NIR camera 61, and an ultrasound device 64 to collect sensor data 92 about the patient, which is sent to a master computer 90 and analyzed. Based on this sensor data 92 and the mode of operation, the master computer 90 sends commands to several primary actuators 93. In an embodiment, the primary actuators 93 include an automatic butterfly needle loader 11, an automatic catheter loader 12, needle tool 3, catheter tool 4, dispenser unit 74, as well as the robot arm 1. In an embodiment, the primary sensors 91 provide feedback as the primary actuators 93 execute their commands, allowing for more precise and error free operation. Feedback may include, but is not limited to, updated target position information, vein verification information, robot motion verification, ambient light measurement, and user errors such as excessive arm movement. Feedback is used throughout the process to ensure safe and reliable operation.

As illustrated in FIG. 20, in an embodiment, the autonomous intravenous insertion system 8 of the present disclosure includes one or more primary sensors 91 for acquiring sensor data 92 in real-time relating to three-dimensional coordinates and an orientation of a patient's vein located beneath the skin surface of the patient's arm 7; one or more primary actuators 93 for autonomous insertion of a butterfly needle 41 or cannula into the patient's vein; and a master computer 90 configured to execute a program designed to transform the acquired three-dimensional coordinates and orientation of the patient's vein into an optimal insertion path for the butterfly needle 41 or cannula to be inserted into the patient's vein, wherein one or more primary sensors 91 track the optimal insertion site for the butterfly needle 41 or cannula in real-time to provide a continually updated optimal insertion path so that the master computer 90 can generate a command to the actuators to instruct the actuators to guide the butterfly needle 41 or cannula along the continually updated optimal insertion path to insert the butterfly needle 41 or cannula into the patient's vein.

In an embodiment, the autonomous intravenous insertion system 8 of the present disclosure uses one or more primary sensors 91 to collect real-time sensor data 92 about the patient. The real-time sensor data 92 is sent to a master computer 90 configured to analyze the real-time sensor data 92 input into the computer. In an embodiment, the master computer 90 gathers sensor data 92 from the primary sensors 91 and any secondary sensors 213, and uses the information to coordinate the primary actuators 93. Suitable secondary sensors 213 include, but are not limited to, sensors that provide feedback to the primary actuators 93 such as limit switches or current sensors, and other peripheral sensors like a barcode reader 216. In an embodiment, the secondary sensors 213 include a tactile sensor for sensing needle contact, a force sensor for 'feeling' a successful vein penetration, or a color imager for detecting blood flow in the cannula.

The master computer 90, based on the analysis of the real-time sensor data 92 input into the master computer 90, outputs commands to the primary actuators 93. In an embodiment, the primary sensors 91 and secondary sensors 213 provide real-time feedback as the primary actuators 93 execute their commands, allowing for precise and substantially error free operation of the system while autonomously completing a medical procedure.

In an embodiment, the autonomous intravenous insertion system 8 of the present disclosure includes software, hardware and tools to carry out any procedure in these modes, including picking up the appropriate medical device, visualizing target insertion sites, localizing targeted insertion sites, calculating and following a path to the targeted insertion site, inserting the device in the appropriate location without harm to the patient, executing ancillary tasks that complement the procedures, extracting the device without harm to the patient, and finally discarding the used device are built in to the system. That is to say that the autonomous intravenous insertion system 8 needs no assistance from the user, unless so desired. In an embodiment, a user may assist in selecting the procedure needed to be done on the patient, and replace stock equipment when necessary. The following hardware units enable the system to have these capabilities.

Figure 21:
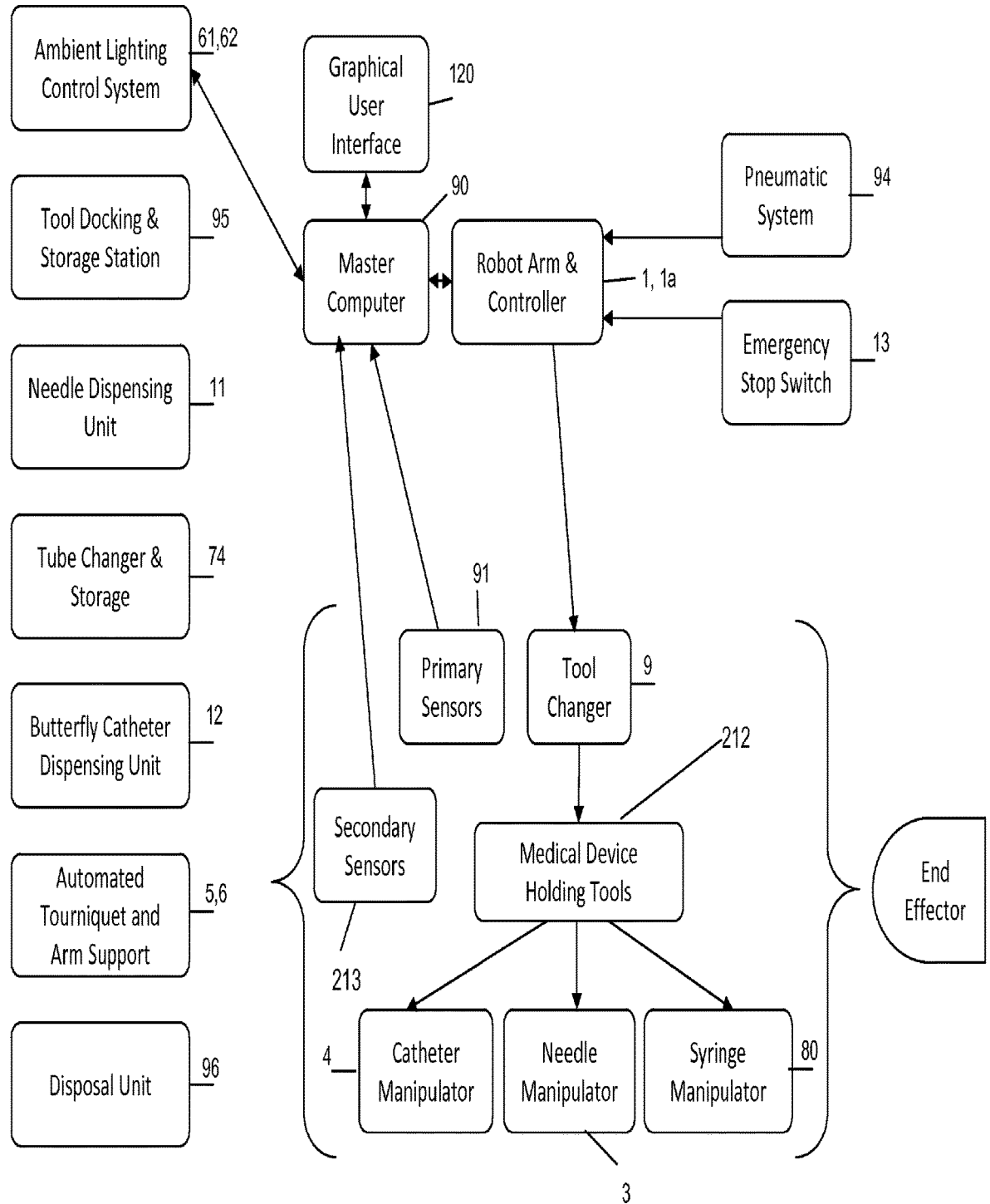
FIG. 21 is a flow diagram illustrating hardware units of an embodiment of an autonomous intravenous insertion system of the present disclosure.

FIG. 21 depicts an embodiment layout of hardware involved in the operation of the autonomous intravenous insertion system 8 of the present disclosure. For the purposes of this description, arrows pointing to a module indicate that the module the arrow points from either manipulates that module, or is a control input to that module. Bidirectional arrows indicate that both modules interact in some way. In an embodiment, the main components are connected in the center of the drawing, including the master computer 90, graphical user interface (GUI) 120, robot arm 1, and robot arm controller 1a, the primary sensors 91, and medical device tools 212. Suitable medical device tools 212 include, but are not limited to, a catheter tool 4, needle tool 3, syringe manipulator and possibly other tools 80. In an embodiment, the primary sensors 91 and the medical device holding tools 210 are mounted onto the sixth axis of the robot arm 1, together making the robot arm's end effector. As described above, in an embodiment, the autonomous intravenous insertion system 8 includes support or secondary systems (drawn on the left side of the diagram), which aid the autonomous operation of the autonomous intravenous insertion system 8. In an embodiment, these support systems are controlled by the master computer 90. Exemplary support systems include, but are not limited to, lighting control systems 61 and 62, a tool docking and storage station 95, an automated butterfly needle dispenser unit 11, a dispenser unit 74, an automated catheter dispenser unit 12, an automated tourniquet cuff 5, a wrist stabilizing cuff 6, and a disposal unit 96.

In an embodiment, the robot arm 1 is the primary actuator in the system 8, allowing for precise spatial control of the end-effector, medical device holding tools 212, and/or primary sensors 91. In an embodiment, the robot arm 1 is supported by a pneumatic system 94 for powering some of the primary actuators 93 in the end-effectors and the tool changers 9 and 10, and an emergency stop switch 13 for safety. The robot arm 1 autonomously connects to one or more medical device tools 3 and 4 via the tool changers 9 and 10, allowing for a wide variety of procedures to be completed without the need for modification by a technician. Such medical devices include catheters, blood drawing needles and tubes, and syringes.

In an embodiment, the autonomous intravenous insertion system 8 is supported by additional devices which allow the system 8 to function autonomously. In an embodiment, a circuit for measuring and compensating for ambient light conditions 61 and 62 ensures the proper illumination for the NIR camera 61 functions. In an embodiment, an automatic needle dispenser 11, automatic catheter dispenser 12, blood drawing tubes 78 and possibly other devices used for the various procedures are included in addition to a disposal unit 96 for used devices, allowing procedures to be completed without the need for human contact with sterile devices or contaminated "sharps." In an embodiment, a storage unit 73 is also available for holding filled blood drawing tubes 78 out of harm's way until the blood can be analyzed. To increase the visibility of the subject's vessels, an automatic tourniquet cuff 5 is used. In an embodiment, the wrist stabilizing cuff immobilizes the patient's arm 7 to prevent movement of the patient's arm 7 during the procedure. In an embodiment, a tool docking and storage station 95 for holding unused end-effectors is included so that all tools are available to the system 8 when the system 8 needs such tools for a procedure.

In an embodiment, the autonomous intravenous insertion system 8 of the present disclosure may include three separate subsystems. In an embodiment, the first or core subsystem includes a robotic arm 1, a robot arm controller 1a, a master computer 90, and a graphical user interface (GUI) 120. In an embodiment, the second of the end effector sub-system includes primary sensors 91, tool changers 9 and 10, and medical device holding tools 212 so the robot arm 1 can operate in any given procedure. The third subsystem is hardware meant to take care of all ancillary procedures that ensure the system 8 will work properly. The third subsystem modules include, but is not limited to, ambient lighting control systems 61 and 62, medical device dispensing units 11 and 12, a disposal unit 96, a storage unit 73 for medical devices and other disposable devices used to carry out the procedure, an arm support station, a tourniquet cuff 5 or tourniquet-like applier, and a tool docking and storage station 95, which holds tools used to grip or manipulate medical devices used during one of the contemplated medical procedures.

A user interface may include a screen displaying a graphical user interface (GUI) 120, where procedures and options will be displayed to the user so that they may indicate what specifically the robot needs to do. User input may be coordinated with operation of the robotic arm by the main program running on the master computer 90. The user may instruct this program to perform a medical procedure on the patient, such as drawing blood, inserting an IV, or delivering medicine via a syringe. Target vein selection may be carried out in one of two modes automatic and semi-automatic. The automatic mode corresponds to the system running completely on its own. In such a mode, the user selects the procedure that needs to be done, and then leaves the system to do its job. A target insertion site will automatically be chosen by the system 8. The semi-automatic mode corresponds to the system highlighting potential insertion sites based on the same insertion site-finding algorithms used in automatic mode, and then returning these sites to the user in highly distinguishable bounding boxes. In such a mode, the user may be prompted to click on the corresponding box, at which time the instant system will carry out the desired procedure on that site. If no suitable sites are presented to the user or the user wishes to choose a site on his or her own, the user can click and drag on the desired target in one of the two images presented to them by the GUI 120. Once the insertion location is picked, the robot operates autonomously. If additional safety measures are needed, the robot may ask the user to verify the insertion site once it has reached the site's vicinity. The user interface provides a control panel that allows the user to choose the procedure the robot is to carry out. It should be noted that the user interface need not be in the vicinity of the robot; in an embodiment, it may be in a remote location.

In an embodiment, the GUI 120 is displayed on a touch screen showing video of either the original or processed image, modified with suggestions target insertion sites. Once a target has been selected, the GUI 120 displays the current image from the NIR camera 61 with the tracked site highlighted. In an embodiment, the GUI 120 also gathers any user input that is required, for instance user verification that a desired procedure can be carried out or needs to be terminated. In an embodiment, the GUI 120 is supported by the master computer 90.

The master computer 90 coordinates all the input information from the primary sensors 91, secondary sensors 213, if present, and the GUI 120, and also controls the actuation of the primary actuators 93, including the robot arm 1 and any relevant medical device holding tools 212 for handling standard medical devices such as cannulas, Y-type catheters, VACUTAINER® phlebotomy equipment, and syringes. In an embodiment, the master computer 90 provides a control link to the robot arm controller 1a (described below as the slave unit), which takes care of sending signals to the robot arm 1 to enable the movement of the robot arm 1.

By way of a non-limiting example, the master computer 90 runs the main program 115 that provides a GUI 120 to the system, gathers and analyzes data from the primary sensors 91, highlights potential insertion sites, analyzes these sights to find the best insertion location based on a unique vein classifier, localizes the targeted insertion site, tracks the targeted insertion site, generates targeted points in space to move through along the targeted insertion path, commands the robot arm control unit with high level commands such as insert, extract, pick up, discard, change tools, etc., and receives information from the robot arm 1 such as its current position in six dimensions, and its status (error, carrying out task, task done, etc). The main program 115 may communicate to the slave wirelessly or via an Ethernet port.

The master-slave system may be configured in a number of ways. The master and slave may be (1) rolled around together on a cart from room to room with the robot above them, (2) be stationed in a room wired directly to the robot, (3) be connected wirelessly through a network, in which case the slave is paired with the robot, while the master computer is stationed remotely where the user operates it, or (4) both be built in to a manually-operated or autonomous mobile robot that has capabilities similar to the system described. Other configurations may also be possible.

Figure 22:
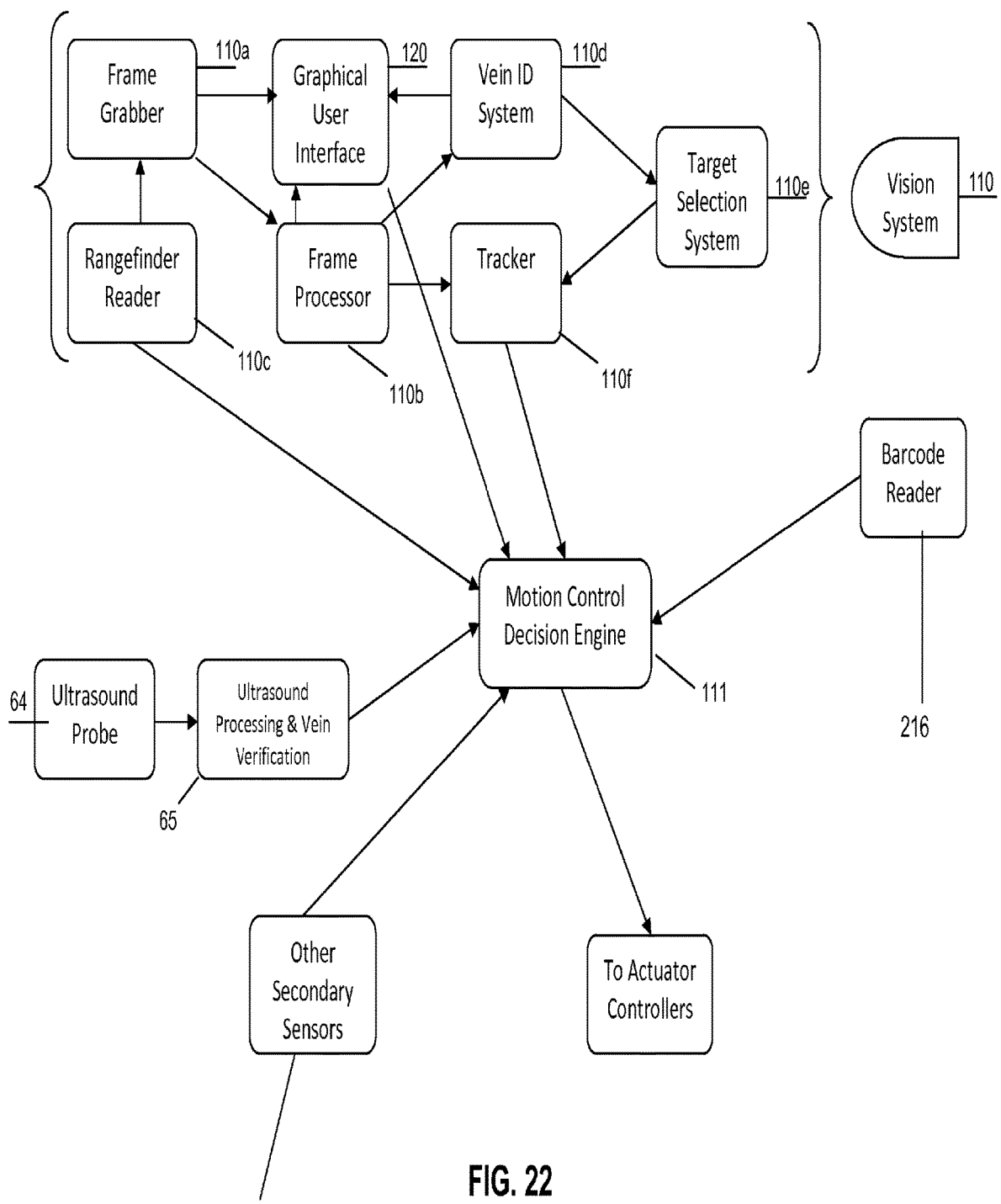
FIG. 22 is a schematic diagram illustrating components of an embodiment of an autonomous intravenous insertion system of the present disclosure.

FIG. 22 is a broad overview of an embodiment of software modules for governing the operations of the autonomous intravenous insertion system 8. The system 8 includes a vision system 110. In an embodiment, the vision system 110 is largely responsible for decisions made by the motion control decision engine 111 in controlling the primary actuators 93 involved in the system 8. In an embodiment, the vision system 110 finds potential targets through a series of image processing and vein identification algorithms. The information from the vision system 110 is one of the primary sources of information for the motion control decision engine 111, which is responsible for controlling the primary actuators 93 involved in the system. In an embodiment, the motion control decision engine 111 further relies on support systems, such as the ultrasound device 64 and ultrasound processor and vein verification system 65 for verifying that a vein lies under the specified target, other secondary sensors 213, and possibly a barcode reader 216 for patient identification and tube organization. It should be noted that one or all of the support systems may be incorporated into the vision system 110 or one or more of the modules shown as part of the vision system 110 in FIG. 22 may be used as support systems.

In an embodiment, the frame grabber 110a is responsible for continuously grabbing images from the NIR camera 61. The rangefinder reader 110c associates a depth reading with the center of the image. The frame grabber 110a feeds video to the frame processor 110b as well as to the GUI 120. The frame processor 110b also feeds into the GUI 120, so that the user may view both the original and the processed images. The frame processor 110b is responsible for processing the original input image from the frame grabber 110a in order to select veins from the surrounding skin. The processed image is fed into the vein identification system 110d, which includes, but is not limited to, algorithms to find the patient's arm 7, find the patient's elbow, and analyze vein-like structures inside the arm and elbow area, among others.

The vein identification system 110d feeds potential veins to be targeted for insertion to the target site selection system 110e, which, depending on the mode of operation, enables final target selection. The target site selection system 110e can operate in a semi-automatic or fully automatic mode. In semi-automatic mode, the target site selection system 110e can suggest to the user the potential target veins that it scores best for medical device insertion. In fully automatic mode, the target site selection system 110e automatically selects the best target by beginning to track the target vein that earned the highest score out of all other scored sites. Scoring of a potential target site is based on its size, shape, and closeness to the patient's elbow (without being directly on it), and is handled within the target site selection system 110e. In an embodiment, once the target for insertion is selected, its image is passed to the vein tracker 110f, which tracks the insertion site through movements of the patient's arm 7. Tracking the target site through subject movement ensures that the insertion site originally selected remains the one that is penetrated by the medical device. In an embodiment, once tracking has begun, the motion control decision engine 111 controls the robot arm 1 to approach the target site and carry out the procedure upon arrival to the target site.

An ultrasound device 64 may be used together with the vein identification system 110d to detect false positives in the original image or to confirm true positives or negatives. In an embodiment, one or more secondary sensors 213 may be attached to the end-effector to increase the accuracy and reliability of the system 8 as a whole. In another embodiment, the secondary sensors 213 may be attached to the main sensor assembly 2 or one of the medical device holding tools 212. In an embodiment, the operation of the system 8 can also be enhanced by including a barcode reader 216 for scanning barcodes on the outside of medical devices, and a link to a database for accessing and recording patient data during the procedure. In an embodiment, the vision system 110 may be comprised of various algorithms including but not limited to a frame grabber 110a, a frame processor 110b, a rangefinder reader 110c, a vein identification system 110d, a target site selection system 110e, and a vein tracker 110f, as shown in the top portion of FIG. 22.

In an embodiment, the first step of the vision system 110 is to have the frame grabber 110a retrieve a frame from the NIR camera 61, and for the rangefinder reader 110c to retrieve a distance from the laser rangefinder 60. Information from these functions can be combined so that an image always has a corresponding depth of field attached to the image, allowing the inference of three-dimensional coordinates from a two-dimensional image. In an embodiment, new frames are displayed to the user on the GUI 120 along with a processed and enhanced frame that depicts veins in the image by highlighting them in a bright color. A target insertion site is selected out of the potential targets either automatically or manually, as discussed above, and the target is then tracked by the vein tracker 110f continuously until insertion is completed. Information from these functions can be combined so that an image always has a corresponding depth of field attached to the image, allowing the inference of three-dimensional coordinates from a two-dimensional image. In an embodiment, new frames are displayed to the user on the GUI 120 along with a processed and enhanced frame that depicts veins in the image by highlighting them in a bright color. A target insertion site is selected out of the potential targets either automatically or manually, as discussed above, and the target is then tracked by the vein tracker 110f continuously until insertion is completed.

In an embodiment, certain portions of the program controlling the system 8 can run separately from the main process. These "threads" are run independently in order to enhance their speed and reliability. In an embodiment, the frame grabber 110a, frame processor 110b, rangefinder reader 110c, and vein tracker 110f are all separate threads from the main process allowing for real-time images to be updated at regular intervals regardless of the other program functions. In this manner, if the main process is waiting for user input or running a time-consuming algorithm, the frame grabber 110a and other threads will continue operating in the background to ensure that the information they provide is uninterrupted and up-to-date. Another advantage is that non-fatal runtime errors (such as unexpected input or other unexpected environmental issues) interrupt only the main process, while any other threads can continue to gather data.

Video is displayed through the GUI 120, as described below in FIG. 25, FIG. 26, and FIG. 27. When target insertion sites are to be selected, live feeds are displayed to allow the user to select a site for insertion. In an embodiment, an unprocessed feed direct from the NIR camera 61 and a processed feed displays potential targets or tracked objects. In an embodiment, the GUI 120 includes any necessary buttons for user input, for example, a manual override button in case a user wishes to choose a different vein for insertion than the selected site.

In an embodiment, the frame processor 110b is a separate thread which waits for new frames from the frame grabber 110a and processes those images into a binary image (black or white, no grays). When the images are processed, the white parts of the image (dark spots and edges in the original image) correspond to areas of interest, including without limitation, veins, shadows, the sides of the patient's arm 7, or any other objects in the frame. In contrast, black parts correspond to uniform areas of similar color such as skin or background. In an embodiment, this processed image does not contain any information about potential veins, but highlights all possible items in the image that might be veins.

The frame processor 110b passes the processed image to the vein identification system 110d. In an embodiment, the vein identification system 110d identifies potential areas of interest and considers a number of factors for each area of interest to determine if it is a vein or not, and if that vein is a viable insertion site. In an embodiment, the vein identification system 110d is programmed so each white shape in the binary image is measured to determine if it has the correct size, shape, orientation, thickness and length to be a viable target for insertion. In an embodiment, the vein identification system 110d has trained a vein classifier to take in information about the size, shape, orientation with respect to the arm, thickness, and length. All other blobs are ignored, and the vein-like blobs are then analyzed further to rank them and categorize them. In an embodiment, rankings are given based on the thickness of the target vessel, its overall size, and location relative to the subject's elbow.

If an intersection of multiple veins is encountered, such as the junction between the basilica and median cubital vein, the intersection can be split into separate veins so each straight length of vein is graded separately. Junctions can be detected by a combination of perimeter shape analysis, convexity/concavity of the targets outer contour, perimeter-area analysis, orientation analysis, and bounding box dimensions. In an embodiment, if the median cubital vein can be correctly identified, it will generally rank the highest unless it is relatively faint and another vein is deemed a better risk. If the user chooses, the user can override the selection made by the vein identification system 110d and choose any viable vein from the available options.

Once the vein identification system 110d identifies a suitable insertion site, the selected target is sent to the vein tracker 110f. The vein tracker 110f can preserve the original shape and orientation of the insertion site as selected to later compare the saved image with future images in order to keep the target insertion site in sight despite of movement by the robot arm 1 and/or the subject. In an embodiment, the vein tracker 110f updates information about the relative position of the target insertion site to the medical device manipulator 212 and sends coordinates and approach angles to the motion control decision engine 111 to be processed into motion commands.

The motion control decision engine 111 takes the tracking information from the vision system 110 and, optionally, other sensory information from secondary sensors 213 or the ultrasound device 64. Based on this information, the motion control decision engine 111 decides whether to move, insert, extract, or whether it is safe to do any of these things. In an embodiment, the motion control decision engine 111 can request a scan of the target insertion site area by the laser rangefinder 60 to determine the local topography of the patient's arm 7, so that the butterfly needle 41 or catheter 22 is inserted in the best direction with respect to the patient's vein and forearm. In an embodiment, the robot arm 1 is caused to move above the insertion site with visual serving techniques, based on position feedback. That is, a displacement vector is calculated from the current position to the target position, and the robot arm 1 is controlled to move along that direction. The distance between the insertion site and the location of the laser rangefinder 60 broken up into a path, which the robot arm 1 follows until the robot arm 1 reaches a position suitable to initiate insertion. In an embodiment, the robot arm 1 is positioned directly above the desired insertion location. In an embodiment, the path for the robot arm 1 is continuously updated as the image insertion site is tracked by the vein tracker 110f, and the updated insertion path is sent to the robot controller 1a subsequent to its calculation to guide the robot arm 1.

Once all the necessary information has been gathered about the insertion site and the vein's existence has been verified, commands can be sent to deploy the stabilizer feet 20, 40 of the medical device holding tools 212 so that the target vein is isolated and secured. Next, the robot arm 1 may cause the end-effector to move to the final position and be inserted. In an embodiment, the motion control decision engine 111 continues to monitor sensory information to ensure that it remains safe to insert the medical device tool 212 into the patient's arm 7. In an embodiment, the motion control decision engine can decide to abort the insertion if, for example, the patient moves excessively or any of the robot functions are lost for any reason. In an embodiment, the motion control decision engine 111 also selects which tools are needed for the desired procedure, and commands the robot arm 1 to pick up selected tools and any corresponding medical devices. In an embodiment, the motion control decision engine 111 is made aware of the correct procedure to follow based on some form of user input, which may include directly using the system's GUI 120 locally or remotely, or connecting to the system via a network. In an embodiment, the system 8 is designed to work with a patient database, which can be updated to reflect that the patient has undergone the said procedure, along with any other information required about the procedure by the particular table. In an embodiment, the database can be updated to include procedure specific notes or details, such as how many tubes of blood were drawn or how many cc's of medicine were injected, the identification number of the medical personnel who authorized the procedure, and how the patient reacted to the procedure.

Information from the secondary sensors 213 may also be used to alter the decision-making process. In an embodiment, a tactile sensor may be provided to indicate a successful navigation to the user's skin. In an embodiment, a force sensor is provided to relay data about the penetration of the butterfly needle 41 or catheter 22 through the wall of the vein.

The motion control decision engine 111 may also consider information from the ultrasound device 64 when initiating or controlling the insertion procedure. In an embodiment, the ultrasound device 64 is used for verification of the previously found veins or for specifying the exact location of veins underneath the skin. The ultrasound device 64 may include its own software module, ultrasound processing and vein verification system 65, for decoding the complex signals from the transducer into usable information about what is beneath the skin. With this system in place, an image recognition algorithm, such as template matching, for example, may be used to identify the vein underneath the skin, find its center point, and from that find its depth underneath the skin. This depth can be sent to the robot so it can calculate where the final insertion position will be. Once this vein has been identified, it can easily be tracked throughout time.

Software may also control any other medical devices or subsystems added to the autonomous intravenous insertion system 8 of the present disclosure, such as a blood pressure measurement machine or a temperature measurement machine.

As mentioned above, safety precautions may be built in to the system's software. In an embodiment, the system 8 may include safety features to ensure that it (1) avoids entering an infinite loop or (2) can stop the procedure at any time. In addition, the system 8 may include an option for the user to extract the medical device tool 212 at any time during the procedure.

Figure 23:
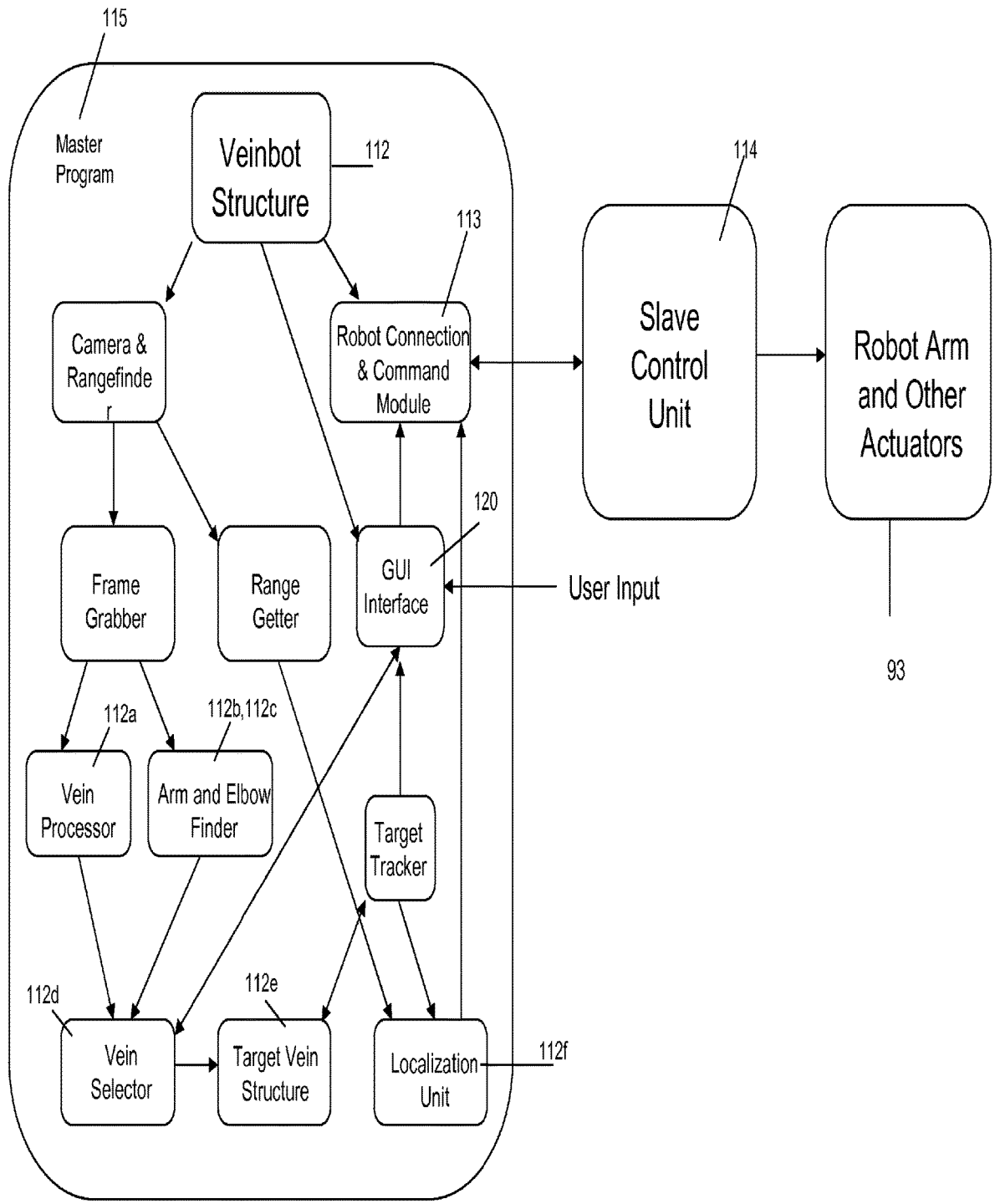
FIG. 23 is a schematic of software architecture and modules in an embodiment autonomous intravenous insertion system of the present disclosure.

FIG. 23 illustrates an embodiment software architecture designed to run the autonomous intravenous insertion system 8 of the present disclosure. The autonomous intravenous insertion system 8 includes an NIR camera 61 and a laser rangefinder 60, a set of robot control instructions, and a visual control panel which enables the user to interact with the system. Video may be processed, and a method of vein selection may be chosen, at which time the selected area is tracked and localized. Following insertion site localization, further control commands may be sent to the robot control unit, such as a command for inserting the attached medical device. When commands are received from the robot control unit, the unit may return a signal to the master program verifying that the correct command was received.

In an embodiment, the autonomous intravenous insertion system 8 of the present disclosure is controlled by a main software program 115 executable on a computer configured to analyze one or more input signals acquired by one or more sensory devices. The master computer 90 analyzes the one or more input signals using the main program 115 and transforms the data or information acquired by the signals into a plurality of commands which are then output to one or more primary actuators 93 as instructions to then instruct the one or more primary actuators 93 to perform an intravenous insertion procedure. In an embodiment, the signals acquired using the one or more sensory devices 91 and 213 are transformed into images which can be viewed on a video display 121 for the operator of the system to see. In an embodiment, the signals capture a preprocessed image and present the preprocessed image on the video display 121 for the operator of the system to see. In an embodiment, the master computer 90 is configured to transform the preprocessed image of the patient's arm 7 into the patient arm having a plurality of boxes projected onto it. The plurality of boxes projected onto the patient's arm 7 on the display function as bounding boxes to establish a perimeter within which a vessel is believed to exist in the patient's arm 7 underneath the subject's skin. In an embodiment, the preprocessed image is transformed using one or more image processing techniques on the master computer 90 to a processed image. Processing of the preprocessed image transforms an external image of a patient's arm 7 showing on the skin surface target insertion sites where a predicted vessel of the patient is believed to exist into a processed image of the patient's arm 7 showing a location of one or more actual vessels in contrast to the environment surrounding the patient's actual vessels.

Figure 24:
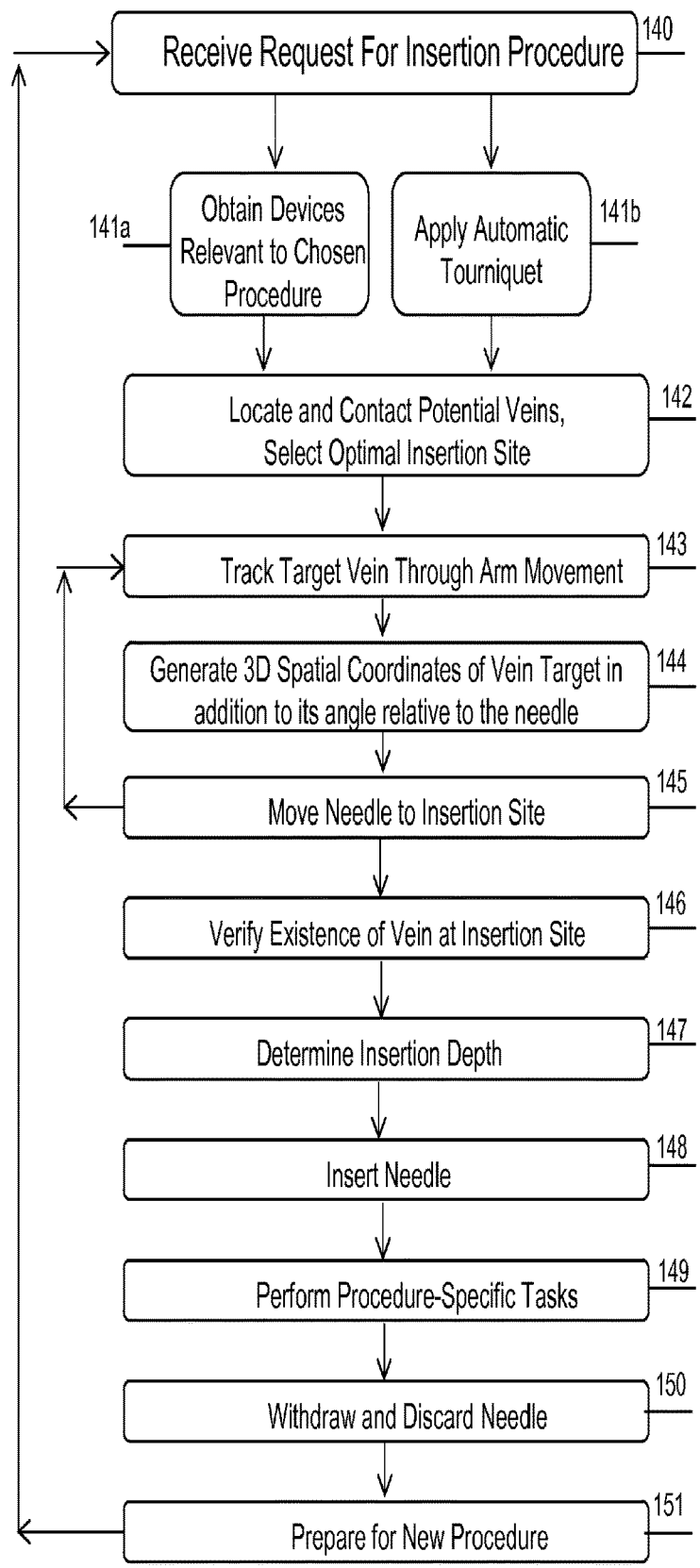
FIG. 24 is a flowchart of a method for use of an embodiment of an autonomous intravenous insertion system of the present disclosure.

In an embodiment, the main software program 115 may provide two functionalities. The first functionality is to provide a GUI 120 through which the user may interact with the system 8. In an embodiment, this entails use of the GUI 120 to control what procedure the system 8 carries out, along with certain parameters to be selected to further describe the details of the procedure. The GUI 120 may also enable the user to oversee the entire insertion process, from real-time monitoring of the medical procedure, to highlighting the targeted insertion location, to providing the user with the option to abort the procedure at any time. The second functionality is to integrate the system's sensors with its state machine. The state machine (the motion control decision engine 111) determines how the robot arm 1 will act at the current time in the procedure. FIG. 24 depicts a flowchart of various states within the state machine, which is described in further detail below.

In an embodiment, as shown in FIG. 23, the system 8 includes a master program 115 having a plurality of modules and a slave control program 114 functioning as a robot controller 1a. In an embodiment, the program 115 is configured to transform real-time sensor data 92 acquired about a location of a patient's vessel into a command to instruct one or more primary actuators 93 to execute autonomous intravenous insertion of a needle. In an embodiment, the program 115 is configured to transform real-time sensor data 92 acquired about a location of a patient's vessel into a command to instruct one or more primary actuators 93 to execute autonomous intravenous insertion of a cannula.

FIG. 23 displays an embodiment diagram of the software architecture and flow of control of the main program designed to run the autonomous needle insertion system 8. A veinbot structure 112 is created within the main program 115 to enable the user to interact with the system 8. Built into the veinbot structure 112 are a camera 61 and laser rangefinder unit 60, a robot connection and command module 113, and a GUI 120 which enables the user to interact with the system 8 by selecting the procedure to be done and monitoring it. Video may be processed in different ways. In an embodiment, the video is processed by a vein processor 112a. In an embodiment, the video is processed by an arm finder 112b. In an embodiment, the video is processed by an elbow finder 112c. Finding the patient's arm 112b and elbow 112c may be needed for both suggesting best insertion sites and automatic target site selection, as they enable the vein selector 112d to choose target veins intelligently. In an embodiment, the vein selector 112d only chooses potential insertion sites inside the arm 112b and near the elbow 112c, which is where needles are typically inserted into the forearm by phlebotomists. The vein selector 112d presents suitable target insertion sites either to the user (in manual mode) or to itself (in automatic mode), awaiting a target to be chosen. Once a target site is chosen, a target vein structure 112e can be created that contains an image of the chosen target. In an embodiment, the selected target is tracked by the vein tracker 110f of the vision system 110. The selected target can be localized in 4 (x, y, z, u) or 6 (x, y, z, u, v, w) coordinates, depending on where in the insertion procedure the system is. When the target is relatively far away, the localization unit 112f typically calculates 4 coordinates of the target site. Upon approaching the target insertion site, the localization unit 112f typically calculates 6 coordinates of the target insertion site for more precise insertion of the needle into the patient's arm 7 at the target insertion site. In an embodiment, the localization unit 112f calculates the coordinates of the target insertion site by combining information from the target tracker 110f of the vision system 110, the target vein structure 112e, and the laser rangefinder 60.

Following tracking and insertion site localization, control commands from the robot connection and command module 113 may be sent to the slave control program 114, such as a command to move closer to the desired target insertion site or a command for inserting the attached medical device into the insertion site. In an embodiment, the slave control program 114 is a static program that awaits commands created by the robot connection and command module 113. When commands are received from the robot connection and command module 113, the slave control program 114 returns a signal to the master program 115 verifying that the correct command was received.

In an embodiment, the master program 115 comprises a control program for permitting an operator of the system 8 to initiate an autonomous intravenous insertion procedure. In various embodiments, the master program 115 is configured to analyze input data 92 acquired by the one or more sensory devices 91, 213 and to transform the input data 92 into a plurality of commands for output to the at least one actuator 93 to instruct the actuator 93 to autonomously perform the medical procedure. In an embodiment, the program may be executed by a user in the vicinity of a patient receiving an intravenous insertion procedure. In an embodiment, the program may be executed remotely from a command center, as long as there exists communication between the master computer 90 and the robot controller 1a.

In an embodiment, the system 8 includes a control panel that enables a user of the system to choose a medical procedure to be performed. In an embodiment, the medical procedure comprises a needle insertion for phlebotomy. In an embodiment, the medical procedure comprises a cannula insertion for phlebotomy. In an embodiment, the medical procedure comprises a cannula insertion for drug administration. In an embodiment, the medical procedure uses one or more VACUTAINER® accessories to perform phlebotomy and drug administration.

It should be noted that, in an embodiment, a plurality of parameters for controlling the system 8 are set depending on the desired medical procedure to be performed. In an embodiment, the plurality of parameters include a parameter for needle insertion for phlebotomy. In an embodiment, the parameter for needle insertion for phlebotomy comprises instructions to load a needle from a needle loading site. In an embodiment, the parameter for needle insertion for phlebotomy comprises instructions to load a tube from a tube loading site. In an embodiment, the tube comprises a new tube. In an embodiment, the parameter for needle insertion for phlebotomy comprises instructions to monitor how full the loaded tubes are. In an embodiment, the parameter for needle insertion for phlebotomy comprises instructions to change the tubes when necessary or desirable. In an embodiment, the parameter for needle insertion for phlebotomy comprises instructions to insert the needle. In an embodiment, the parameter for needle insertion for phlebotomy comprises instructions to extract the needle. It should be appreciated that the instructions to insert and extract the needle can be carried out according to well known needle insertion and extraction procedures. In an embodiment, the needles, tubes, and other equipment used comprise VACUTAINER® brand equipment.

In an embodiment, the plurality of parameters include a parameter for cannula insertion. In an embodiment, the parameter for cannula insertion comprises an instruction to load the cannula from a cannula loading site. In an embodiment, the parameter for cannula insertion comprises an instruction to extract a needle from a center of the cannula.

In an embodiment, the plurality of functions and methods executable by the master computer 90 includes a get range function to instruct the laser rangefinder 60 to obtain a distance, as described above. In an embodiment, the plurality of functions and methods executable by the master computer 90 includes a get video function to instruct the NIR camera 61 to capture a video of a patient's arm 7 in real-time.

In an embodiment, the plurality of functions and methods executable by the master computer 90 includes a process video module or vein processor 112a to employ an image processing technique to transform the video captured of the patient's arm 7 from an image of the patient's arm 7 to an image of the patient's arm 7 showing useful information pertaining to a plurality of target insertion sites where a vessel of the patient exists. In an embodiment, the vein processor 112a transforms the preprocessed image of the patient's arm 7 acquired by the frame grabber 110a into a processed image of the patient's arm 7. Combined with information from the arm finder 112b that discards visual information not inside the patient's arm 7 and the elbow finder 112c that finds the patient's elbow region, the processed image of the patient's arm 7 is passed to the vein selector 112d. In the vein selector 112d, a plurality of bounding boxes may be projected onto the image of the patient's arm 7, indicating target insertion sites for inserting a medical device into a vessel of the patient. In an embodiment, the processed image of the patient's arm 7 includes an image of the vessel of the patient featured in a first color which distinguishes the vessel from structures in the environment surrounding the vessel which are featured in a second, a third, a fourth, or any number of additional colors sufficient to show a contrast between the vessel and other structures in the environment surrounding the vessel.

In an embodiment, the plurality of functions and methods executable by the master computer 90 includes using the vein selector 112d to allow the master computer 90 to autonomously select a target insertion site for automatically inserting a medical device tool 212 into a patient's vessel while the system 8 is operating in the automatic mode of operation.

In an embodiment, the plurality of functions and methods executable by the master computer 90 includes using the vein tracker 110f for tracking the target insertion site in real-time. In an embodiment, the vein tracker 110f tracks the two-dimensional coordinates of the optimal insertion site in real-time. In an embodiment, the vein tracker 110f tracks the two-dimensional coordinates of the vessel in real-time. In an embodiment, the vein tracker 110f tracks the orientation of the vessel in real-time.

In an embodiment, the plurality of functions and methods executable by the master computer 90 build a target vein structure 112e that holds information about the targeted insertion site, including, but not limited to, its appearance, size, shape, location, orientation, and topography.

In an embodiment, the plurality of functions and methods executable by the master computer 90 includes a vein localization unit 112f for generating the three-dimensional coordinates of the patient's vessel and the orientation of the patient's vessel. This functions by passing the coordinates of the target vessel in the camera frame provided by the vein tracker 110f with information from the rangefinder reader 110c into a function inside the localization unit 112f with knowledge of how distance to the target and pixels correspond to three-dimensional space.

In an embodiment, the plurality of functions and methods executable by the master computer 90 includes a module to send commands and receive information from the slave control program 114 for sending commands to the at least one actuator 93 to autonomously perform a medical procedure and for receiving sensor data 92 acquired in real-time pertaining to the at least one actuator 93 so that the master computer 90 can process the sensor data 92 in real-time to make sure that the medical procedure is successful.

FIG. 24 is a flowchart of an embodiment operational procedure of the autonomous intravenous insertion system 8, beginning with a request for a certain procedure, and following through until the procedure has been successfully carried out or aborted. FIG. 24 represents one insertion procedure as a sequence of stages. The sequence begins with stage 140, where the system 8 waits to receive a request to perform an insertion procedure on a patient. Once the patient is ready to have the procedure performed, the system 8 is prompted to obtain medical device tools 212 needed for the procedure in step 141a. Simultaneously, the system 8 applies the automatic tourniquet cuff 5 in step 141b so that the patient's forearm is stabilized and the vein within the forearm become more visible. Once the medical device tool 212 relevant to the procedure has been obtained, the system 8 highlights potential insertion sites and, depending on the mode of operation, either selects a target site automatically or receives input from the user regarding the target insertion site in step 142. With the site selected, the system tracks the site in step 143, generates three-dimensional spatial coordinates and an angle relative to the medical device tool 212 in step 144, and moves continuously towards the insertion site until the medical device tool 212 is directly above the insertion site in step 145. If an ultrasound device 64 is included in the system 8, step 146 allows the system 8 to verify that a vein is indeed under the target insertion location, and in step 147 the system 8 determines the insertion depth. Once step 147 is complete, the system 8 inserts the butterfly needle 41, catheter 22, or other tool 80 in step 148. In step 149, the system 8 proceeds to carry out procedure-specific tasks, such as engaging or disengaging vacuum tubes in the case of drawing blood. When the procedure is complete the system 8 discards the used butterfly needle 41, catheter 22, or other tool 80 in step 150 and prepares itself to carry out a new procedure in step 151.

In an embodiment, the request received from the operator to perform an insertion procedure comprises an operator command to instruct the autonomous intravenous insertion system to perform a needle insertion for phlebotomy. In an embodiment, the needle insertion for phlebotomy can be performed using VACUTAINER® blood drawing equipment. In an embodiment, the request received from the operator to perform the insertion procedure comprises an operator instruction to operate the autonomous intravenous insertion system to perform a cannula insertion for phlebotomy. In an embodiment, the request received from the operator to perform an insertion procedure comprises an operator instruction to operate the autonomous intravenous insertion system to perform a cannula insertion for administration of a drug or for blood drawing. In an embodiment, the request received from the operator to perform an insertion procedure comprises an operator instruction to operate the autonomous intravenous insertion system to perform a syringe insertion for administration of a drug.

During step 140, the user may dictate the mode of selecting a target: automatic, semi-automatic, or manual. Automatic mode means the targeted vessel is selected entirely by the program, based on shape analysis and pre-programmed parameters to identify good insertion sites. Semi-automatic mode means the program will analyze the entire image and return in highly-distinguishable bounding boxes all sites it believes are apt for needle insertion. In this mode, the user must click within the box or on the vessel of interest on the video display 121 before the arm makes any movement. Manual mode refers to the user manually selecting the targeted vessel by clicking and dragging around the targeted site. From there, the program will figure out the location of the targeted vessel, or if it determines that no vessel exists there, it will prompt the user if he would like to pick a new target.

In an embodiment, once the request to perform an insertion procedure is received from the operator of the system at step 140, operation of the autonomous intravenous insertion system of the present disclosure proceeds to step 141a and step 41b. Step 141a comprises obtaining a medical device tool 212 to be used to perform the insertion procedure. It should be appreciated that the medical device tool 212 obtained to perform the insertion procedure may depend on the particular insertion procedure to be performed. In an embodiment, a plurality of medical device tools 212 for performing the insertion procedure may be obtained. Step 141b comprises activation of the system's automatic tourniquet cuff 5 and wrist stabilizing cuff 6, so as to increase the size and visibility of the veins and demobilize the patient's arm.

Once the medical device tools 212 needed to perform the insertion procedure are obtained, the tools 212 are then attached to an actuator 93 of the autonomous intravenous insertion system. In an embodiment, the medical device tool 212 used to perform the insertion procedure is manually attached by the operator of the system 8. In an embodiment, the operator comprises a skilled technician. In an embodiment, the operator comprises an unskilled technician. In an embodiment, the medical device tool 212 used to perform the insertion procedure is automatically attached by one of the actuators 93. In an embodiment, the medical device tool 212 is automatically attached by the robot. The tool changers 9 and 10 on the robot arm 1 change the tool 212 used to grab the medical device based on the desired procedure. When the appropriate tool changer is in place, the medical device tools 212 needed to be used for the procedure are retrieved and fixed in place by the tool changer grabbing it. Both of these procedures may be done autonomously.

In an embodiment, the autonomous intravenous insertion system 8 of the present disclosure includes at least one loading station 11, 12 for loading and fastening the medical device tool 212 to be inserted to the robot arm 1. In an embodiment, the at least one loading station 11, 12 includes a feeding mechanism for loading the medical device tool 212 to be inserted to the robot arm 1. In an embodiment, the feeding mechanism is operable to load and fasten at least one ancillary device to the robot arm 1. In an embodiment, the loaded medical device may be gripped by the tool via pneumatic fasteners.

In an embodiment, the medical device tool 212 to be inserted comprises a butterfly needle 41. In an embodiment, the medical device tool 212 to be inserted comprises a syringe. In an embodiment, the medical device tool 212 to be inserted comprises a cannula. In an embodiment, the medical device tool 212 to be inserted comprises a blood drawing tube 78. In an embodiment, the blood drawing tube 78 comprises VACUTAINER® blood drawing equipment. In an embodiment, the medical device tool 212 to be inserted comprises a catheter 22. In an embodiment, the catheter 22 comprises BD Nexiva's Closed IV Catheter System. It should be appreciated that medical device tools 212 having similar functionalities to the medical device tools 212 disclosed herein may also be used.

In an embodiment, the at least one ancillary device used to perform the insertion procedure is also obtained and subsequently positioned to perform the insertion procedure by the tool changer 9, 10. It should be noted that the ancillary devices used to perform the insertion procedure depend on the insertion procedure to be performed.

Step 142 comprises, in an embodiment, identifying, using a master computer 90 running the software described herein for identifying veins, a target insertion site for insertion of the medical device tool 212 into a vessel of the patient's arm 7 during the insertion procedure. To identify the target insertion site for insertion of the medical device tool 212, such as a butterfly needle 41 or catheter 22, into a vessel, the system 8 uses one or more primary sensors 91, such as an NIR camera 61 or a laser rangefinder 60, to acquire real-time sensor data 92 relating to the patient's vessels. In an embodiment, the system 8 may also use secondary sensors 213 such as a second camera if desired. In an embodiment, the autonomous intravenous insertion system 8 uses an infrared imaging technique and a video processing technique, such as, for example, the ones described above, to automatically highlight a plurality of potential insertion locations on a video display 121 of the system 8 for the operator of the system to visualize. In an embodiment, in automatic mode, the system 8 automatically identifies the target insertion site for automatic insertion of the medical device tool 212 into the vessel of the patient's arm 7. In an embodiment, in semi-automatic mode, the system 8 allows the operator of the system to manually select the target insertion site from among the plurality of potential insertion locations highlighted on the display.

In an embodiment, the autonomous intravenous insertion system 8 automatically highlights the plurality of potential insertion locations for the operator of the system to select for the insertion procedure using a program configured to identify a vessel in the patient's arm 7. In an embodiment, the program operates in a semi-automatic mode in which the operator may select the target insertion site for insertion of the medical device tool 212 into the patient's vessel from among the plurality of insertion locations highlighted on the video display 121 by using a mouse or other input device to click one of the plurality of insertion locations highlighted for the operator on the display. In an embodiment, the program can also be run in autonomous mode, where the target insertion site for insertion of the medical device tool 212 into the patient's vessel is automatically and intelligently selected by the system 8 itself. In an embodiment, the program directs ample illumination onto the patient's arm 7 and uses near-infrared imaging techniques and contrast enhancement algorithm to obtain contrast of the patient's vessel against the environment surrounding the vessel.

In an embodiment, once the target insertion site for insertion of the medical device tool 212 into the vessel of the patient's arm 7 is identified and selected at step 142, either autonomously or via user input, operation of the autonomous intravenous insertion system 8 of the present disclosure proceeds to step 143.

In an embodiment, step 143 comprises tracking, using the at least one sensor 93, such as an NIR camera 61, the target insertion site. In an embodiment, tracking the target insertion site occurs in real-time. In an embodiment, automatically tracking the target insertion site in real-time helps ensure that the actuators 93 guide the medical device tool 212 to be inserted in the pre-determined location along an optimal insertion path and an optimal orientation toward and into the patient's vessel.

A video camera 61 outfitted with a bandwidth filter permitting light in the range of 720 nm to 780 nm to pass may be used to take pictures of the forearm. Such filter highlights the appearance of veins in the image since blood (hemoglobin) preferentially absorbs light in the NIR range. Thus, veins will appear comparatively darker through our camera than through a standard white-light-sensing camera. An insertion site may be identified and localized through the processing of image data 92 received from the single NIR camera 61. The original input image is binarized through a series of processing steps and then fed into a trained vein classifier. Before the image is fed into the classifier, some preprocessing is done to calculate a series of features having to do with each white blob in the processed image is calculated. These features are related to the size, shape, thickness, length, and angle relative to the entire arm of each blob. Based on these features, the classifier makes a guess as to whether the blob is a vein or not. Together with the arm finder 112b and elbow finder 112c, a scoring module ranks the best veins, and presents them to the user in a highly distinguishable manner. If the program is running in automatic mode, the vein with the best score is chosen as the target vein. Otherwise, the program waits until the user selects a suitable target.

Once a target has been selected, it is continuously tracked and ultimately localized in three-dimensional space. Tracking requires not losing the site within the image frame, and this is done with the video processing system. This way, regardless of patient movement, the system knows the location of the targeted site. Simultaneously, the robot arm 1 can be commanded to move in the direction of the target site using visual feedback. The path taken leads the laser rangefinder 60 directly over the insertion site, at which point the target location in three-dimensional space can be determined. The topography of the around the targeted site is also mapped using the laser rangefinder 60 so the robot arm 1 can be adjusted accordingly. The medical device tool 212 can thus be accurately positioned prior to inserting the tool 212 without accidentally running into the patient's skin.

In an embodiment, the system 8 tracks the target insertion location instead of tracking the medical device tool 212 to be inserted for a number of reasons. In an embodiment, the system 8 remains aware of the position of the medical device tool 212 to be inserted throughout the insertion procedure, and thus specifically tracking the medical device tool 212 may be redundant. Since the system 8 is aware of the position of the medical device tool 212, tracking the target insertion site relative to the position of the medical device tool 212 to be inserted allows the system 8 to precisely position the medical device tool 212 in close proximity to the target vessel at the target insertion site. This is desirable where a movement of the patient can cause the position of the medical device tool 212 to suddenly change relative to the target insertion site. Thus, tracking the target insertion site allows the system to update in real-time, using feedback acquired by the one or more primary sensors 91, the position of the target insertion site, as well as the optimal insertion path and orientation for the medical device tool 212 to be inserted.

In an embodiment, the target insertion site for the medical device tool 212 to be inserted into the patient's vessel is automatically tracked in real time with respect to a movement of any kind of the patient. In an embodiment, the target insertion site is automatically tracked in real time with respect to an arm movement of the patient. In an embodiment, the target insertion site is automatically tracked in real time with respect to a voluntary arm movement of the patient. In an embodiment, the target insertion site is automatically tracked in real time with respect to an involuntary arm movement of the patient. In an embodiment, the target insertion site is automatically tracked in real time with respect to a movement of the patient's body that results in a repositioning of the patient's arm 7. In an embodiment, the target insertion site is automatically tracked in real time with respect to repositioning of the patient or the patient's arm 7. In an embodiment, the system may be programmed to abort the procedure, if an arm is no longer seen within the field of view of the NIR camera 61.

In an embodiment, the target insertion site tracked in real-time by the system 8 comprises a perimeter on a skin surface of the patient in close proximity to a vessel in the patient's arm 7 underneath the skin surface. In an embodiment, the target insertion site is tracked in real-time by the system 8 by projecting a bounding box onto an image of the patient's arm 7. In an embodiment, the bounding box encompasses a perimeter on the skin surface of the patient in close proximity to the vessel underneath the skin surface of the patient's arm 7.

In an embodiment, subsequent to or concomitantly with real-time tracking of the optimal insertion site at step 143, operation of the autonomous intravenous insertion system of the present disclosure proceeds to step 144.

Step 144 comprises, in an embodiment, generating three-dimensional coordinates of the patient's vessel. This can be done by using the master computer 90 to process the sensor 92 data acquired by the one or more sensors 91, 213, such as the laser rangefinder 60 and at least one NIR camera 61. In an embodiment, the three-dimensional coordinates of the targeted vessel are used by the master computer 90 to determine an optimal insertion path and an optimal orientation for the medical device tool 212 to be inserted into the patient's vessel. The system 8 generates the three-dimensional coordinates of the optimal insertion path and the optimal orientation continuously throughout the insertion procedure. The system 8 continuously updates the three-dimensional coordinates of the target insertion site in real-time to prevent a spontaneous movement of the patient from making the insertion procedure unsuccessful.

In an embodiment, the system 8 is equipped with a laser measurement system precise to within 10 μm. The system 8 is calibrated to convert pixels to millimeters as a function of depth. A conversion function may be used to determine physical distances from pixel dimensions in the image. This conversion function may be based on the fixed geometry of the camera 61 and lens, and the variable distance of the lens to the target object is obtained by the laser measurement system. After the target insertion site is identified, the robot arm 1 may be commanded to move the laser rangefinder 60 to a position several centimeters above the target insertion site using feedback from at least one imaging device as a guide. When the laser rangefinder 60 is in position and pointing at the target insertion site, the robot arm 1 may calculate the topography of the insertion site with the laser rangefinder 60, so that it may orient itself in such a way as to not be obstructed by the patient's arm 7 during the insertion procedure. Next, the robot arm 1 may orient itself in the appropriate fashion, and may be commanded to move closer to the insertion target, using feedback from the imagine device and laser rangefinder 60 to place the medical device tool 212 in the position where the insertion path will begin. After the target insertion site and orientation are identified, the robot arm 1 is commanded to move the laser rangefinder 60 directly over the target insertion site using feedback from the at least one sensor 91, 213 as a guide. In an embodiment, the at least one sensor 91, 213 used to provide feedback to the system to command the robot arm 1 to move the laser rangefinder 60 over the target insertion site comprises an imaging device. In an embodiment, the imaging device is a camera 61. In an embodiment, the imaging device is an NIR camera 61. In an embodiment, the imaging device is an ultrasound imaging device 64. Once the depth needed to reach the vessel underneath the skin surface of the target insertion site is found, its three-dimensional coordinates are generated and transformed into a command to instruct the at least one actuator 93 to move the medical device tool 212 to be inserted to this position.

In an embodiment, concomitantly with real-time tracking of the target insertion site at step 143 and the generation of the three-dimensional coordinates at step 144, operation of the autonomous intravenous insertion system 8 of the present disclosure continues at step 145. As illustrated in FIG. 24, step 145 comprises, in an embodiment, positioning, using the at least one actuator 93, the medical device tool 212 in close proximity to the patient's vein, wherein when the tool 212 is in close proximity to the patient's vein, the tool 212 is preferably positioned at the beginning of a desired insertion path in the desired orientation.

Due to patient's movement during the insertion procedure, a control program on the maser computer 90 may be configured to evaluate the target insertion site in real-time so that when a movement of the patient's arm 7 displaces the identified target insertion site with respect to the position of the medical device tool 212 to be inserted, the control program sends in real-time updated three-dimensional coordinates of the target insertion site to a robot controller 1a so that the at least one actuator 93 can be repositioned for the medical device tool 212 to be inserted through the target insertion site. That is, the robot arm 1 repositions itself in the optimal orientation so the tool 212 is in line with the targeted vessel. The medical device tool 212 can thus be inserted through the target insertion site along an updated optimal insertion path and an updated target insertion site so that the medical device tool 212 is inserted safely and properly into the patient's vessel.

Steps 143 through 145 may be carried out repeatedly in a loop until the system has determined it has reached the target insertion site.

In an embodiment, at least prior to step 147, operation of the autonomous intravenous insertion system of the present disclosure performs step 146. Step 146 comprises, in an embodiment, verifying, using the at least one primary sensor 91, the existence of the vein underneath the target insertion site. In an embodiment, verifying that a vessel lies underneath the target insertion site ensures a safe insertion procedure. In an embodiment, verifying that a vessel lies underneath the target insertion site ensures a successful insertion procedure. In an embodiment, verifying that a vessel lies underneath the target insertion site ensures an accurate insertion procedure. In an embodiment, verifying that a vessel lies underneath the target insertion site reduces the risk of an improper insertion procedure. In an embodiment, verifying that a vessel lies underneath the target insertion site reduces the risk of an error during the insertion procedure. In an embodiment, verifying that a vessel lies underneath the target insertion site decreases the likelihood of having to repeat the insertion procedure on the patient.

In an embodiment, at step 146 the autonomous intravenous insertion system 8 may deploy an ultrasound device 64 to verify the existence of a vessel in the target location underneath the target insertion site beneath the patient's skin surface. In an embodiment, the system 8 autonomously operates an ultrasound device 64 using the program on the master computer 90 to instruct the at least one actuator 93 to perform the ultrasound imaging technique for precise positioning of the ultrasound device 64 to obtain an ultrasound image of the patient's vessel underneath the target insertion site. In an embodiment, interpretation of the ultrasound image for verification that a vessel is in the specified location is performed by the ultrasound processor and vein verification system 65 of the system 8 of the present disclosure autonomously through.

The ultrasound image data may be processed using standard noise filtering algorithms, and objects in the image are identified by the intensity of pixels comprising them. Specifically, veins will appear as dark, approximately circular objects in the image with radii of a few millimeters. Converting the images to binary images and excluding objects of incorrect size and shape will highlight these vein cross-sections, and allow the computer to determine their depth and diameter.

In an embodiment, the user may view the ultrasound image generated by the ultrasound device 64 and interpret the ultrasound image to verify that the vessel is in the specified location. In an embodiment, the ultrasound imaging device 64 is in a retracted position. In the retracted position, the ultrasound imaging device 64 does not obstruct other sensors 91, 213 attached to the at least one actuator 93. In an embodiment, during the verification step, the ultrasound imaging device 64 is moved from its retracted position into a position suitable both for verifying the existence of the vessel within the patient's arm 7 underneath the skin surface of the target insertion site and for measuring a depth of the vessel underneath the skin surface of the target insertion site. In an embodiment, when the ultrasound imaging device 64 is moved into the position suitable for verification and measurement of the vessel, other sensors 91, 213 attached to the at least one actuator 93 may be obstructed from acquiring data 92 relating to the patient's arm 7 and the vessel. However, it should be appreciated that at least one of the sensors 91, 213, such as the NIR camera 61, remains operable to track the patient's arm 7 in real-time and to detect movement of the patient's arm 7. In an embodiment, the ultrasound imaging device 64 includes an ultrasound probe. In an embodiment, an ultrasound probe of the ultrasound imaging device 64 verifies the existence of the vessel beneath the skin surface of the target insertion site on the patient's arm 7. In an embodiment, the ultrasound device 64 validates the real-time data 92 acquired by the at least one sensor 91 in earlier steps.

Step 147 comprises, in an embodiment, determining, using either vein intensity, feedback from the ultrasound device 64, or preprogrammed instructions, an insertion depth for the medical device tool 212 to be inserted into the patient's vessel along the optimal insertion path. In an embodiment, the depth of the vessel underneath the target insertion site is determined using an ultrasound signal or image obtained during step 146 through the ultrasound processor and vein verification system 65 previously described. In an embodiment, the insertion depth is preprogrammed but also monitored using feedback from the insertion procedure, such as visual information indicating the vessel has been punctured, or force feedback along the axis of the medical device tool 212. In the case where the insertion depth is preprogrammed, monitoring the insertion depth with feedback is done to ensure the procedure is safe.

In an embodiment, at least prior to the step of inserting at step 148, the method for autonomous insertion of a medical device tool 212 into a vessel of a patient to be treated comprises generating, using the master computer 90, an updated optimal insertion path and an updated optimal orientation for the medical device tool 212 to be inserted based on a movement of the patient detected while using the at least one sensor 91 to track the target insertion site in real-time.

In an embodiment, the master program 115 transforms in real-time the updated desired insertion path and the desired orientation for the medical device tool 212 to be inserted into a command to instruct the at least one actuator 93 to automatically reposition the medical device tool 212 in the updated optimal insertion path and the optimal orientation to insert the medical device tool 212 into the patient's vessel.

In an embodiment, subsequent to the step of determining at step 147, operation of the autonomous intravenous insertion system 8 of the present disclosure proceeds to step 148.

As illustrated in FIG. 24, step 148 comprises, in an embodiment, inserting, using the at least one actuator 93, the medical device tool 212 into the patient's vessel at the target insertion site. In an embodiment, the medical device tool 212 is inserted in the desired orientation and along the desired insertion path. In an embodiment, the medical device tool 212 is inserted in a guided and steady manner into the vessel of the patient. In an embodiment, the medical device tool 212 is inserted in a straight line path into the vessel. In an embodiment, the medical device tool 212 is inserted in a straight line path into the vessel through the target insertion site to a depth equivalent to the depth determined during step 147. In an embodiment, the vessel of the patient comprises a vein. In an embodiment, the vessel of the patient comprises a superficial vein. In an embodiment, the vessel of the patient comprises a deep vein. In an embodiment, the vessel of the patient comprises a subcutaneous vein. In an embodiment, the medical device tool 212 comprises a butterfly needle 41. In an embodiment, the medical device comprises a cannula. In an embodiment, the medical device tool 212 comprises a catheter 22.

In an embodiment, subsequent to the step of inserting at step 148, operation of the autonomous intravenous insertion system 8 of the present disclosure proceeds to step 149 which comprises performing one or more tasks pertaining to a medical procedure to be performed in connection with the insertion procedure to complete the medical procedure. In an embodiment, the autonomous intravenous insertion system 8 of the present disclosure includes an auxiliary device connected to the robot arm 1 for performing the one or more tasks pertaining to the medical procedure to be performed in connection with the insertion procedure. In an embodiment, the one or more tasks to be performed by the auxiliary device comprises engaging a blood drawing tube 78. In an embodiment, the one or more tasks to be performed by the auxiliary device comprises disengaging a blood drawing tube 78. In an embodiment, the one or more tasks to be performed by the auxiliary device comprises swapping a first blood drawing tube 78 with one or more blood drawing tubes 78. In an embodiment, the blood drawing tube 78 comprises a VACUTAINER® tube.

In an embodiment, subsequent to at least the step of inserting at step 148, operation of the autonomous intravenous insertion system 8 of the present disclosure continues to step 150 which comprises automatically withdrawing the medical device tool 212 for subsequent disposal of the medical device tool 212 for sanitary purposes. In an embodiment, withdrawal of the medical device tool 212 comprises extracting the tool 212 by retracing the tool 212 outward along the optimal insertion path used to insert the medical device tool 212 into the vessel.

In an embodiment, once the medical device tool 212 is withdrawn and discarded into the disposal unit 96 at step 150, operation of the autonomous intravenous insertion system 8 proceeds to step 151. At step 151, the autonomous intravenous insertion system 8 returns to step 140 and waits to receive instructions from an operator of the system 8 to request an insertion procedure to be performed on a patient.

Figure 25:
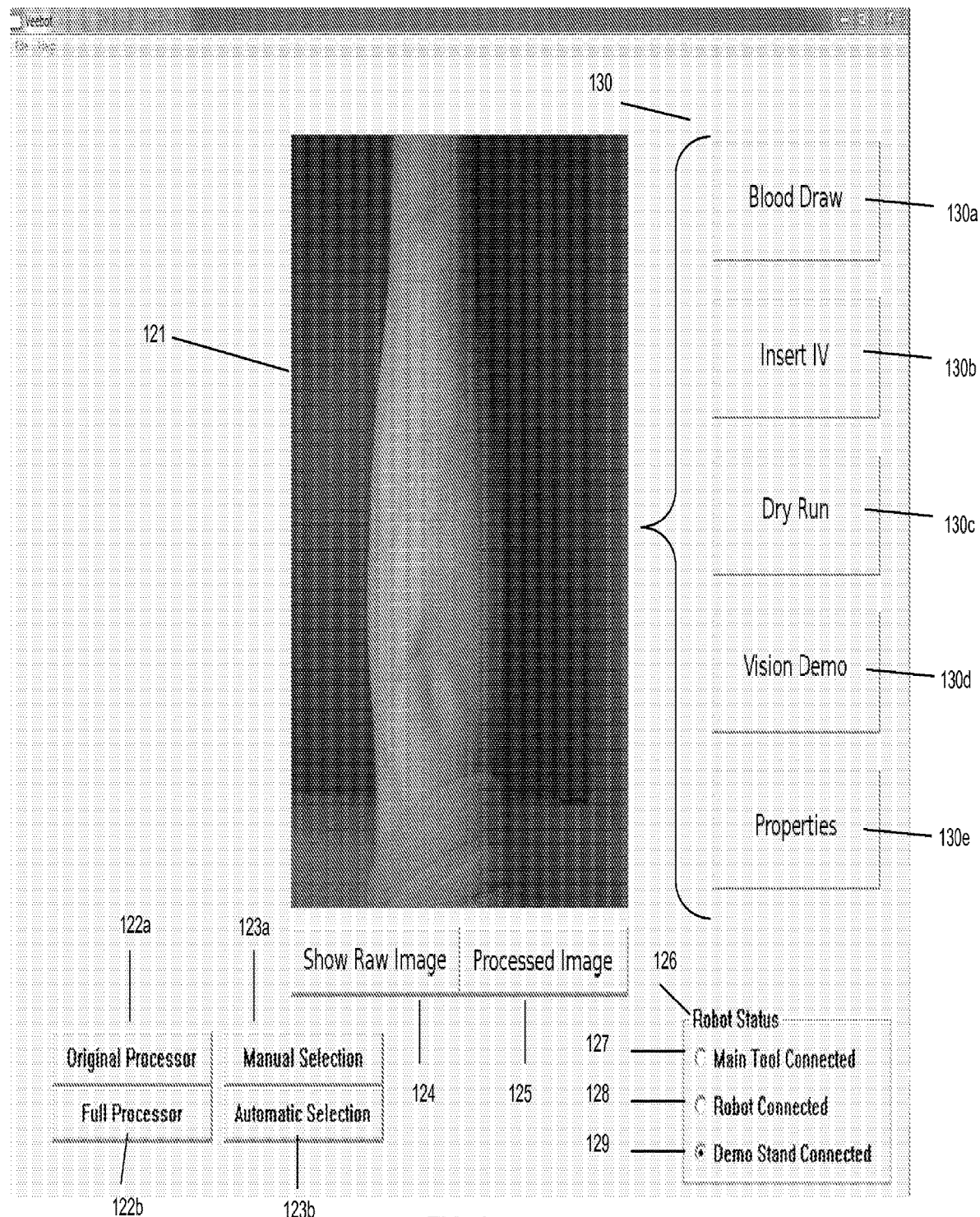
FIG. 25 is a screenshot of an interface of an embodiment of an autonomous intravenous insertion system of the present disclosure.
Figure 26:
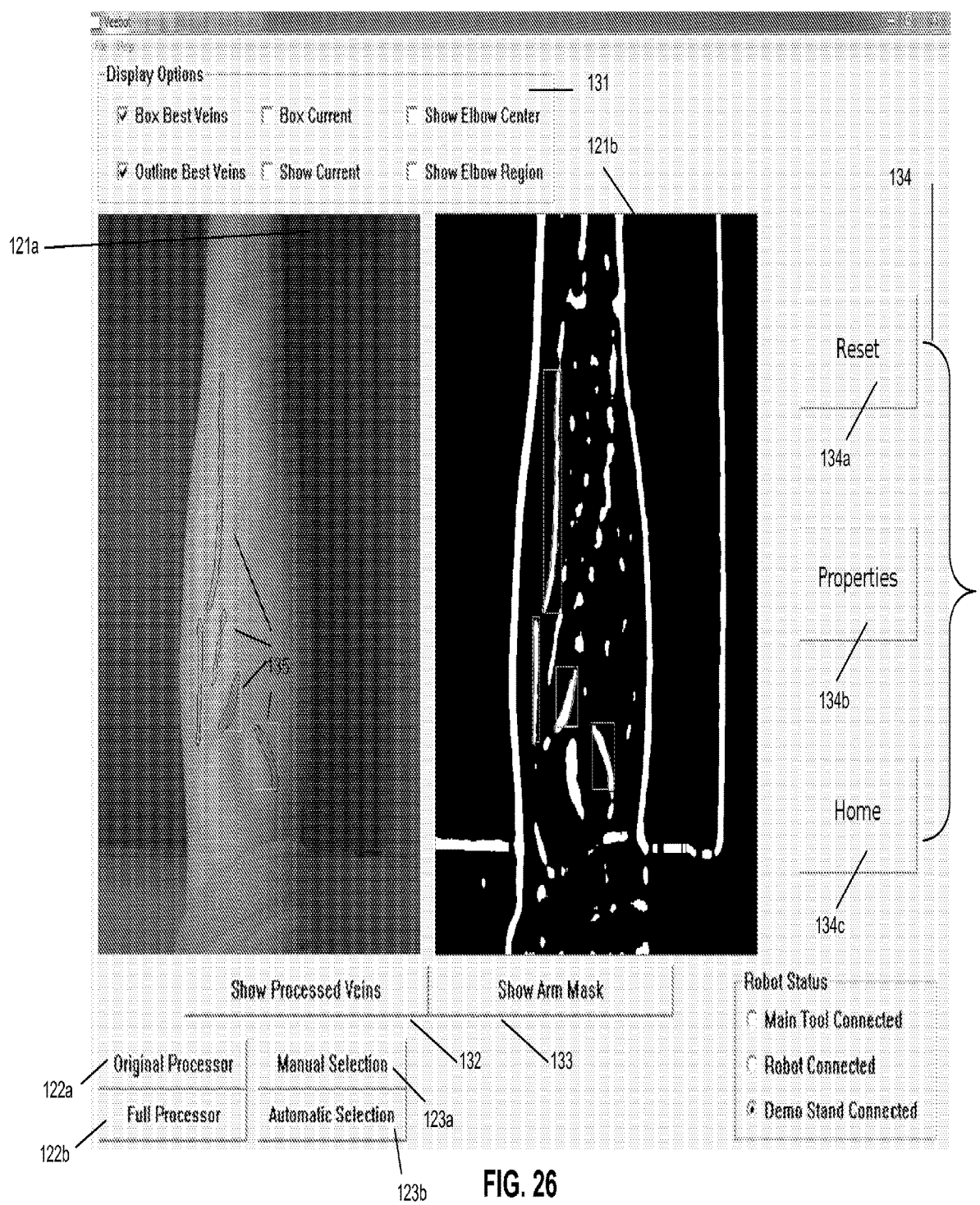
FIG. 26 is a screenshot of an interface of an embodiment of an autonomous intravenous insertion system of the present disclosure.
Figure 27:
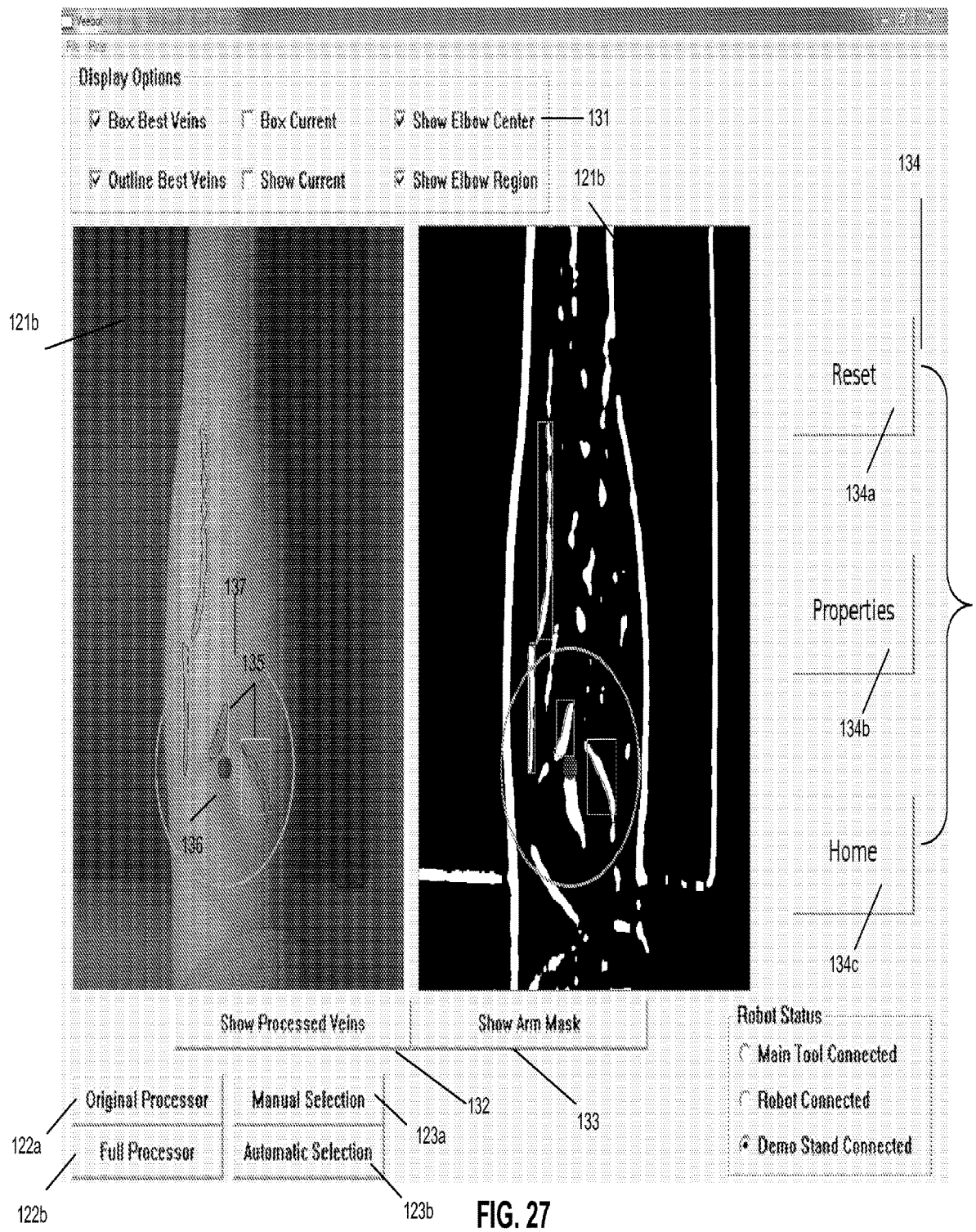
FIG. 27 is a screenshot of an interface of an embodiment of an autonomous intravenous insertion system of the present disclosure.

FIG. 25, FIG. 26 and FIG. 27 show an embodiment of the GUI 120 for the autonomous intravenous insertion system 8 of the present disclosure. In an embodiment, the GUI 120 is displayed on a touch screen connected to the system 8. However, the GUI 120 may be presented on any type of screen as long as the user has means to interact with it. FIG. 25 illustrates an embodiment of the home screen. Referring to FIG. 25, the video input from the NIR camera 61 is displayed in the video display 121. The user can select from one of two processors, original processor 122a or full processor 122b. In an embodiment, the original processor 122a looks for short, stubby vein-like blobs in the processed image. The full processor 122b selects veins using a machine learning algorithm which has been trained to identify forearm veins in conjunction with a module that keeps track of veins found over time. In an embodiment, keeping track of veins over time may help to eliminates the chance of false-positives from being selected. The user may also select how the user intends to find a target insertion site. "Manual selection" 123a denotes that the user will select the site himself from clicking and dragging on the target site or clicking on a suggested target. "Automatic selection" 123b will select the target insertion site automatically for the user. Buttons 124 and 125 allow the user to switch between viewing modes, raw image 124 or processed image 125. The status of the robot arm 1 is also displayed to the user at robot status indicator box 126. The main sensor tool connected option 127 indicates that the main sensor tool containing the NIR camera 61 and the laser rangefinder 60 on the robot arm 1 are connected and working. The robot connected option 128 indicates that the robot motor controller is on and the robot is ready for actuation. In an embodiment, for insertion procedures, both "Main Tool Connected" 127 and "Robot Connected" 128 are marked, and "Demo Stand Connected" 129 is not marked. On the other hand, "Demo Stand Connected" 129 is marked when simply testing the system's vein finding, as shown in the screen shot in FIG. 25. From the home screen, the user can also select from a number of actions 130 the robot arm 1 can perform. In an embodiment, options are "Draw Blood" 130a indicating the system will carry out a blood drawing procedure, "Insert IV" 130b indicating the system will carry out an IV insertion procedure, "Dry Run" 130c indicating the user wants to test the vision system 110 vein selection and tracking capabilities while the robot approaches the target site, "Vision Demo" 130d indicates the user wants to demonstrate or test the vein processor's capabilities, and "Properties" 130e allows the user to change vision processing properties.

In an embodiment, upon selecting "Vision Demo" 130d from the actions 130, the user is presented with the screen as shown in FIG. 26. In the screen shot of FIG. 26, the processor mode is "Full Processor" 122b and the selection mode is on "Manual Selection" 123b. As shown, the system 8 suggests potential target insertion sites to the user by placing bounding boxes 135 around the sites. To select a target insertion site, the user may either click the bounding box with a target vein inside it or click and drag a box over the desired target in either of the video displays shown 121a, 122b. Once a target insertion site is selected, it is tracked in real time. To reset the target insertion site, the user can use the "Reset" button 134a in one of the possible actions 134, shown on the right in FIG. 26. In an embodiment, other actions 134 include the "Properties" button 134b, which enables the user to alter the processing properties, and the "Home" button 134c which takes the user to the home screen.

The video display 121 displays a processed vein image. In an embodiment, the system 8 provides such processed image to the vein identification system 110d, discussed above. Options "Show Processed Veins" 132 and "Show Arm Mask" 133 enable the user to see either the processed vein image (shown above) or the "arm mask" output by the arm finder (reference 112b not shown here) which outlines the patient's arm 7 in real time. Atop the image lies a "Display Options" list 131 that enables the user to see various objects found by the vein identification system.

FIG. 27 shows an embodiment screen shown in response to selecting options from the Display Options list 131. Suitable veins are outlined by providing bounding boxes outlining target vein suggestions 135 about them. In addition, the elbow center estimate is displayed by a dot 136, which gives the user an idea of the point around which to look for target veins. More formally, the "Show Elbow Region" option displays a border around the region in which to look for target sites by drawing a boundary 137 around the region. Options "Box Current" and "Show Current" enable the user to bypass the software module that keeps track of veins found over time and displays every vein as estimated by the learned vein model.

The systems and methods disclosed herein are controlled by a computer configured to acquire using at least one sensory device real-time data relating to a patient and to transform the real-time data into information useful to select an target insertion site for a target vein, and to transform the real-time data into a command output to at least one actuator to instruct the actuator to autonomously perform an insertion procedure wherein a medical device, such as a needle or a cannula is inserted into the target vein at the target insertion site. In an embodiment, the computer is a master computer configured to communicate with a robot arm at least via an Ethernet port. The master computer running the control program can be thought of as a stand-alone unit that can communicate with the robot arm in myriad ways including, but not limited to, Ethernet communication, serial communication, or communication over a wireless network.

Figure 28:
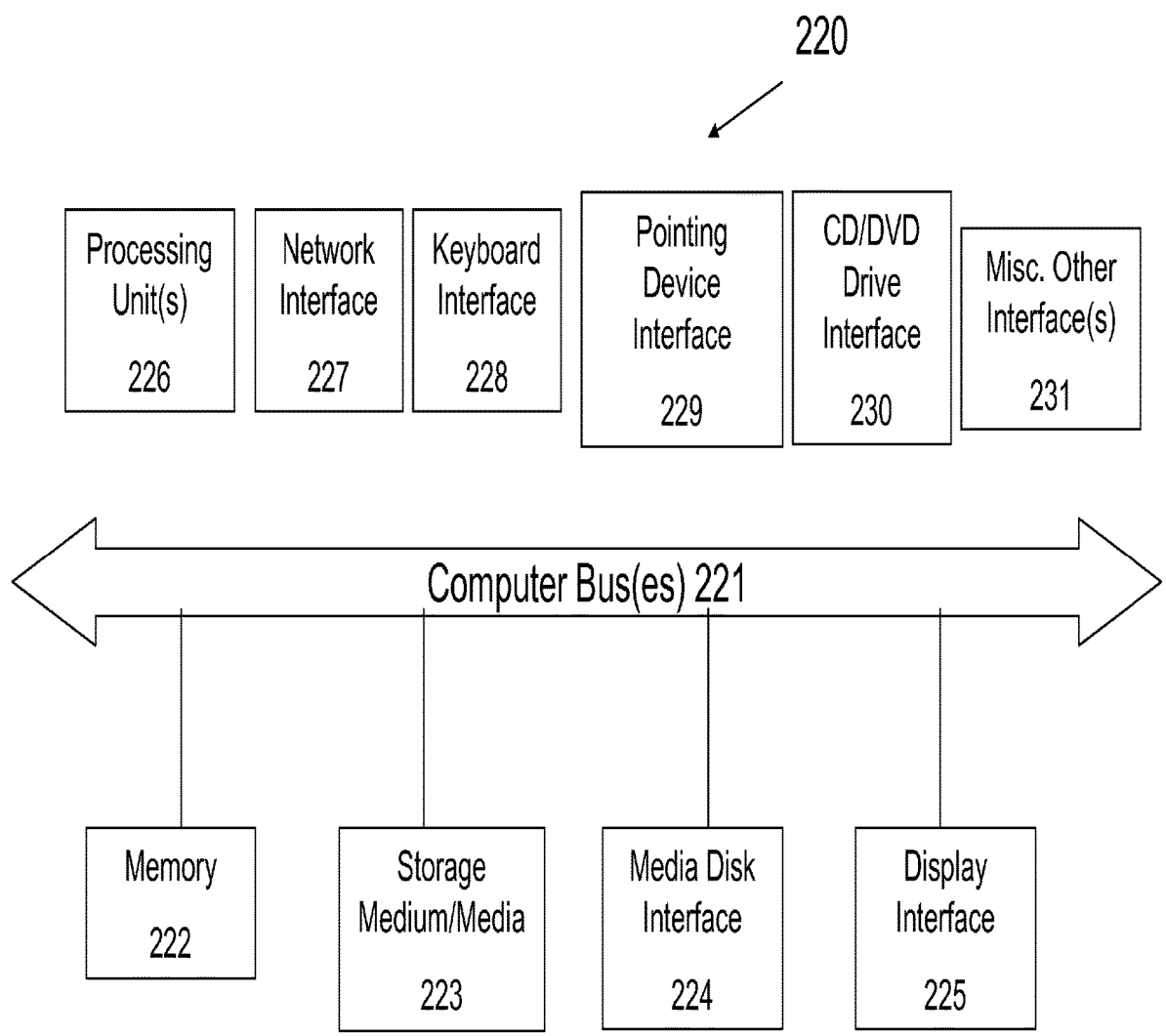
FIG. 28 is a block diagram illustrating an internal architecture of a computer in accordance with an embodiment of the present disclosure.

FIG. 28 is a block diagram illustrating an internal architecture of an example of a computer, such as the master computer 90, in accordance with one or more embodiments of the present disclosure. A computer as referred to herein refers to any device with a processor capable of executing logic or coded instructions, and could be a server, personal computer, set top box, smart phone, pad computer or media device, to name a few such devices. As shown in the example of FIG. 28, internal architecture 220 includes one or more processing units (also referred to herein as CPUs) 226, which interface with at least one computer bus 221. Also interfacing with computer bus 221 are persistent storage medium/media 223, network interface 227, memory 222, e.g., random access memory (RAM), run-time transient memory, read only memory (ROM), etc., media disk drive interface 224 as an interface for a drive that can read and/or write to media including removable media such as floppy, CD-ROM, DVD, etc. media, display interface 225 as interface for a monitor or other display device, keyboard interface 228 as interface for a keyboard, pointing device interface 229 as an interface for a mouse or other pointing device, and miscellaneous other interfaces not shown individually, such as parallel and serial port interfaces, a universal serial bus (USB) interface, and the like.

Memory 222 interfaces with computer bus 221 so as to provide information stored in memory 222 to CPU 226 during execution of software programs such as an operating system, application programs, device drivers, and software modules that comprise program code, and/or computer-executable process steps, incorporating functionality described herein, e.g., one or more of process flows described herein. CPU 226 first loads computer-executable process steps from storage, e.g., memory 222, storage medium/media 223, removable media drive, and/or other storage device. CPU 226 can then execute the stored process steps in order to execute the loaded computer-executable process steps. Stored data, e.g., data stored by a storage device, can be accessed by CPU 226 during the execution of computer-executable process steps.

Persistent storage medium/media 223 is a computer readable storage medium(s) that can be used to store software and data, e.g., an operating system and one or more application programs. Persistent storage medium/media 223 can also be used to store device drivers, such as one or more of a digital camera driver, monitor driver, printer driver, scanner driver, or other device drivers, web pages, content files, playlists and other files. Persistent storage medium/media 223 can further include program modules and data files used to implement one or more embodiments of the present disclosure.

For the purposes of this disclosure a computer readable medium stores computer data, which data can include computer program code that is executable by a computer, in machine readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

For the purposes of this disclosure a module is a software, hardware, or firmware (or combinations thereof) system, process or functionality, or component thereof, that performs or facilitates the processes, features, and/or functions described herein (with or without human interaction or augmentation). A module can include sub-modules. Software components of a module may be stored on a computer readable medium. Modules may be integral to one or more servers, or be loaded and executed by one or more servers. One or more modules may be grouped into an engine or an application.

In an embodiment, the autonomous intravenous insertion system of the present disclosure includes a sensor for acquiring data in real-time, wherein the data relates to a vessel of a patient; an actuator for automatic completion of a medical procedure, and a computer configured to transform the data acquired by the sensor into a command to instruct the actuator to automatically complete the medical procedure.

In an embodiment, the autonomous intravenous insertion system of the present disclosure includes at least one sensory device for acquiring data in real-time, wherein the data relates to three-dimensional coordinates of a vessel of a patient receiving a medical procedure; at least one actuator for autonomous completion of the medical procedure; and a computer configured to transform the data from the coordinates of the vessel into a command to instruct the actuator to automatically complete the medical procedure.

In an embodiment, the autonomous intravenous insertion system of the present disclosure includes a plurality of sensory devices for acquiring data in real-time, wherein the data relates to three-dimensional coordinates of a vessel of a patient receiving a medical procedure; a plurality of actuators for autonomous completion of the medical procedure; and a computer configured to transform the data in real-time from the three-dimensional coordinates of the vessel into a command to instruct the actuators to automatically complete the medical procedure.

In an embodiment, the autonomous intravenous insertion system of the present disclosure includes a sensory device for acquiring data in real-time, wherein the data indicates three-dimensional coordinates of a vein of a patient receiving an insertion procedure; an actuator for autonomous completion of the insertion procedure; and a computer configured to transform the data in real-time from the three-dimensional coordinates of the vein into a command to instruct the actuators to automatically insert a medical device into the vein of the patient to complete the insertion procedure. In an embodiment, the medical device comprises a needle. In an embodiment, the medical device comprises a cannula.

In an embodiment, the autonomous intravenous insertion system of the present disclosure includes one or more sensory devices for acquiring three-dimensional coordinates and orientation of a patient's vein; one or more actuators for autonomous insertion of a needle or cannula into the patient's vein; and a computer configured to transform the acquired three-dimensional coordinates and orientation of the patient's vein into an optimal insertion path for the needle or cannula to be inserted into the patient's vein, wherein the sensory devices track the optimal insertion path for the needle or cannula in real-time so that the computer can execute a command to the actuators to instruct the actuators to guide the needle or cannula along the optimal insertion path to insert the needle or cannula into the patient's vein.

In an embodiment, a method for autonomous intravenous insertion of a medical device into a vessel of a patient comprises providing an autonomous intravenous insertion system comprising at least one sensory device for acquiring data relating to the patient's vessel, at least one actuator for autonomous insertion of the medical device into the patient's vessel, and a computer configured to transform the acquired data into a command to instruct the at least one actuator to automatically insert the medical device into the patient's vessel; acquiring, using the at least one sensory device, real-time data relating to the patient's vessel, generating, using the computer, an optimal insertion path for the medical device to be inserted into the patient's vessel, wherein the optimal insertion path is generated based on real-time data acquired by the sensory device; transforming, using the computer, the three-dimensional coordinates and orientation of the patient's vessel into a command to instruct the at least one actuator to automatically insert the medical device into the patient's vessel; and inserting, using the at least one actuator, the medical device into the patient's vessel along the optimal insertion path generated by the computer.

In an embodiment, a method for autonomous intravenous insertion of a needle into a vein of a patient comprises providing an autonomous intravenous insertion system comprising at least one sensory device for acquiring data relating to the patient's vein, at least one actuator for autonomous insertion of the needle into the patient's vein, and a computer configured to transform the data acquired by the sensory device into a command to instruct the at least one actuator to automatically insert the needle into the patient's vein; acquiring, using the at least one sensory device, real-time data relating to the patient's vein, wherein the real-time data comprises three-dimensional coordinates of the patient's vein; generating, using the computer, an optimal insertion path for the needle to be inserted into the patient's vein; transforming, using the computer, the three-dimensional coordinates of the patient's vein into a command to instruct the at least one actuator to automatically insert the needle into the patient's vein; and inserting, using the at least one actuator, the needle into the patient's vein along the optimal insertion path.

In an embodiment, a method for autonomous intravenous insertion of a cannula into a vein of a patient comprises providing an autonomous intravenous insertion system comprising at least one sensory device for acquiring data relating to the patient's vein, at least one actuator for autonomous insertion of the cannula into the patient's vein, and a computer configured to transform the data acquired by the sensory device into a command to instruct the at least one actuator to automatically insert the cannula into the patient's vein; acquiring, using the at least one sensory device, real-time data relating to the patient's vein, wherein the real-time data comprises three-dimensional coordinates of the patient's vein; generating, using the computer, an optimal insertion path for the cannula to be inserted into the patient's vein; transforming, using the computer, the three-dimensional coordinates of the patient's vein into a command to instruct the at least one actuator to automatically insert the cannula into the patient's vein; and inserting, using the at least one actuator, the needle into the patient's vein along the optimal insertion path.

In an embodiment, a method for autonomous intravenous insertion of a needle into a vein of a patient comprises providing an autonomous intravenous insertion system comprising at least one sensory device for acquiring data relating to the patient's vein, at least one actuator for autonomous insertion of the needle into the patient's vein, and a computer configured to transform the data acquired by the sensory device into a command to instruct the at least one actuator to automatically insert the needle into the patient's vein; acquiring, using the at least one sensory device, real-time data relating to the patient's vein, identifying, using the computer, an target insertion site for the needle to be inserted into the patient's vein; tracking, using the at least one sensory device, the target insertion site, wherein tracking the target insertion site occurs in real-time; generating, using the computer to process the data acquired by the sensory devices, three-dimensional coordinates of the patient's vein, wherein the three-dimensional coordinates are used by the computer to determine an optimal insertion path and an optimal orientation for the needle to be inserted into the patients vein; positioning, using the at least one actuator, the needle in close proximity to the patient's vein, wherein when the needle is in close proximity to the patient's vein, the needle is positioned in the optimal insertion path and the optimal orientation; verifying, using the at least one sensory device, the existence of the vein underneath the target insertion site; determining, using the at least one sensory device, an insertion depth for the needle to be inserted into the vein along the optimal insertion path; generating, using the computer, an updated optimal insertion path and an updated optimal orientation for the needle to be inserted based on a movement of the patient detected while using the at least one sensory device to track the target insertion site in real-time; transforming, using the computer, the updated optimal insertion path and the optimal orientation for the needle to be inserted in real-time into a command to instruct the at least one actuator to automatically reposition the needle in the updated optimal insertion path and the optimal orientation to insert the needle into the patient's vein; and inserting, using the at least one actuator, the needle into the patient's vein along the optimal insertion path.

In an embodiment, there is provided an autonomous intravenous needle insertion system that may be comprised of a robotic arm for positioning the needle, a robot controller for converting commands into movement, a master computer for interpreting data and sending commands to the robot and other actuators, sensors for locating veins including but not limited to a NIR camera and Laser Rangefinder, quick-change tooling for manipulation of different medical devices with the same system, and various support devices such as dispensers for new needles and blood collection tubes, storage for blood samples, a disposal unit, an automated tourniquet, an ambient lighting control unit, and a docking station for various manipulators.

In an embodiment, there is provided a control program that incorporates data from sensors such as cameras, rangefinders and ultrasound probes, converts that data into information about the 3-dimensional location, orientation and local topography of veins in a human body, and uses the data to command a robot arm to insert the needle safely into the target vein, using tracking algorithms to keep targets in sight in case of patient movement.

In an embodiment, there is provided a control program for completing an entire intravenous needle insertion procedure autonomously, including the loading and manipulating of devices commonly associated with intravenous insertion procedures, gathering of data about the subject, inserting needles into veins reliably and accurately, and discarding used equipment.

In an embodiment, there are provided control functions to handle autonomous needle insertion of everyday medical devices on humans, such as syringes, VACUTAINER® tubes, cannulas, and catheters In an embodiment, there are provided control functions to control and handle all tasks and procedures associated with needle insertion procedures In an embodiment, there is provided a method of finding superficial veins using ambient light (natural sunlight or other sources that produce diffuse near-infrared light) and a video camera with a near-infrared (NIR) filter to block all but wavelengths that are absorbed by blood significantly more than by skin, water or surrounding tissues, and processing the resulting image into a binary image where one color represents veins and the other represents everything else.

In an embodiment, there is provided a method of analyzing binary images of veins to determine defining characteristics such as length, diameter, orientation and position relative to other veins, and using that information to determine the best targets for intravenous needle insertion based on medical science, patient history and history of successful insertions performed by the robot on all subjects.

In an embodiment, there is provided an algorithm for scoring potential insertion sites based on length, diameter, orientation and position relative to the subject's elbow.

In an embodiment, there is provided a method of moving a camera and rangefinder with a robot arm to determine 3D coordinates of an object in the robot's coordinate system using geometry of the assembly and the camera lens In an embodiment, there is provided a method for calibrating the above system without human input, whereby the robot moves the assembly gathering data about a simple object such as a black circle on a piece of paper, and uses the changes in shape and size resulting from different movements to determine the conversion factor between pixels in an image and physical dimensions in space for any given reading from the rangefinder.

In an embodiment, there is provided a method for tracking an object with a robot arm in real time using the above system to quickly determine relative distances between the robot arm and the target, and using that information to follow the target.

In an embodiment, autonomous intravenous insertion systems and methods for using the system for autonomous insertion of a needle or cannula into a vessel are disclosed herein. In an embodiment, there is provided an autonomous intravenous insertion system that includes one or more sensory devices for acquiring three-dimensional coordinates and orientation of a patient's vessel; one or more actuators for autonomous insertion of a needle or cannula into the patient's vessel; and a computer configured to transform the acquired three-dimensional coordinates and orientation of the patient's vessel into an optimal insertion path for the needle or cannula to be inserted into the patient's vessel, wherein the sensory devices track the optimal insertion site in real-time so that the computer can execute a command to the actuators to instruct the actuators to guide the needle or cannula to that site along a suitable insertion path to insert the needle or cannula into the patient's vessel.

In an embodiment, there is provided a method for autonomous intravenous insertion of a needle into a vessel of a patient that includes providing an autonomous intravenous insertion system comprising at least one sensory device for acquiring data relating to the patient's vessel, at least one actuator for autonomous insertion of the needle into the patient's vessel, and a computer configured to transform the data acquired by the sensory device into a command to instruct the at least one actuator to automatically insert the needle into the patient's vessel; acquiring, using the at least one sensory device, real-time data relating to the patient's vessel, wherein the real-time data comprises three-dimensional coordinates of the patient's vessel; generating, using the computer, an optimal insertion path for the needle to be inserted into the patient's vessel; transforming, using the computer, the three-dimensional coordinates of the patient's vessel into a command to instruct the at least one actuator to automatically insert the needle into the patient's vessel; and inserting, using the at least one actuator, the needle into the patient's vessel along the optimal insertion path.

In an embodiment, there is provided a method of using an intravenous insertion system that includes providing an autonomous intravenous insertion system comprising at least one sensory device for acquiring data relating to the patient's vessel, at least one actuator for autonomous insertion of the cannula into the patient's vessel, and a computer configured to transform the data acquired by the sensory device into a command to instruct the at least one actuator to automatically insert the cannula into the patient's vessel; acquiring, using the at least one sensory device, real-time data relating to the patient's vessel, wherein the real-time data comprises three-dimensional coordinates of the patient's vessel; generating, using the computer, an optimal insertion path for the cannula to be inserted into the patient's vessel; transforming, using the computer, the three-dimensional coordinates of the patient's vessel into a command to instruct the at least one actuator to automatically insert the cannula into the patient's vessel; and inserting, using the at least one actuator, the needle into the patient's vessel along the optimal insertion path.

In an embodiment, there is provided a method of using an intravenous insertion system that includes providing an autonomous intravenous insertion system comprising at least one sensory device for acquiring data relating to the patient's vessel, at least one actuator for autonomous insertion of a VACUTAINER® needle into the patient's vessel, and a computer configured to transform the data acquired by the sensory device into a command to instruct the at least one actuator to automatically insert the cannula into the patient's vessel; acquiring, using the at least one sensory device, real-time data relating to the patient's vessel, wherein the real-time data comprises three-dimensional coordinates of the patient's vessel; generating, using the computer, an optimal insertion path for the cannula to be inserted into the patient's vessel; transforming, using the computer, the three-dimensional coordinates of the patient's vessel into a command to instruct the at least one actuator to automatically insert the cannula into the patient's vessel; inserting, using the at least one actuator, the needle into the patient's vessel along the optimal insertion path; and drawing one or more blood samples, using at least one actuator, by puncturing empty VACUTAINER® tubes according to procedure specifications.

In an embodiment, the robot arm described is used merely as a needle positioning device. In an embodiment, other configurations of actuators can be used to position the tools used to manipulate the contemplated medical devices, In an embodiment, other systems of actuators may differ from the robot arm of the present disclosure in that they may not consist entirely of revolute joints. In an embodiment, an actuator may include a combination of 3 or more prismatic (linear) joints to position the needle in three dimensions (x, y, and z) and 2 or more revolute joints to align the needle with the target vessel and arm contour may be used.

In an embodiment, the tool used to manipulate the medical device may or may not have an actuator on board to insert the needle. In an embodiment, in the case of the Catheter Tool, the robot arm inserts the needle, whereas in the case of the Blood Drawing Tool, the tool itself has an on-board actuator that takes care of inserting and extracting the needle. In an embodiment, a tool used for inserting catheters includes an on-board actuator for inserting the catheter into the target vessel. In an embodiment, the robot arm or other system of actuators to insert blood drawing needles may be used in place of the Blood Drawing Tool's on-board actuator. In an embodiment, any type of automated or user triggered mechanical needle insertion mechanism may be used as part of system 8 for inserting a needle into the subject arm.

In an embodiment, other working mechanisms may be used to achieve the same outcome as the mechanisms embedded in the tools described herein.

In an embodiment, it should be noted that the needle to be inserted is visible to the patient. In an embodiment, the needle might be hidden from a patient's view to limit discomfort elicited from viewing needles. In one embodiment, insertable devices may be hidden in the tool that manipulates them until the time when the needle is about to be inserted. In another embodiment, the needle is completely hidden from the patient throughout the entire procedure. In this embodiment, the needle may be kept within the body of a tool.

In an embodiment, the sensors are mounted onto the robot arm, and visual servoing techniques are used to position the needle accurately. Other sensor configurations may exist. For instance, in an embodiment, the sensors are in a fixed position above target insertion area. In an embodiment, the sensors are mounted on their own positioning system above the target insertion area, and are autonomously positioned to be directly over the target insertion site.

In an embodiment, no ultrasound imaging unit is appended. In an embodiment, the ultrasound imaging device is manipulated by its own manipulator and appended to the robot arm. In an embodiment, the ultrasound imaging device has its own manipulator stationed nearby the target insertion site, and is autonomously deployed before and while the insertion procedure is underway. In an embodiment, the ultrasound probe is built in to the tools used to manipulate medical devices. In this embodiment, the tool may make contact with the patient, and therefore, the needle may be hidden within the tool to avoid premature contact with the patient.

In an embodiment, the sensors used to localize a target vessel are a NIR only camera and a laser rangefinder. In an embodiment, other three dimensional localization systems are used. Other three dimensional localization systems include, but are not limited to, stereo cameras, a system of two or more cameras (not necessarily aligned as stereo cameras are), LADAR, LIDAR or other similar range finding unit, a system of one or more cameras combined with one or more laser rangefinders, and ultrasound.

In an embodiment, force feedback methods for sensing whether or not a needle has penetrated the skin, whether or not a needle has penetrated a vessel and whether or not a vessel is present in the target location are used. In an embodiment, a force sensor may be utilized in conjunction with a positioning device to obtain such information.

In an embodiment, a system for autonomous intravenous insertion includes a robot arm, one or more sensors pivotally attached to the robot arm for gathering information about potential insertion sites in a subject arm, a medical device pivotally attached to the robot arm, and a controller in communication with the sensors and the robot arm, wherein the controller receives the information from the sensors about potential insertion sites, and the controller selects a target insertion site and directs the robot arm to insert the medical device into the target insertion site.

In an embodiment, a system for autonomous intravenous insertion includes a robot arm, a plurality of sensors attached to the robot arm for gathering information about potential insertion sites in a subject arm, a medical device holding tool detachably engaged to the robot arm, the tool comprising a plurality of grippers for holding a medical device to be inserted into the subject arm, a first actuating mechanism for actuating the plurality grippers, stabilizing feet; and a second actuating mechanism for placing the stabilizing feet in the proximity to an insertion site, and a controller in communication with the plurality sensors, the medical device holding tool, and the robot arm, wherein the controller receives the information from the sensors about potential insertion sites, and selects a target insertion site and directs the medical device holding tool and the robot arm to insert the medical device into the target insertion site.

In an embodiment, a method for autonomous intravenous insertion includes securing a subject arm, identifying a target insertion site based on information received from at least one sensor, actuating a robot arm to deliver a medical device to the target insertion site, while monitoring the target insertion site, and inserting the medical device into the subject arm at the insertion site.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A system for an intravenous insertion, the system comprises:
    a robotic positioning system comprising a holding tool being configured to hold an end-effector for insertion into a blood vessel at a target insertion site;
    a sensor assembly including one or more sensors to gather information about the target insertion site in the blood vessel, wherein the sensor assembly is in a fixed relation to the target insertion site or to the end-effector; and
    a controller in communication with the one or more sensors and the robotic positioning system, wherein the controller is programmed to receive and process the information from the one or more sensors about the target insertion site in the blood vessel and to autonomously direct the end-effector into the blood vessel at the target insertion site based on the information received from the one or more sensors,
    wherein the information about the target insertion site comprises three-dimensional coordinates and orientation of the blood vessel.

2. The system of claim 1 wherein the information about the target insertion site further comprises information about topography at the target insertion site.

3. The system of claim 1 further including one or more inflatable cuffs configured to stabilize the blood vessel or increase a visibility of the blood vessel.

4. The system of claim 1 wherein the controller is further programmed to calculate an insertion path of the end-effector into the blood vessel based on the information about the target insertion site, and to autonomously direct the robotic positioning system to insert the end-effector along the insertion path into the blood vessel at the target insertion site.

5. The system of claim 1 wherein the one or more sensors include an ultrasound probe to verify that a blood vessel exists at the target insertion site.

6. The system of claim 1 further comprising stabilizing feet designed to stabilize a subject arm as the end-effector is being inserted into the target insertion site in the subject arm.

7. The system of claim 1, wherein the controller is programmed to receive from the one or more sensors information about a plurality of potential insertion sites, generate a ranking of potential insertion sites based on size, shape, and location of the potential insertion sites; prioritize the potential insertion sites based on the ranking, and select the target insertion site based on the ranking of the potential insertion sites.

8. A system for an intravenous insertion, the system comprises:
    a sensor assembly including one or more sensors to gather information about a target insertion site in a blood vessel of a subject; and
    a holding tool being configured to hold an end-effector for insertion into the blood vessel
    wherein the sensor assembly is configured to be maintained in a fixed relation to the target insertion site or to the end-effector,
    wherein the end-effector is directed into the blood vessel at the target insertion site based on the information received from the one or more sensors, and
    wherein the information about the target insertion site comprises three-dimensional coordinates and orientation of the blood vessel.

9. The system of claim 8 wherein the information about the target insertion site further comprises information about topography at the target insertion site.

10. The system of claim 8 further including one or more inflatable cuffs configured to stabilize the blood vessel or increase a visibility of the blood vessel.

11. The system of claim 8 wherein the holding tool comprises a fastener for modular attachment to a corresponding fastener on an insertion module to enable an autonomous exchange of end-effectors.

12. The system of claim 8 wherein the one or more sensors include an ultrasound probe to verify that a blood vessel exists at the target insertion site.

13. The system of claim 8 further comprising stabilizing feet designed to stabilize subject arm as the end-effector is being inserted into the target insertion site in the subject arm.

14. A system for an intravenous insertion, the system comprises:

a sensor assembly including one or more sensors to gather information about one or more insertion sites in one or more blood vessels of a subject;

a holding tool being configured to hold an end-effector for insertion into a blood vessel of the one or more blood vessels; and a controller in communication with the one or more sensors, wherein the controller is programmed to receive and process the information from the one or more sensors about the one or more insertion sites and to select a target insertion site at a target blood vessel based on the information from the one or more sensors such that the end-effector is directed into the target blood vessel at the target insertion site, wherein the sensor assembly is configured to be maintained in a fixed relation to the target insertion site or to the end-effector, and wherein the information about the one or more insertion sites comprises three-dimensional coordinates and orientation of the one or more blood vessels.

15. The system of claim 14 wherein the information about the one or more insertion sites further comprises information about topography at the target insertion site.

16. The system of claim 14 further including one or more inflatable cuffs configured to stabilize the one or more blood vessels or increase a visibility of the one or more blood vessels.

17. The system of claim 14 wherein the controller is further programmed to calculate an insertion path of the end-effector into the target blood vessel based on the information about the target insertion site, and to autonomously direct a robotic positioning system to insert the end-effector along the insertion path into the blood vessel at the target insertion site.

18. The system of claim 17 wherein the one or more sensors include an ultrasound probe to verify that the target blood vessel exists at the target insertion site.

19. The system of claim 17 further comprising stabilizing feet designed to stabilize a subject arm as the end-effector is being inserted into the target blood vessel in the subject arm.

20. The system of claim 17, wherein the controller is programmed to provide a ranking the one or more insertion sites based on size, shape, and location of the one or more insertion sites; prioritize the one or more insertion sites based on the ranking, and select the target insertion site based on the ranking the one or more insertion sites.

21. The system of claim 17, wherein the holding tool further comprises:

a plurality of grippers for holding the end-effector;

a first actuating mechanism to actuate the plurality of grippers;

stabilizing feet;

a second actuating mechanism to place the stabilizing feet in proximity to an insertion site; and a third actuating mechanism to advance the end-effector into the target blood vessel at the target insertion site.

* * * * *